US009921232B2

(12) United States Patent
Collier et al.

(10) Patent No.: US 9,921,232 B2
(45) Date of Patent: Mar. 20, 2018

(54) ELLAGIC ACID FORMULATIONS FOR USE IN COAGULATION ASSAYS

(71) Applicant: Abbott Point of Care Inc., Princeton, NJ (US)

(72) Inventors: Gordon Bruce Collier, Fitzroy Harbour (CA); Paul Willis Johns, Jr., Columbus, OH (US); Smitha R K Sutrala, Kanata (CA); Dan Wang, Kanata (CA); Katrina Petronilla Di Tullio, Stittsville (CA)

(73) Assignee: Abbott Point of Care Inc., Princeton, NJ (US)

( * ) Notice: Subject to any disclaimer, the term of this patent is extended or adjusted under 35 U.S.C. 154(b) by 157 days.

(21) Appl. No.: 14/866,518

(22) Filed: Sep. 25, 2015

(65) Prior Publication Data
US 2016/0091512 A1 Mar. 31, 2016

Related U.S. Application Data

(60) Provisional application No. 62/055,768, filed on Sep. 26, 2014.

(51) Int. Cl.
*G01N 33/86* (2006.01)
*B01L 3/00* (2006.01)

(52) U.S. Cl.
CPC ............ *G01N 33/86* (2013.01); *B01L 3/5027* (2013.01); *B01L 3/502715* (2013.01); *B01L 2200/0605* (2013.01); *B01L 2200/0684* (2013.01); *B01L 2200/0689* (2013.01); *B01L 2200/16* (2013.01); *B01L 2300/024* (2013.01); *B01L 2300/027* (2013.01); *B01L 2300/069* (2013.01); *B01L 2300/0636* (2013.01); *B01L 2300/0645* (2013.01); *B01L 2300/0816* (2013.01); *B01L 2300/0867* (2013.01); *B01L 2300/161* (2013.01); *B01L 2400/0472* (2013.01); *B01L 2400/0481* (2013.01); *B01L 2400/0487* (2013.01); *B01L 2400/0688* (2013.01); *G01N 2333/974* (2013.01)

(58) Field of Classification Search
CPC .. B01L 3/5027; B01L 3/52; B01L 3/50; B01L 2200/00; G01N 33/86
USPC ............................... 422/73, 68.1, 50; 436/69
See application file for complete search history.

(56) References Cited

U.S. PATENT DOCUMENTS

| 3,486,981 A | 12/1969 | Speck |
| 4,304,853 A | 12/1981 | Jozefonvicz et al. |
| 4,496,653 A | 1/1985 | Lill et al. |
| 4,598,043 A | 7/1986 | Svendsen |
| 4,756,884 A | 7/1988 | Hillman et al. |
| 4,906,439 A | 3/1990 | Grenner |
| 4,954,087 A | 9/1990 | Lauks et al. |
| 4,959,324 A | 9/1990 | Ramel et al. |
| 5,039,617 A | 8/1991 | Mcdonald et al. |
| 5,055,412 A | 10/1991 | Proksch |
| 5,059,525 A | 10/1991 | Bartl et al. |
| 5,096,669 A | 3/1992 | Lauks et al. |
| 5,122,244 A | 6/1992 | Hoenes et al. |
| 5,132,086 A | 7/1992 | Allen et al. |
| 5,200,051 A | 4/1993 | Cozzette et al. |
| 5,234,813 A | 8/1993 | Mcgeehan et al. |
| 5,260,221 A | 11/1993 | Ramel et al. |
| 5,344,754 A | 9/1994 | Zweig |
| 5,447,440 A | 9/1995 | Davis et al. |
| 5,514,253 A | 5/1996 | Davis et al. |
| 5,554,339 A | 9/1996 | Cozzette et al. |
| 5,628,961 A | 5/1997 | Davis et al. |
| 5,821,399 A | 10/1998 | Zelin |
| 6,030,827 A | 2/2000 | Davis et al. |
| 6,352,630 B1 | 3/2002 | Frenkel et al. |
| 6,379,883 B2 | 4/2002 | Davis et al. |
| 6,438,498 B1 | 8/2002 | Opalsky et al. |
| 6,495,336 B1 | 12/2002 | Ludin et al. |
| 6,607,644 B1 | 8/2003 | Apffel, Jr. |
| 6,620,840 B1 | 9/2003 | Bigg et al. |
| 6,750,053 B1 | 6/2004 | Widrig Opalsky et al. |
| 6,936,473 B2 | 8/2005 | Nanba et al. |
| 7,419,821 B2 | 9/2008 | Davis et al. |
| 7,618,810 B2 | 11/2009 | Yang et al. |
| 7,736,901 B2 | 6/2010 | Opalsky et al. |
| 7,803,572 B2 | 9/2010 | Braven et al. |

(Continued)

FOREIGN PATENT DOCUMENTS

| DE | 10016775 | 8/2001 |
| EP | 2472261 B | 6/2014 |

(Continued)

OTHER PUBLICATIONS

U.S. Appl. No. 14/866,266, filed Sep. 25, 2015, Zhao et al.
U.S. Appl. No. 14/866,316, filed Sep. 25, 2015, Zhao et al.
U.S. Appl. No. 14/866,402, filed Sep. 25, 2015, Petronilla Di Tullio et al.
U.S. Appl. No. 14/866,432, filed Sep. 25, 2015, Petronilla Di Tullio et al.
U.S. Appl. No. 14/866,460, filed Sep. 25, 2015, Petronilla Di Tullio et al.
U.S. Appl. No. 14/866,488, filed Sep. 25, 2015, Taylor et al.
Girolami et al., The Effect of Ellagic Acid on Coagulation in Vivo, Blood, vol. 27, issue 1, Jan. 1, 1966, 11 pages.
Reitze et al., The Further Chemistry of Ellagic Acid: I. Synthesis of Tetramethylellagic Acid and Associated Polymer Precursors, Holzforschung, vol. 55, Issue 2, Feb. 2001, pp. 171-175.
Sefton et al., "The Thromboresistance of a Heparin-Polyvinyl Alcohol Hydrogel", Chem. Eng. Commun. vol. 30, pp. 141-154, 1984.
Smith et al., "Permeability of a heparin-polyvinyl alcohol hydrogen to thrombin and antithrombin ILL", J. Biomed Mater Res., pp. 673-685, Aug. 22, 1988.

(Continued)

*Primary Examiner* — Christine T Mui
(74) *Attorney, Agent, or Firm* — Kilpatrick Townsend & Stockton LLP

(57) ABSTRACT

The present invention relates to ellagic acid formulations for performing coagulation assays that are highly stable for long term storage and reduce assay time. Particularly, aspects of the present invention are directed to a composition and method of preparing ellagic acid in a highly soluble format for use in a coagulation assay. For example, the ellagic acid may be solubilized in one or more of sodium hydroxide, methanol, a polyether compound, particularly polyethylene glycol, polyethylene oxide, or polyoxyethylene, and a cyclodextrin guest-host complex.

30 Claims, 41 Drawing Sheets

(56) References Cited

U.S. PATENT DOCUMENTS

| | | | |
|---|---|---|---|
| 7,923,256 | B2 | 4/2011 | Widrig Opalsky et al. |
| 7,977,106 | B2 | 7/2011 | Widrig Opalsky et al. |
| 8,404,100 | B2 | 3/2013 | Wu |
| 8,465,635 | B2 | 6/2013 | Thürlemann et al. |
| 8,530,170 | B2 | 9/2013 | Bertin |
| 8,986,983 | B2 | 3/2015 | Montagu et al. |
| 9,091,699 | B2 | 7/2015 | Hsiue et al. |
| 9,194,859 | B2 | 11/2015 | Emeric et al. |
| 9,383,351 | B2 | 7/2016 | Fleming |
| 2004/0019300 | A1 | 1/2004 | Leonard |
| 2004/0191124 | A1 | 9/2004 | Noetzel et al. |
| 2005/0013732 | A1 | 1/2005 | Battrell et al. |
| 2006/0264779 | A1 | 11/2006 | Kemp et al. |
| 2007/0009982 | A1 | 1/2007 | Thurlemann et al. |
| 2007/0077610 | A1 | 4/2007 | Ghai et al. |
| 2007/0077613 | A1 | 4/2007 | Ghai et al. |
| 2008/0280285 | A1 | 11/2008 | Chen et al. |
| 2008/0318260 | A1 | 12/2008 | Mpock et al. |
| 2009/0107909 | A1 | 4/2009 | Kotera et al. |
| 2009/0143761 | A1 | 6/2009 | Cantor et al. |
| 2009/0221011 | A1 | 9/2009 | Stiene et al. |
| 2009/0236238 | A1 | 9/2009 | Doerge et al. |
| 2010/0200428 | A1 | 8/2010 | Choi et al. |
| 2010/0248273 | A1 | 9/2010 | Campbell et al. |
| 2011/0165595 | A1 | 7/2011 | Catanzaro et al. |
| 2011/0201099 | A1 | 8/2011 | Anderson et al. |
| 2011/0269648 | A1 | 11/2011 | Schwartz |
| 2011/0306070 | A1 | 12/2011 | Campbell et al. |
| 2012/0177537 | A1 | 7/2012 | Aota et al. |
| 2012/0329144 | A1 | 12/2012 | Kwak et al. |
| 2013/0000378 | A1 | 1/2013 | Martin et al. |
| 2013/0002278 | A1 | 1/2013 | Martin et al. |
| 2013/0209444 | A1* | 8/2013 | Dockal ............... A61K 31/737 424/130.1 |
| 2014/0014509 | A1 | 1/2014 | Yan et al. |
| 2014/0151224 | A1 | 6/2014 | Glezer et al. |
| 2016/0168624 | A1 | 6/2016 | Edwards et al. |
| 2017/0108461 | A1 | 4/2017 | Dimitrov |

FOREIGN PATENT DOCUMENTS

| | | | |
|---|---|---|---|
| JP | 2013205087 | 10/2013 | |
| WO | 9322453 | 11/1993 | |
| WO | 0136666 | 5/2001 | |
| WO | 0159425 | 8/2001 | |
| WO | 0241995 | 5/2002 | |
| WO | 03023389 | 3/2003 | |
| WO | 03076937 | 9/2003 | |
| WO | 2004061418 | 7/2004 | |
| WO | 2007025559 | 3/2007 | |
| WO | 2009053834 | 4/2009 | |
| WO | 2010060081 | 5/2010 | |
| WO | 2010128221 | 11/2010 | |
| WO | 2011148207 | 12/2011 | |
| WO | 2012013937 | 2/2012 | |
| WO | WO 2012/142317 | * 10/2012 | ............ A61L 15/32 |
| WO | 2014015191 | 1/2014 | |
| WO | 2014151450 | 9/2014 | |
| WO | 2016049557 | 3/2016 | |

OTHER PUBLICATIONS

Thuerlemann et al., "Monitoring Thrombin Generation by Electrochemistry: Development of an Amperometric Biosensor Screening Test for Plasma and Whole Blood", Clinical Chemistry, vol. 55, No. 3, 2009, pp. 505-512.

Xu et al., Synthesis, Characterization and Biomedical Properties of UV-Cured Polyurethane Acrylates Containing a Phosphorylcholine Structure, J. Biomater Sci Polym Ed, Nov. 15, 2011.

International Search Report and Written Opinion issued in International Application No. PCT/US2015/0524089, dated Feb. 2, 2016, 14 pages.

"Non-Final Office Action" issued in U.S. Appl. No. 14/866,266, dated May 15, 2017, 27 pages.

"Non-Final Office Action" issued in U.S. Appl. No. 14/866,402, dated Mar. 28, 2017, 18 pages.

"Notice of Allowance" issued in U.S. Appl. No. 14/866,402, dated Aug. 31, 2017, 16 pages.

"Non-Final Office Action" issued in U.S. Appl. No. 14/866,432, dated Mar. 29, 2017, 15 pages.

"Notice of Allowance" issued in U.S. Appl. No. 14/866,432, dated Sep. 1, 2017, 16 pages.

"Non-Final Office Action" issued in U.S. Appl. No. 14/866,460, dated Sep. 14, 2017, 18 pages.

Maitz et al., "Bio-responsive polymer hydrogels homeostatically regulate blood coagulation", Nature Communications, vol. 4, No. 2168, 2013, pp. 1-7.

"International Search Report and Written Opinion", issued in PCT/US2015/052317, dated Feb. 5, 2016, 12 pages.

"International Search Report and Written Opinion", issued in PCT/US2015/052333, dated Feb. 22, 2016, 21 pages.

International Search Report and Written Opinion, issued in PCT/US2015/052356, dated Jan. 11, 2016, 15 pages.

"International Search Report and Written Opinion", issued in PCT/US2015/052368, dated Jan. 26, 2016, 12 pages.

"International Search Report and Written Opinion", issued in PCT/US2015/052389, dated Mar. 15, 2016, 17 pages.

"International Search Report and Written Opinion", issued in PCT/US2015/052399, dated Jan. 26, 2016, 11 pages.

Pierson "Metabolism and function of phenazines in bacteria: impacts on the behavior of bacteria in the environment and biotechnological processes", Appl. Microbiol Biotechnol, vol. 86, 2010, 12 pages.

Strehlitz et al., "Protein Detection with Aptamer Biosensors", Review Sensors, vol. 8, 2008, pp. 4296-4307.

"Notice of Allowance" issued in U.S. Appl. No. 14/866,266, dated Oct. 11, 2017, 25 pages.

"Non-Final Office Action" issued in U.S. Appl. No. 14/866,316, dated Nov. 17, 2017, 19 pages.

"Non-Final Office Action" issued in U.S. Appl. No. 14/866,488, dated Dec. 6, 2017, 9 pages.

* cited by examiner

Fresh preparation of Ellagic acid in sodium hydroxide 2 day old preparation of Ellagic acid in sodium hydroxide at room temperature Fresh Ellagic acid preparation in methanol 6 day old Ellagic acid preparation in methanol at room temperature 13 day old Ellagic acid preparation in methanol at room temperature Fresh Ellagic acid in 1M PEG 400 (diluted in water)

6 days at room temperature Ellagic acid in 1M PEG 400 (diluted in methanol)

6 days at room temperature Ellagic acid in 100 mM PEG 400

13 days at room temperature Ellagic acid in 100 mM PEG 4000

Fresh beta-cyclodextrin 6 days at room temperature beta-cyclodextrin

Fresh beta-cyclodextrin 6 days at room temperature beta-cyclodextrin

ELLAGIC ACID FORMULATIONS FOR USE IN COAGULATION ASSAYS

CROSS-REFERENCE TO RELATED APPLICATIONS

This application claims priority to U.S. Provisional Application No. 62/055,768 filed on Sep. 26, 2014, the entirety of which is incorporated herein by reference.

FIELD OF THE INVENTION

The present invention relates to ellagic acid formulations, and in particular, to performing coagulation assays using ellagic acid formulations in test devices.

BACKGROUND OF THE INVENTION

Blood clotting or hemostasis is an important protective mechanism of the body for sealing wounds caused from injury to the body. Hemostasis takes place in two phases. Primary (cellular) hemostasis serves to quickly stop bleeding and minimize blood loss. Primary hemostasis involves injured cells of the endothelium and the underlying layer of cells emitting signals that enable blood platelets (thrombocytes) to accumulate in a region of an injured blood vessel, forming a plug that provisionally seals the wound. Secondary (plasmatic) hemostasis or coagulation is initiated at the same time as primary hemostasis and involves a process by which blood clots. More specifically, coagulation is controlled by a signaling coagulation cascade consisting of thirteen coagulation factors that interact and activate each other. At the end of the coagulation cascade, fibrinogen is converted into fibrin. A network of fibrin fibers reinforces wound closure, and platelets and other blood cells get caught in this network and form a blood clot (thrombus). Lastly, platelets and the endothelium release growth factors that control a wound-healing process. At the end of these processes, the fibrin network is dissolved by enzymes in the blood plasma.

The coagulation cascade of secondary hemostasis is based on catalytic conversion of fibrinogen, a soluble plasma protein, to insoluble fibrin. The enzyme catalyzing this reaction is thrombin, which does not permanently circulate in the blood in an active form but exists as prothrombin, the inactive precursor of thrombin. The coagulation cascade leading to active thrombin consists of two pathways, the extrinsic and the intrinsic pathways, which converge into a common pathway that includes active thrombin catalyzing the conversion of fibrinogen to fibrin. The extrinsic pathway is initiated at the site of injury in response to the release of tissue factor (factor III) and thus, is also known as the tissue factor pathway. Tissue factor is a cofactor in the factor VIIa-catalyzed activation of factor X (inactive) to factor Xa (active). The second, more complex, intrinsic pathway is activated by clotting factors VIII, IX, X, XI, and XII associated with platelets. Also required are the proteins prekallikrein (PK) and high-molecular-weight kininogen (HK or HMWK), as well as calcium ions and phospholipids secreted from platelets. Each of these constituents leads to the conversion of factor X to factor Xa. The common point in both pathways is the activation of factor X to factor Xa. Factor Xa is an enzyme (e.g., a serine endopeptidase) that cleaves prothrombin in two places (an arg-thr and then an arg-ile bond), which yields active thrombin and ultimately results in the conversion of fibrinogen to fibrin.

Consequently, the coagulation cascade is a suitable target for diagnosing and treating diseases involving dysregulated blood clotting or the absence of clotting. For example, the diagnosis of hemorrhagic conditions such as hemophilia, where one or more of the thirteen blood clotting factors involved in the coagulation cascade may be defective, can be achieved by a wide variety of coagulation tests. In addition, several tests have been developed to monitor the progress of thrombolytic therapy. Other tests have been developed to signal a prethronibolytic or hypercoagulable state, or monitor the effect of administering protamine to patients during cardiopulmonary bypass surgery. However, the main value of coagulation tests is in monitoring oral and intravenous anticoagulation therapy. Three of the key diagnostic tests are prothrombin time (PT), activated partial thromboplastin time (aPTT), and activated clotting time (ACT).

Activators of blood clotting via each of the extrinsic and intrinsic pathways are known. For example, activation of the intrinsic pathway can occur by a variety of negatively charged insoluble substances. The action of these substances involves the specific adsorption of factor XII and other proteins of the contact activation system, leading to an acceleration of the proteolytic activation of factor XII, prekallikrein, and factor XI. Although most known activators of the intrinsic pathway such as glass, silica, celite, and kaolin are insoluble, activation has been reported to occur by polyanions heparin, dextran sulfate, carrageenans, and soluble ellagic acid (see, e.g., Girolami et al., 1966, Blood, 27(1):93-102). Unique amongst these substances is ellagic acid, which is a ubiquitous polyphenol found in many fruits, nuts and seeds, and an effective activated cephaloplastin reagent (commercially available cephaloplastin reagents typically also include a phospholipid, typically a cephalin, as a platelet substitute). Unfortunately, the aqueous insolubility of ellagic acid makes it disfavored for use as an activating reagent in many coagulation assays such as the aPTT that are designed for use in single use coagulation assay devices because activating reagents comprising ellagic acid often take a long time to prepare and are not stable after extended periods of storage (e.g., greater than 1-2 days at room temperature).

To address the aqueous insolubility of ellagic acid, a number of solutions have been proposed. For example, ellagic acid has been shown to be soluble in aprotic polar solvents such as N,N-diemthyl formamide, gamma butyrolactone, acetonitrile, and N-methyl-2-pyrrolidone (NMP) (see, e.g., Reitze et al., 2001, Holzforschung, 55:171-5). These solvents, however, are either toxic, not compatible with coagulation assays, or are not appropriate for use in a single use coagulation assay device as they pose safety, shelf-life, and other problems. Alternatively, soluble salts of ellagic acid have been generated by adding sodium hydroxide (see, e.g., U.S. Pat. No. 3,486,981). The soluble salt preparations, however, generate derivatives of ellagic acid, not solubilized ellagic acid, making their use in a single use coagulation assay device less desirable. Additionally, ellagic acid preparations with sodium hydroxide tend to be unstable for longer period of times, and thus, a preservative such as phenol is typically added to the ellagic acid preparation to stabilize the solution for longer periods of time (see, e.g., U.S. Pat. No. 5,055,412). These solutions, however, often take a long time to prepare, a manufacturing drawback which increases expense. Further, phenol is corrosive and causes liver and kidney damage, is a mutagen and potential reproductive hazard.

Consequently, many of the above-mentioned solutions to solubilize ellagic acid are not amenable for the preparation of ellagic acid as a reagent in single use coagulation assay devices. For example, many of the organic solvents are toxic, and will not be useful for long term room temperature storage, which is required of most single use disposable cartridges. Moreover, the addition of hydroxides and/or preservatives to solubilize and stabilize ellagic acid generates decomposition products (i.e., an inactive chemical species derived from ellagic acid) based on the dehydration of the alcohol group and/or saponification reaction of the two ester groups found in ellagic acid. Accordingly, the need exists for highly soluble, stable, and manufacturable ellagic acid suspensions for use in a blood-coagulation assay of a single use disposable cartridge.

SUMMARY OF THE INVENTION

In one embodiment, the present invention is directed to a coagulation test system comprising a reagent including ellagic acid and an agent for stably solubilizing the ellagic acid, and a substrate including a thrombin-cleavable peptide with a detectable moiety. The agent comprises at least one of a polyether compound and a cyclodextrin.

In some embodiments, the polyether compound is selected from the group consisting of polyethylene glycol, polyethylene oxide, polyoxyethylene, and mixtures thereof. Optionally, the agent is the polyethylene glycol comprising a molecular weight of about 200 to about 500000.

In some embodiments, the cyclodextrin is selected from the group consisting of (2-hydroxypropyl)-beta-cyclodextrin, (2-hydroxypropyl)-gamma-cyclodextrin, alpha-cyclodextrin, gamma-cyclodextrin, dimethyl-alpha-cyclodextrin, trimethyl-alpha-cyclodextrin, dimethyl-beta-cyclodextrin, trimethyl-beta-cyclodextrin, dimethyl-gamma-cyclodextrin, trimethyl-gamma-cyclodextrin, glycosyl-alpha-cyclodextrin, glycosyl-beta-cyclodextrin, diglycosyl-beta-cyclodextrin, maltosyl-beta-cyclodextrin, dimaltosyl-beta-cyclodextrin, sulfobutylether-beta-cyclodextrin, and mixtures thereof.

In some embodiments, the agent is the cyclodextrin, and the cyclodextrin is complexed with the ellagic acid. In other embodiments, the agent is the polyether compound and the cyclodextrin, and the cyclodextrin is complexed with the ellagic acid. Optionally, at least 80% of the ellagic acid is active ellagic acid.

In some embodiments, the coagulation test system further comprises at least one transducer coated with a polymer layer. The polymer layer comprises the thrombin-cleavable peptide with the detectable moiety. Optionally, the reagent is an activated partial thromboplastin time (aPTT) reagent formed as (i) a layer over the polymer layer, or (ii) a layer adjacent to the at least one transduce. Alternatively, the reagent is an activated partial thromboplastin time (aPTT) reagent, and the polymer layer comprises the aPTT reagent.

In another embodiment, the present invention is directed to a method of forming a coagulation test system comprising preparing an activator solution comprising ellagic acid and an agent comprising at least one of a polyether compound and a cyclodextrin for stably solubilizing the ellagic acid, mixing the activator solution with at least a phospholipid preparation to create a reagent solution, and adding the reagent solution to a substrate comprising a thrombin-cleavable peptide with a detectable moiety to create an assay cocktail.

In some embodiments, the method further comprises preparing a polymer matrix comprising a polymer, and adding the polymer matrix to the assay cocktail, and dispensing the assay cocktail over at least one transducer of a chip. Optionally, the polyether compound is selected from the group consisting of polyethylene glycol, polyethylene oxide, polyoxyethylene, and mixtures thereof.

In some embodiments, the agent is the polyethylene glycol. In other embodiments, the agent is the cyclodextrin, and the cyclodextrin is complexed with the ellagic acid. In alternative embodiments, the agent is the polyether compound and the cyclodextrin, and the cyclodextrin is complexed with the ellagic acid.

In some embodiments, the preparing the activator solution comprises dissolving the ellagic acid into the activator solution with the agent at neutral pH, adding an alkali to the activator solution to increase the pH of the activator solution into a pH range of 10-12.5, mixing the activator solution for a period of about 1 to 10 minutes, adding an acid to the activator solution to return the pH to a neutral pH to retain at least 80% of the ellagic acid as active ellagic acid, and mixing the activator solution with a buffer.

In another embodiment, the present invention is directed to a sample analysis cartridge comprising an inlet chamber configured to receive a biological sample, a conduit fluidically connected to the inlet chamber and configured to receive the biological sample from the inlet chamber, and a micro-environment activated partial thromboplastin time (aPTT) sensor located within the conduit, the sensor comprising a reagent comprising ellagic acid and an agent for stably solubilizing the ellagic acid, and at least one transducer coated with a polymer layer, wherein the polymer layer comprises a thrombin-cleavable peptide with a detectable moiety.

BRIEF DESCRIPTION OF THE DRAWINGS

The present invention will be better understood in view of the following non-limiting figures, in which.

DETAILED DESCRIPTION OF THE INVENTION

Figure 1:
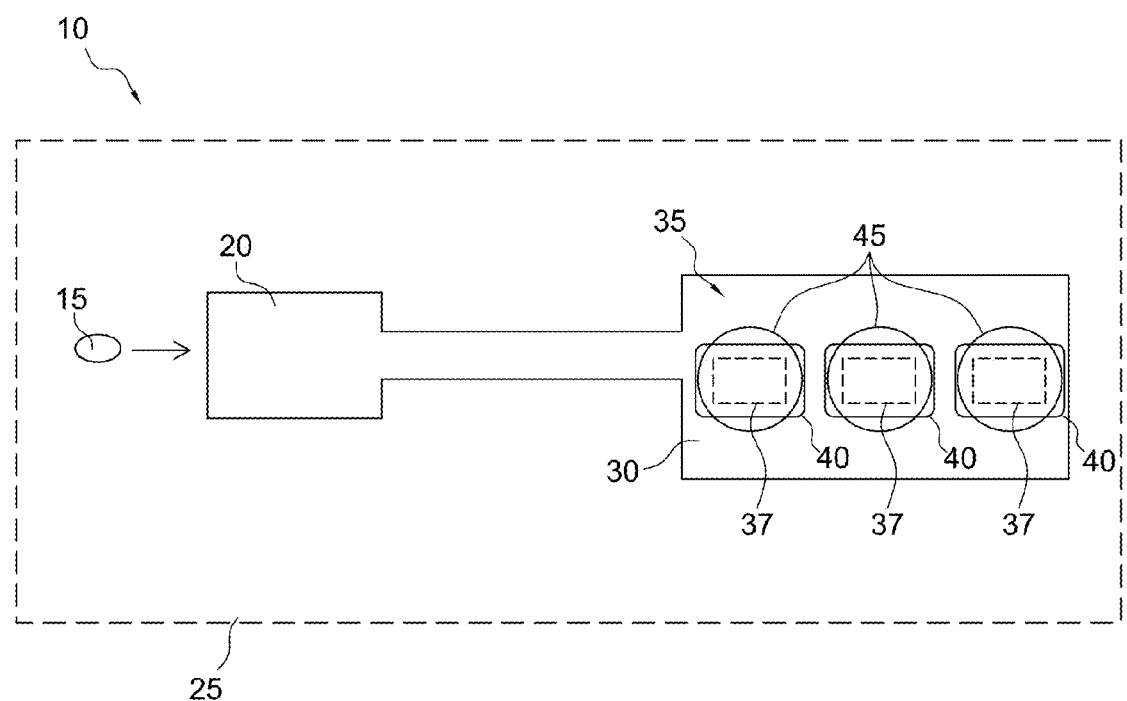
FIG. 1 shows a cartridge schematic in accordance with some aspects of the invention.

The present invention relates to ellagic acid formulations, and in particular, to performing coagulation assays using ellagic acid formulations in test devices.

In preferred embodiments, the invention relates to a composition and method of preparing ellagic acid (e.g., a coagulation activator) in a highly soluble format for use in a coagulation assay. The ellagic acid may be prepared in a format that includes a dry reagent which becomes rapidly solubilized in the coagulation assay. Additionally or alternatively, the ellagic acid may be prepared in a format that includes a polymer layer in a micro-environment format in order to physically separate reactive components generated from the presence of the ellagic acid to avoid cross-activation and promote localization of electrochemical or optical signals over at least one transducer. In some embodiments, the ellagic acid may be used to promote the activation of the intrinsic pathway in an aPTT assay.

In some embodiments, the invention relates to a composition and method of preparing a coagulation assay reagent comprising solubilizing ellagic acid in one or more of sodium hydroxide, methanol, a polyether compound, particularly polyethylene glycol, polyethylene oxide, or polyoxyethylene, and a cyclodextrin guest-host complex. In order to promote solubilization while minimizing dehydration of the alcohol group and/or saponification of the ester bonds in the ellagic acid, the composition and method of preparing the coagulation assay reagent may further comprise exposing the ellagic acid to a brief alkaline pH excursion. In some embodiments, the coagulation assay reagent may be used to promote the activation of the intrinsic pathway in an aPTT assay.

In accordance with these and other aspects of the present invention disclosed herein, the composition and method of preparing ellagic acid and the coagulation assay reagent advantageously achieve an ellagic acid formulation and coagulation assay reagent that are highly stable for long term storage and reduce the assay time of an aPTT coagulation assay.

As used herein, the term "micro-environment sensor" refers to a sensor configured such that any reaction occurring in the immediate vicinity of the sensor in a manner sufficient to achieve the desired signal at the sensor will not detectably interfere with (or impact) another reaction occurring at an adjacent sensor during normal usage.

As used herein, the term "heparin neutralizing" refers to an aspect of the sensor which renders unfractionated heparin and low-molecular-weight heparin (LMWH) biologically inactive in a biological sample in an area sufficient to span the micro-environment sensor area. Conversely, "non-heparin-neutralizing" refers to an aspect of the sensor that does not impact/affect the biological activity of unfractionated heparin or LMWH in the micro-environment sensor area.

As used herein, the term "immobilized" refers to an aspect of the micro-environment sensor which is substantially limited in movement, and thus localizing this aspect of the micro-environment to a general area.

As used herein, the term "substrate" refers to either a molecule which is the target of an enzymatic reaction or a physical entity which forms the foundation of a structure.

Overview of Blood Coagulation

The process of blood clotting and the subsequent dissolution of the clot following repair of the injured tissue is termed hemostasis. In order for hemostasis to occur, platelets must adhere to exposed collagen, release the contents of their granules, and aggregate. The adhesion of platelets to the collagen exposed on endothelial cell surfaces is mediated by von Willebrand factor (vWF). The activation of platelets via thrombin is required for their consequent aggregation to a platelet plug. However, equally significant is the role of activated platelet surface phospholipids in the activation of the coagulation cascade.

The intrinsic pathway of the coagulation cascade requires the clotting factors VIII, IX, X, XI, and XII. Also required are the proteins prekallikrein (PK) and high-molecular-weight kininogen (HK or HMWK), as well as calcium ions and phospholipids secreted from platelets. Each of these intrinsic pathway constituents leads to the conversion of factor X to factor Xa. Initiation of the intrinsic pathway occurs when prekallikrein, high-molecular-weight kininogen, factor XI and factor XII are exposed to a negatively charged surface. This is termed the contact phase and can occur as a result of interaction with the phospholipids (primarily phosphatidylethanolamine, PE) of circulating lipoprotein particles such as chylomicrons, very low density lipoproteins (VLDLs), and oxidized low density lipoproteins (LDLs). This is the basis of the role of hyperlipidemia in the promotion of a pro-thrombotic state.

The activation of factor Xa in the intrinsic pathway requires assemblage of the tenase complex ($Ca^{2+}$ and factors VIIIa, IXa and X) on the surface of activated platelets. One of the responses of platelets to activation is the presentation of phosphatidylserine (PS) and phosphatidylinositol (PI) on their surfaces. The exposure of these phospholipids allows the tenase complex to form and the subsequent activation of factor Xa.

The extrinsic pathway of the coagulation cascade is initiated at the site of injury in response to the release of tissue factor (factor III) and thus, is also known as the tissue factor pathway. Tissue factor is a cofactor in the factor VIIa-catalyzed activation of factor X. Factor VIIa, a gla residue containing serine protease, cleaves factor X to factor Xa in a manner identical to that of factor IXa of the intrinsic pathway. The activation of factor VII occurs through the action of thrombin or factor Xa. The ability of factor Xa to activate factor VII creates a link between the intrinsic and extrinsic pathways.

The common point in both pathways is the activation of factor X to factor Xa. Factor Xa activates prothrombin (factor II) to thrombin (factor IIa). Thrombin, in turn, converts fibrinogen to fibrin. The activation of thrombin occurs on the surface of activated platelets and requires formation of a prothrombinase complex. This complex is composed of the platelet phospholipids, phosphatidylinositol and phosphatidylserine, $Ca^{2+}$, factors Va and Xa, and prothrombin. Factor V is a cofactor in the formation of the prothrombinase complex, similar to the role of factor VIII in the tenase complex formation. Like factor VIII activation, factor V is activated to factor Va by means of minute amounts and is inactivated by increased levels of thrombin. Factor Va binds to specific receptors on the surfaces of activated platelets and forms a complex with prothrombin and factor Xa.

Prothrombin is a 72 kDa, single-chain protein containing ten gla residues in its N-terminal region. Within the prothrombinase complex, prothrombin is cleaved at 2 sites by factor Xa. This cleavage generates a 2-chain active thrombin molecule containing an A and a B chain which are held together by a single disulfide bond. Thrombin binds to a class of G-protein-coupled receptors (GPCRs) called protease activated receptors (PARs), specifically PAR-1, -3 and -4. PARs utilize a unique mechanism to convert the result of extracellular proteolytic cleavage into an intracellular signaling event. PARs carry their own ligand, which remains inactive until protease cleavage, such as by thrombin, "unmasks" the ligand. Following thrombin cleavage the unmasked ligand is still a part of the intact PAR but is now capable of interacting with the ligand-binding domain of the PAR resulting in the activation of numerous signaling cascades.

Overview of Coagulation Testing

Bleeding time assays are used to evaluate the vascular and platelet responses that are associated with hemostasis. The bleeding time is a frequent assay performed on preoperative patients to ensure there is an adequate response to vessel injury prior to surgery. As discussed herein, the rapid responses to vascular injury (occurring within seconds) are vessel constriction and platelet adhesion to the vessel wall. The Ivy method for determining the bleeding time involves the use of a blood pressure cuff (sphygmomanometer) which is placed on the forearm and inflated to 40 mm Hg. A superficial incision is then made on the forearm and the time it takes for bleeding to stop is recorded. With the Ivy method bleeding should stop within 1-9 minutes. Any bleeding time greater than 15 minutes would be indicative of a defect in the initial responses of vessels and platelets to vascular injury. A less invasive bleeding time assay involves the use of a lancet or special needle, with which a 3-4 mm deep prick is made on the fingertip or earlobe. This bleeding time assay is referred to as the Duke method, and in this assay bleeding should cease within 1-3 minutes. The bleeding time is affected (prolonged) by any defect in platelet function, by vascular disorders, and in von Willebrand disease but is not affected by other coagulation factors. Disorders that are commonly associated with an increased bleeding time include thrombocytopenia, disseminated intravascular coagulation (DIC), Bernard-Soulier syndrome and Glanzmann thrombasthenia. Abnormal bleeding times are also found in patients with Cushing syndrome, severe liver disease, leukemia, and bone marrow failure.

Defects associated with factors of the pathways of blood coagulation can also be assessed with specific assays. The prothrombin time (PT) is an assay designed to screen for defects in fibrinogen, prothrombin, and factors II, V, VII, and X and thus measures activities of the extrinsic pathway of coagulation. When any of these factors is deficient then the PT is prolonged. A normal PT is 11.0-12.5 seconds. A PT greater than 20 seconds is indicative of coagulation deficit. The PT is commonly measured using plasma after the blood cells are removed. A blood sample is typically collected in a tube containing citrate to bind any calcium and thus inhibit coagulation, and then the cells are separated by centrifugation. Excess calcium is added to an aliquot of the plasma to initiate coagulation. The most common measure of PT is to divide the time of coagulation of a patient's blood by that of the mean normal PT value, with this ratio subsequently being raised to a power corresponding to the ISI (international sensitivity index) of the reagent being used. The resulting value is referred to as the international normalized ratio (INR). Normal values range from 0.8-1.2 INR. PT is used to determine the correct dosage of the coumarin class of anti-coagulation drugs (e.g. Coumadin®), for the presence of liver disease or damage, and to evaluate vitamin K status.

The activated partial thromboplastin time (aPTT) is used to assay for defects in the intrinsic pathway of coagulation. The aPTT assay includes the addition of activators that shorten the normal clotting time and is normally prescribed in patients with unexplained bleeding or clotting. The assay will evaluate the function of fibrinogen, prothrombin, and factors V, VIII, IX, X, XI, and XII. A defect in any of these factors will result in a prolonged aPTT. A normal aPTT is is 30-40 seconds. The aPTT is a standard assay used to assess the efficacy of heparin anticoagulant therapy. The aPTT is commonly measured using plasma after the blood cells are removed. A blood sample is typically collected in a tube containing citrate to bind any calcium and thus inhibit coagulation, and then the cells are separated by centrifugation. Excess calcium is added to an aliquot of the plasma to reverse citrate anticoagulation. Prolonged aPTTs are associated with acquired or congenital bleeding disorders associated with coagulation factor deficiency, vitamin K deficiency, liver disease, DIC, von Willebrand disease, leukemia, hemophilia, and during heparin administration.

The activated clotting time (ACT) is a common point-of-care whole-blood clotting test used to monitor high-dose heparin therapy or treatment with bivalirudin. The dose of heparin or bivalirudin required in these settings is beyond the range that can be measured with the aPTT. Typically, whole blood is collected into a tube or cartridge containing a coagulation activator (e.g., celite, kaolin, or glass particles) and a magnetic stir bar, and the time taken for the blood to clot is then measured. The reference value for the ACT typically ranges between 70 and 180 seconds. The desirable range for anticoagulation depends on the indication and the test method used. For example, during cardiopulmonary bypass surgery, the desired ACT range with heparin may exceed 400 to 500 seconds. In contrast, in patients undergoing percutaneous coronary interventions, a target ACT of 200 seconds is advocated when heparin is administered in conjunction with a glycoprotein IIb/IIIa antagonist, whereas an ACT between 250 and 350 seconds is targeted in the absence of such adjunctive therapy.

Electrochemical System for the Determination of Diagnostic Clotting Times

Chromogenic assays have been used to measure the enzymatic activity of specific clotting factors through the development of artificial, cleavable peptide substrates specific for particular factors. It should be noted that assays based on clotting time, such as aPTT, PT and ACT, are essentially functional measures of thrombin formation and inhibition in the presence of anticoagulants, such as warfarin and heparin or defective coagulation factors. Thus, an analogy can be drawn between assays based on the measurement of fibrin formation and assays based directly on the measurement of thrombin activity via the use of appropriate peptide substrates, as in chromogenic assays.

Electrochemical detection involves the use of a working electrode (e.g., an amperometric electrode) and a reference electrode (e.g., a counter reference electrode), whereby a constant potential is applied to the working electrode leading to an oxidation-reduction (redox) reaction that can be quantified as a recordable electric current. Electrochemical sensors have found widespread use in the development of point-of-care (POC) and self-test devices, as exemplified by the development of glucose test strips, as they are simple to interface with electronic instruments and reduce device costs. Devices, such as the i-STAT® system (see, e.g., U.S. Pat. No. 7,977,106, the entirety of which is incorporated herein by reference), have employed electrogenic substrates that result in the formation of an electrochemically detectable cleavage product that is proportional to thrombin activity. These devices are then configured to return a clotting time based on a measure of thrombin activity to allow comparisons with standard clotting. Accordingly, in some embodiments, the electrochemical detection system is termed "electrogenic" because the electrochemically detectable species are generated to allow determination of a rate measurement or a test endpoint, e.g., a diagnostic clotting time. This is similar to the chromogenic or fluorogenic endpoint tests in which a change in the light absorbing or emitting properties of a sample indicates the rate measurement or endpoint, e.g., a diagnostic clotting time.

FIG. 1 illustrates the principle of an electrochemical detection system 10 (e.g., an amperometric electrochemical detection system) according to some embodiments of the present invention for determination of diagnostic clotting times. However, it should be understood that while specific embodiments are described herein for diagnostic clotting time assays (e.g., PT, aPTT, and ACT assays), the micro-environment sensor structures described herein may also be useful for detecting various analytes of potential interest. More specifically, the electrochemical detection system of the present invention is not limited to the assay of coagulation enzymes. For example, any assay where an enzyme cleaves a substrate molecule to yield an electroactive moiety can use the present methodology. As should be understood, assays can be devised for a variety of other known enzymes in the art, such as for example, glucose oxidase, lactate oxidase, and other oxidoreductases, dehydrogenase based enzymes, and alkaline phosphatase and other phosphatases, and serine proteases without departing from scope of the present invention. For example, some aspects of the present invention may include a phosphatase assay where ferrocene with a phosphate moiety is present in a micro-environment sensor layer. The enzyme phosphatase present in a sample may permeate the micro-environment sensor and cleave the phosphate groups enabling the liberated ferrocene molecules to be oxidized at the electrode. Accordingly, the measured current may be a function of the rate of the cleavage reaction, and thus, proportional to the phosphatase activity in the sample.

In an exemplary analysis, a fluidic sample 15, e.g., whole blood, may be introduced into a sample holding chamber 20 of a cartridge 25 of the present invention. Thereafter, the fluidic sample 15 may be introduced to an analysis region 30 of the cartridge, e.g., a sensor region or one or more locations within one or more conduits of the cartridge that includes one or more sensors for coagulation detection and optionally for detection of a target analyte (e.g., thrombin activity for a prothrombin time and troponin I). The analysis region 30 includes one or more micro-environment sensors 35 comprising one or more electrodes or transducers 37, one or more reagents 40, and one or more substrates 45 in any number of different possible arrangements. The form and orientation of the electrodes, reagents, and substrate may vary widely depending on the embodiment of the invention, which are described in detail hereafter.

In accordance with some aspects of the invention, the one or more reagents 40 may include a material for inducing coagulation via the intrinsic or extrinsic pathway. Materials suitable for inducing the extrinsic pathway (e.g., PT analysis) may include one or more components selected from the group consisting of non-recombinant tissue factor, recombinant tissue factor, a synthetic or natural lipid, a synthetic or natural phospholipid, a combination of synthetic or natural lipids, and a combination of synthetic or natural phospholipids. In some embodiments a variety of other components may be included within the one or more reagents 40 to contribute to stabilization and deposition/dissolution characteristics of the one or more reagents 40. For example, the one or more reagents 40 may further comprise one or more components selected from the group consisting of carrier proteins such as bovine serum albumin (BSA), stabilizing agents, antimicrobial agents, a calcium salt, a potassium salt, a water soluble polymer, a sugar, gelatin, agarose, a polysaccharide, a saccharide, sucrose, polyethylene glycol, sodium phosphate, glycine, an amino acid, antioxidants, a detergent, a buffer salt, and a buffer such as 4-(2-hydroxyethyl)-1-piperazineethanesulfonic acid (HEPES) buffer.

In accordance with different aspects of the present invention, the one or more reagents 40 may include material suitable for inducing the intrinsic pathway. Materials suitable for inducing the intrinsic pathway (e.g., the aPTT or ACT analysis) may include one or more components selected from ellagic acid, celite, kaolin, diatomaceous earth, clay, silicon dioxide, synthetic or natural lipids, and synthetic or natural phospholipids. In some embodiments a variety of other components may be included within the one or more reagents 40 to contribute to stabilization and/or deposition/dissolution characteristics of the one or more reagents 40. For example, the one or more reagents 40 may further comprise one or more components selected from the group consisting of dextran, cyclodextrin, dextrin, tergitol, buffers, a carrier protein, an amino acid, stabilizers, antimicrobials, antioxidants, a detergent, a saccharide, a polysaccharide, sucrose, a polyether compound such polyethylene glycol, derivatives of polyethylene glycol, polyethylene oxide or polyoxyethylene, glycine, gelatin, buffer such as 4-(2-hydroxyethyl)-1-piperazineethanesulfonic acid (HEPES) buffer, rhamnose, trehalose, and sugars.

In accordance with some aspects of the present invention, the one or more substrates 45 used in the electrogenic assay may have an amide linkage that mimics the thrombin-cleaved amide linkage in fibrinogen. Specifically, the one or more substrates 45 may comprise one or more thrombin-cleavable peptides such as those selected from the group consisting of H-D-Phe-Pip-Arg, H-D-Chg-Abu-Arg, CBZ-Gly-Pro-Arg, Boc-Val-Pro-Arg, H-D-Phe-Pro-Arg, Cyclohexylglycine-Ala-Arg, Tos-Gly-Pro-Arg, Bz-Phe-Val-Arg, Boc-Val-Pro-Arg, Ac-Val-Pro-Arg, Ac-Val-Hyp-Arg, Ac-(8-amino-3,6,dioxaoctanoyl-Val-Pro-Arg, Ac-Gly-Pro-Arg, Ac-(8-amino-3,6,dioxaoctanoyl-Gly-Pro-Arg, Ac-Gly-Hyp-Arg and H-D-Chg-Abu-Arg. Thrombin typically cleaves the amide bond at the carboxy-terminus of the arginine residue because the bond structurally resembles the thrombin-cleaved amide linkage in fibrinogen. The product of the thrombin-substrate reaction includes electrochemically inert compounds such as Tos-Gly-Pro-Arg, H-D-Phe-Pip-Arg, and/or Bz-Phe-Val-Arg- and electroactive compounds or detectable moieties, preferably selected from the group consisting of p-aminophenol, a quinone, a ferrocene, ferrocyanide derivative, other organometallic species, p-nitroaniline, o-dianisidine, 4,4'-bensidine, 4-methoxy-2-naphthylamine, N-phenyl-p-phenylenediamine, N-[p-methoxyphenyl-]-p-phenylenediamine, and phenazine derivatives. The tripeptide sequence was chosen because it renders the substrate virtually non-reactive with blood proteases other than thrombin and the reactivity of thrombin with the arginine amide linkage in the molecule is very similar to its reactivity with the target amide linkage in fibrinogen. When the one or more substrates 45 are present in a blood or blood derivative fluid sample or biological sample, generated active thrombin from activation of the coagulation pathway(s) via the one or more reagents 40 simultaneously converts the one or more substrates 45 and fibrinogen to their cleavage products. The electrochemical species reaction product is detected by the one or more transducers 37, e.g., an electrochemical transducer.

Micro-Environment Sensor Structures

As discussed herein, micro-environment sensor structures comprise one or more reagents and one or more substrates in any of a number of different arrangements such that the introduction of the fluid sample, e.g., whole blood, to the one or more reagents and the one or more substrates is localized to the one or more sensors. In particular, the micro-environment sensor structures are configured to physically separate the one or more reagents and/or reaction products from one another to avoid cross-activation of the cascade pathways or other cross-sensor interference once the one or more reagents have become exposed to the fluid sample.

Figure 2:
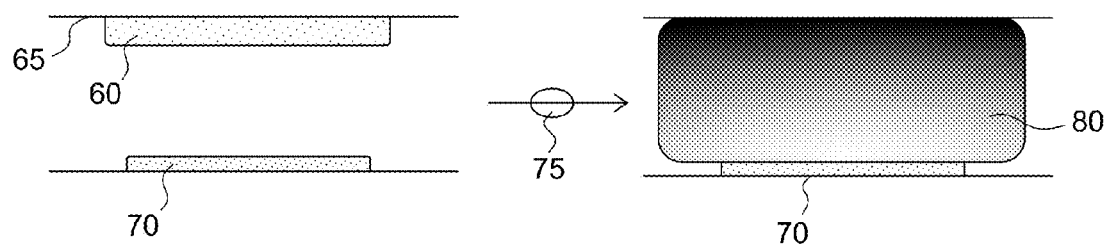
FIGS. 2 and 3 show a conduit comprising a dissolvable reagent/substrate and transducer in accordance with some aspects of the invention.

As shown in FIG. 2, traditional POC coagulation assays have employed the reagent/substrate 60 printed as a dry substance on a wall 65 (e.g., a cover) of a conduit that is opposite a surface of a sensor 70. The fluid sample 75 would need to be mixed with the dry substance, e.g., by pump oscillation, to dissolve the reagent/substrate 60 into the fluid sample 75 and generate a mixture 80, which may be in the form of a gradient from a top of the conduit down to the sensor 70. However, such a configuration has at least three issues or disadvantages. Firstly, only a small portion of the electroactive product generated via mixture 80 will reach the surface of the sensor 70 and be oxidized, and thus a majority of the electroactive product will not be utilized. As a result, the usage of the reagent/substrate 60 is not efficient. Further, the fluid sample 75 is adulterated with the reagent/substrate 60, which may be undesirable due to its possible impact with other sensors that may come in contact with the fluid sample 75 (e.g., cross-sensor interference). Secondly, in order to achieve adequate analytical precision, the reagent/substrate 60 should be dispersed uniformly in the fluid sample 75 as rapidly as possible. This may be a challenge for point-of-care devices where space and efficiency of mixing can be limited. It is especially true when the reagent/substrate 60 is in solid form and in a very small space relative to a volume of the fluid sample 75. Thirdly, there is a possibility that the substrate interferes with the reagent and/or coagulation factors. For example, mixing the substrate along with the reagent into the sample 75 before the coagulation cascade has been initiated may manifest such interference.

Figure 3:
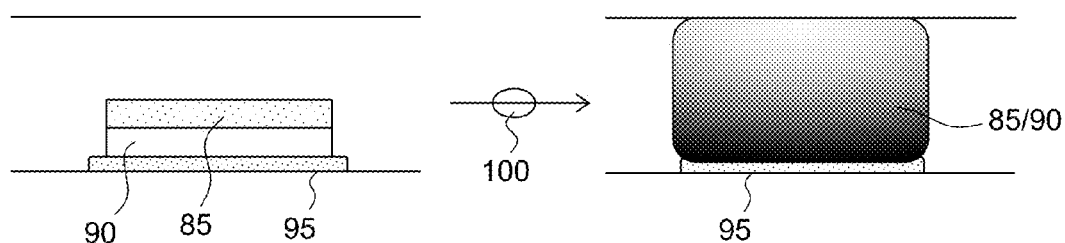

In contrast to the traditional POC coagulation assays, some embodiments of the present invention, as shown in FIG. 3, present the reagent 85 associated with a substrate layer 90 formed in a localized manner near the surface of the sensor 95. For example, as shown in FIG. 3, the reagent 85 and the substrate 90 may be printed as a dry substance directly on a surface of the sensor 95. The fluid sample 100 may react with the reagent 85 and the substrate 90 without mixing (e.g., via passive diffusion) (although some degree of mixing, e.g., fluid oscillation, may be desired), in a localized manner creating a gradient from the sensor 95 to a top of the conduit. Advantageously, this arrangement of the reagent and the substrate presented directly on a surface of the sensor allows for a majority of the electroactive product to be oxidized, and thus utilized at the surface of the sensor. This sensor arrangement is also beneficial due to the smaller sample volume required in the immediate sensor environment, and thus yielding a more concentrated reagent-to-sample assay zone.

Nonetheless, some of the issues (e.g., mitigation of cross-sensor interference and substrate interference) apparent within the traditional POC coagulation assays may not be overcome by the arrangement shown in FIG. 3. For example, any reaction occurring in the immediate vicinity of the sensor could potentially interfere with the reagent and/or coagulation factors and/or possibly with another reaction occurring at an adjacent sensor (i.e., a sensor within the same conduit and within approximately 3 mm of the sensor shown in FIG. 3). As such, this type of sensor arrangement would not be characterized as a micro-environment sensor. However, these remaining issues may be overcome via advanced micro-fluidic systems of the present invention (e.g., splitting a single sample into two or more parts and controlling movement of those parts into two or more conduits or conduits), as discussed hereafter in detail, and/or appropriate spacing of sensors from one another. For example, in some embodiments, where adjacent sensors are covered by a same quiescent sample fluid, to prevent cross-sensor interference below a given threshold, e.g., below 1%, it may be suitable to use models based on a known diffusion coefficient for the interferent and the overall assay time to determine an appropriate separation distance between sensors. In other embodiments, where the sample is non-quiescent, other models for dynamic mixing may be suitable for use to select an appropriate sensor separation distance.

Figure 4:
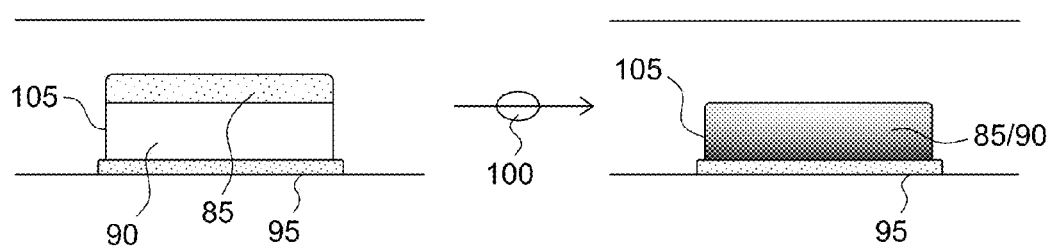
FIG. 4 shows a diffusible reagent, immobilized substrate-polymer layer, and transducer in accordance with some aspects of the present invention.

In additional or alternative embodiments, immobilizing the substrate 90 on the sensor 95 has been unexpectedly demonstrated to address many or all of the above-mentioned issues. In accordance with these aspects of the present invention, the immobilization may be realized by crosslinking (e.g., ultra-violet light, glutaraldehyde, etc.), entrapment, covalent binding, etc. One example of such a micro-environment arrangement is shown in FIG. 4 where the substrate 90 is immobilized on the surface of the sensor 95 using a polymer layer 105. In some embodiments, the immobilization may be performed by coating the sensor 95 with a polymer layer 105 that includes the substrate 90 such that the substrate 90 is immobilized via the polymer layer 105 on the surface of the sensor 95. In other words, the substrate 90 is formed as an immobilized porous substrate-polymer layer on the surface of the sensor 95 to create a vessel for maintaining the reaction of the fluid sample 100, the reagent 85, and the substrate 90 in a localized manner on a surface of the sensor 95. The fluid sample 100 may react with the reagent 85 and the substrate 90 without mixing (although some degree of mixing, e.g., fluid oscillation, may be desired) in a localized manner within the confines of (or above, and then diffused into) the polymer layer 105 formed on the sensor.

Advantageously, this arrangement of the immobilized substrate presented directly on a surface of the sensor allows for a majority of the electroactive product to be oxidized, and thus utilized at the surface of the sensor. Even more advantageously, this arrangement of the immobilized substrate provides for a micro-environment capable of maintaining the substrate and the electroactive product in the immediate vicinity of the sensor, and thus mitigating cross-sensor interference with an adjacent sensor during normal usage. Other potential benefits of immobilizing the substrate on the sensor include mitigation of substrate interference via separation of the substrate from the reagent, reduction of material use, simplification of hardware and sensor design, and improvement of product robustness.

Figure 5:
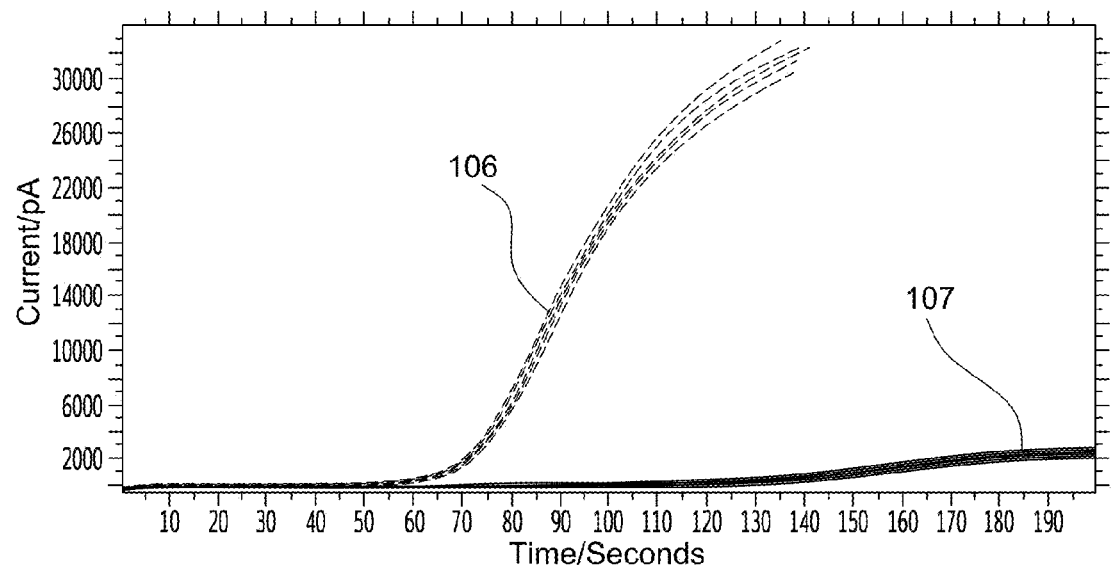
FIGS. 5 and 6 show graphs that provide empirical evidence for aspects of the present invention.
Figure 6:
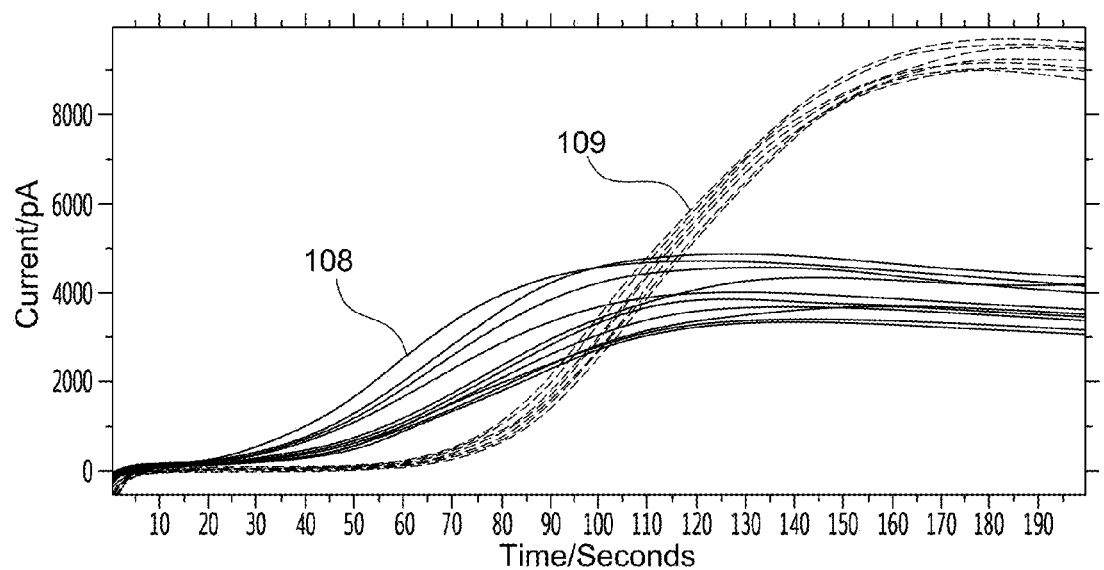

FIGS. 5 and 6 provide empirical evidence that immobilizing the substrate can increase the response current and improve precision of analyte detection significantly. Specifically, FIG. 5 shows aPTT response curves where the x-axis is time/seconds and the y-axis is current/pA. In this example, the substrate was printed on a sensor, one immobilized with PVA (aPTT response curves 106) and the other not immobilized (aPTT response curves 107). An aPTT reagent was spiked into the whole blood. After mixing for about 30 seconds the sample was drawn from the sample tube and filled into cartridges for testing. The electric current of the immobilized substrate sensor (aPTT response curves 106) was over 30 nA, whereas that of the non-immobilized substrate sensor (aPTT response curves 107) was only about 3 nA. Their coefficient of variations of tMid (time at which the current reaches its middle point) were about 1% and 2%, respectively. This data indicates that the presence of the immobilized substrate directly over the sensor enabled the immediate and concentrated redox reaction from the coagulation substrate leaving group. This in turn yielded faster clotting times and a more predictable sensor response.

Another example is shown in FIG. 6 where the x-axis is time/seconds and the y-axis is current/pA. The PT response curves 108 represent the response of a non-immobilized substrate sensor to an i-STAT® PT control fluid level 2, whereas the PT response curves 109 represent the response of an immobilized substrate sensor to the same i-STAT® PT control fluid level 2. With respect to the non-immobilized substrate sensor, both the substrate and the reagent were printed together on the electrode, and mixed together with the sample during testing. With respect to the immobilized substrate sensor, the substrate was immobilized with PVA on the electrode and the reagent was printed on top of the immobilized substrate, and there was no mixing during test. Use of the immobilized sensor with a plasma control yielded a significant improvement in performance such that the electric current increased from about 4 nA to about 9 nA, and the coefficient of variation decreased from around 10% to about 3%. This data shows a significant improvement in the field of coagulation testing such that performance of a point of care device could now approach the performance of a central laboratory instrument (2-3% CV).

Figure 7A:
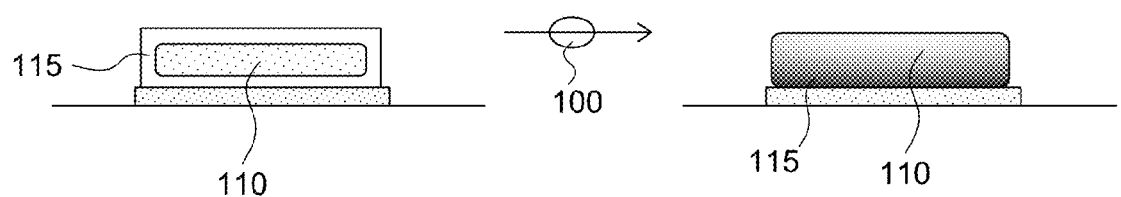
FIGS. 7A, 7B, and 7C illustrate the principle of operation of the microenvironment sensor comprising a reagent and/or substrate, immobilized or not in a polymer layer, and transducer in accordance with some aspects of the invention.
Figure 7B:
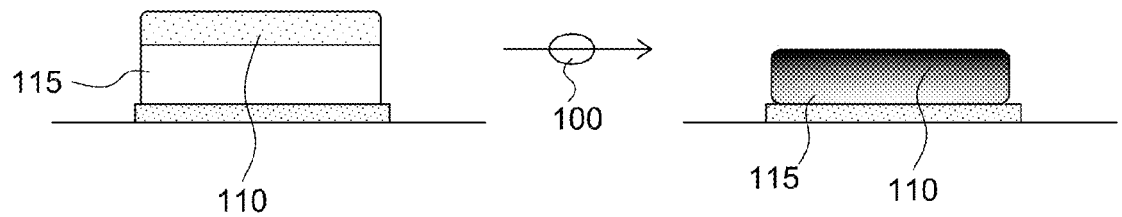
Figure 7C:
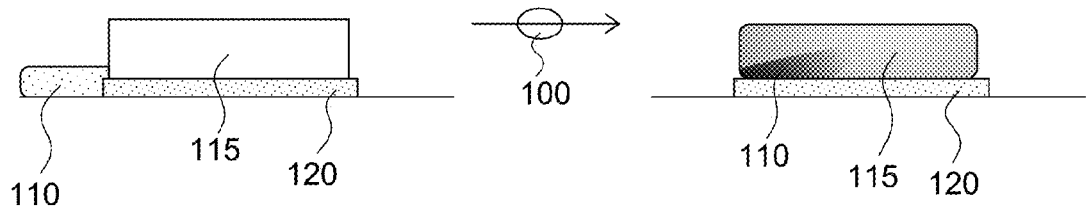

As shown in FIGS. 7A, 7B, and 7C, the micro-environment sensors of the present invention may have the reagent 110 and the immobilized substrate-polymer layer 115 positioned in a number of different arrangements with the components interacting with each other without mixing, although some degree of oscillation may be desired. For example, as shown in FIG. 7A, the reagent 110 may be positioned within or encapsulated by the immobilized substrate-polymer layer 115 (e.g., the reagent is integrated within the immobilized substrate-polymer layer). As shown in FIG. 7B, the reagent 110 may be coated over the immobilized substrate-polymer layer 115 (e.g., the reagent is a separate layer dispensed on top of the immobilized substrate-polymer layer). As shown in FIG. 7C, the reagent 110 may be positioned substantially adjacent to the immobilized substrate-polymer layer 115 and at least one transducer of the sensor 120 (e.g., the reagent is positioned within the conduit such that the reagent is abutted to or within an interactive distance of the substrate-polymer layer and/or the at least one transducer so as to still function in conjunction with each other). As used herein, an interactive distance means less than a longest dimension of the sensor with the constraint of the reagent being positioned within a same plane or on a same wall/surface of a conduit as the sensor. Other variants will also be apparent to those skilled in the art without departing from the spirit and scope of the present invention, for example the reagent 110 may be formed as a combination of that shown in FIGS. 7B and 7C, or as shown in FIG. 7C with only part of the reagent 110 shown in FIG. 7B.

Figure 8:
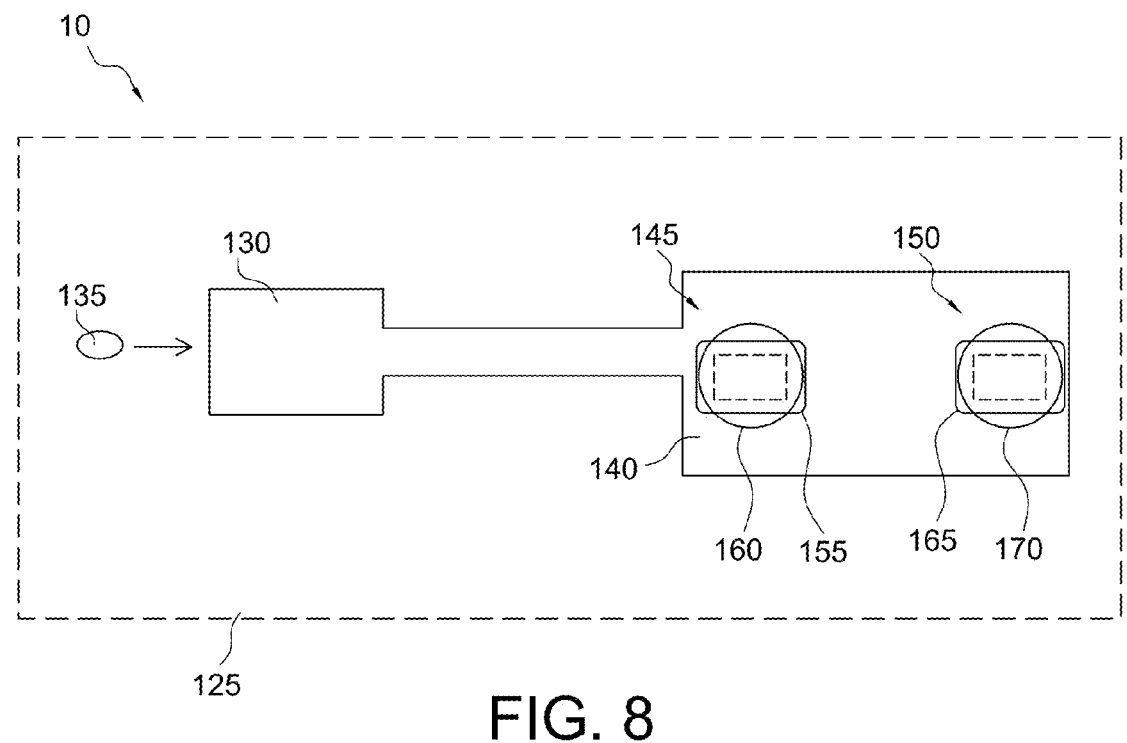
FIG. 8 shows a cartridge schematic in accordance with some aspects of the invention.

As shown in FIG. 8, in some embodiments, the present invention may be directed to an analysis cartridge 125 comprising an inlet chamber 130 configured to receive a fluid sample 135 and a conduit 140 fluidically connected to the inlet chamber 130 and configured to receive the fluid sample 135 from the inlet chamber 130. The conduit 140 may comprise an array of micro-environment sensors, e.g., a first micro-environment sensor 145 and a second micro-environment sensor 150. The first micro-environment sensor 145 may comprise a first reagent 155 and a first substrate 160 (e.g., a substrate immobilized within a polymer layer) configured to detect a first diagnostic clotting time. For example, the first micro-environment sensor 145 may be a PT sensor comprising a first reagent 155 that includes one or more components, as discussed herein, specific for triggering the extrinsic coagulation pathway and a first substrate layer 160 comprising a thrombin-cleavable peptide with a detectable moiety as discussed herein. The second micro-environment sensor 150 may comprise a second reagent 165 and a second substrate 170 (e.g., a substrate immobilized within a polymer layer) configured to detect a second diagnostic clotting time. For example, the second micro-environment sensor 150 may be an aPTT sensor comprising a second reagent 165 that includes one or more components, as discussed herein, specific for triggering the intrinsic coagulation pathway and a second substrate layer 170 comprising a thrombin-cleavable peptide with a detectable moiety (e.g., a reagent and a substrate immobilized within a polymer layer). As should be understood, although the above-described analysis cartridge 125 is discussed with respect to a PT sensor and an aPTT sensor, various combinations and numbers of sensors, e.g., a PT sensor, an aPTT sensor, and an ACT sensor, are contemplated by the present invention without departing from the scope of the present invention. For example, the first micro-environment sensor 145 may be a PT sensor, and the second micro-environment sensor 150 may be an aPTT sensor or an ACT sensor. In another aspect, the first micro-environment sensor 145 is an aPTT sensor, and the second micro-environment sensor 150 is a PT sensor or an ACT sensor. In another aspect, the first micro-environment sensor 145 is an ACT sensor, and the second micro-environment sensor 150 may be an aPTT sensor or a PT sensor. In still other embodiments, one of the micro-environment sensors is a PT sensor, an aPTT sensor, or an ACT sensor, and another of the sensors is a sensor for detecting an analyte, related or unrelated to coagulation.

Advantageously, the micro-environment sensor structures of the present invention are configured to physically separate the one or more reagents and substrates to avoid cross-activation and/or interference of the cascade pathways once the one or more reagents and substrates have become exposed to the fluid sample. Even more advantageously, incorporation of the immobilized substrate and/or reagent polymer layer into the coagulation assays provides for the ability to perform the coagulation assays without requiring or while minimizing mixing, e.g., oscillation of the sample fluid in a conduit, because coagulation activation occurs in a localized and concentrated area over the sensor with subsequent propagation of the test reaction into the immobilized layer, ultimately resulting in oxidation at the transducer.

Immobilized Substrate-Polymer Layer

Figure 9:
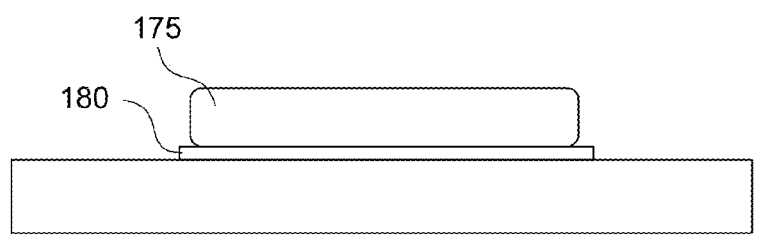
FIG. 9 shows a side view of the fabrication of an immobilized reagent/substrate-polymer layer in accordance with some aspects of the invention.

In preferred embodiments, in order to physically separate the one or more assays from one another to avoid cross-activation and promote localization of electrochemical or optical signals over the transducers, an immobilized substrate and/or reagent-polymer layer may be selectively patterned onto the sensors (e.g., coated over the transducer or working electrode/optical detector). As shown in FIG. 9, the immobilized polymer layer 175 may be formed by either spin coating or by microdispensing. More specifically, an aqueous polymer matrix comprising one or more reagents and substrates and a polymer, such as a photoformable polymer (e.g., polyvinylalcohol (PVA)), may be utilized for immobilizing the one or more substrates on or near the transducer 180. Additives including but not limited to a protein such as BSA, a sugar or sugar alcohol, such as sucrose, sorbitol, or mannitol, may also be included in the aqueous matrix. To those skilled in the art of polymer chemistry, the addition of some substances to the polymer layer(s) results in a number of alterations to, including but not limited to, swelling reactions, diffusion coefficients, molecule stability, porosity, transport, reaction kinetics and the like. These alterations can be used to modulate the micro-environment sensor response as required.

In accordance with some aspects of the invention, the one or more substrates may comprise one or more thrombin-cleavable peptides selected from the group consisting of H-D-Phe-Pip-Arg, H-D-Chg-Abu-Arg, CBZ-Gly-Pro-Arg, Boc-Val-Pro-Arg, H-D-Phe-Pro-Arg, Cyclohexylglycine-Ala-Arg, Tos-Gly-Pro-Arg, Bz-Phe-Val-Arg, Boc-Val-Pro-Arg, Ac-Val-Pro-Arg, Ac-Val-Hyp-Arg, Ac-(8-amino-3,6, dioxaoctanoyl-Val-Pro-Arg, Ac-Gly-Pro-Arg, Ac-(8-amino-3,6,dioxaoctanoyl-Gly-Pro-Arg, Ac-Gly-Hyp-Arg and H-D-Chg-Abu-Arg. Optionally the two or more of these substrates may be mixed to obtain the thrombin activities and diffusional properties desired in the immobilized substrate and/or reagent polymer layer.

In accordance with some aspects of the invention, the polymer that contains the substrate may comprise one or more materials, optionally in matrix form. The material for the polymer, for example, may be selected from the group consisting of PVA, styrylpyridinium polyvinylalcohol (SBQ-PVA), agarose, polyacrylamide, polymethyl methacrylate, N-methylpyrrolidone, polyvinylpyrrolidone, polyimide, a film-forming latex, sepharose, polyurethanes, acrylates, methacrylates, polyethylene glycols, polylactic acid, poly(lactic co-glycolic acid), hydroxypropyl cellulose, celluloses, derivatives of cellulose, hydroxypropylmethylcellulose acetate succinate, inulin, fructans, derivatives of fructans, polyglycolic acid, Elvace, carboxymethyl cellulose, polylactic acid, and poly(lactic co-glycolic acid). In some embodiments in which the material for the polymer comprises celluloses (e.g., hydroxypropyl cellulose), additives such as a plasticizer (e.g., triethyl citrate, acetyl triethyl citrate, propylene glycol, glycerin, trimethylolpropane, polyethylene glycols, fatty acids, and derivatives thereof) and/or crosslinkers (e.g., carboxylic acids, glyoxal, and any resin which is reactive with the available hydroxyl groups of the cellulose) may also be included in the aqueous matrix. Crosslinking of the materials may also affect the polymer layer swelling, permeability, diffusion, reaction kinetics etc. in order to modulate the sensor response as required.

Further to selection of the material for the polymer, another benefit of immobilizing the substrate and/or reagent includes using the immobilizing matrix as a localized interferant neutralizer. For example, the selection of the material for the polymer may be dependent upon the type of diagnostic clotting test to be performed using the immobilized polymer layer. For example, advantageously and unexpectedly it has been found that inclusion of cross-linked or non-cross-linked SBQ-PVA in the immobilized polymer layer imparts a heparin neutralizing property or heparin insensitivity into the immobilized polymer layer. Consequently, in embodiments in which the diagnostic clotting test to be performed using the immobilized polymer layer is a heparin sensitive test (e.g., the PT test is known to be moderately sensitive to clot inhibitors such as heparin), the polymer may be selected to be a heparin-neutralizing polymer such as cross-linked or non-cross-linked SBQ-PVA. In some embodiments, the PVA may be a photo-activated stilbizonium salt.

Figure 10:
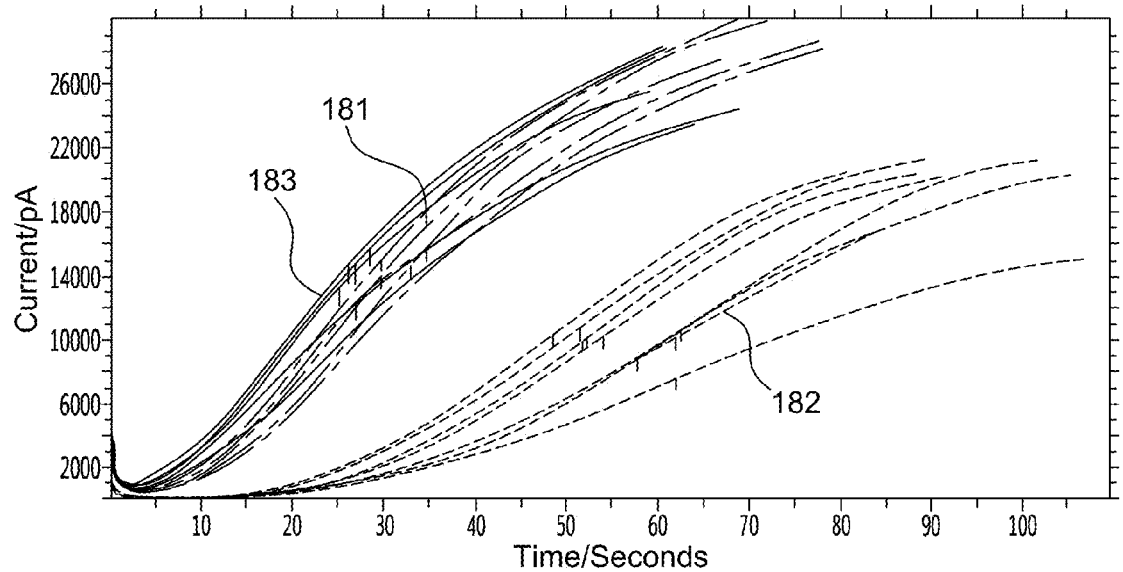
FIGS. 10-12 show graphs that provide empirical evidence for aspects of the present invention.
Figure 11:
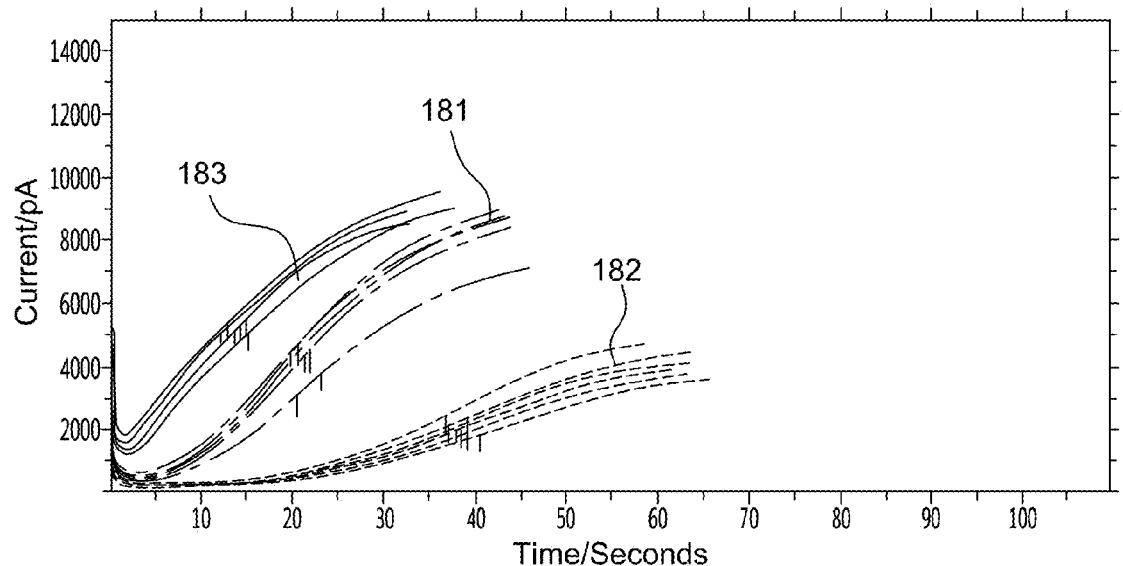

FIGS. 10 and 11 exemplify this concept as follows. A coagulation sensor was directly printed either with a large (FIG. 10) or small (FIG. 11) SBQ-PVA immobilized coagulation substrate. Subsequently, a PT coagulation activator was printed on top of the immobilized substrate matrix. These sensors were then tested with appropriate fluids to assess coagulation time. As with the results from FIGS. 5 and 6, one benefit of printing more of the immobilized substrate matrix is that the increased amount of immobilized substrate matrix led to an increase in pA. Also, when heparin is spiked into the whole blood sample, the clotting times are not as extended as they are expected to be (FIGS. 10 and 11 (response curves 181) (heparin spike) should be more similar to response curves 182 (abnormally long control fluid) clotting times, but are actually behaving more like whole blood without heparin, (response curves 183)). These results reflect the heparin neutralizing effect of a polymer such as SBQ-PVA. Further, applying a larger amount of the immobilizing matrix results in a greater neutralizing effect (e.g., compare the bias between whole blood and whole blood with heparin in FIGS. 10 and 11). FIG. 10 data represents a large matrix print and shows that there is 14% extension when heparin is added to 1 IU/mL, while in FIG. 11 there is 55% extension when a smaller print amount of the neutralizing matrix is deposited. In both FIGS. 10 and 11, the heparin spiked blood behaves more like unaltered whole blood than it does like an abnormally long control fluid, reflecting that there is an interferent/heparin neutralizing effect. This data shows that increasing the area of the PVA print reduces the interferent effect of the heparin to the PT assay.

Figure 12:
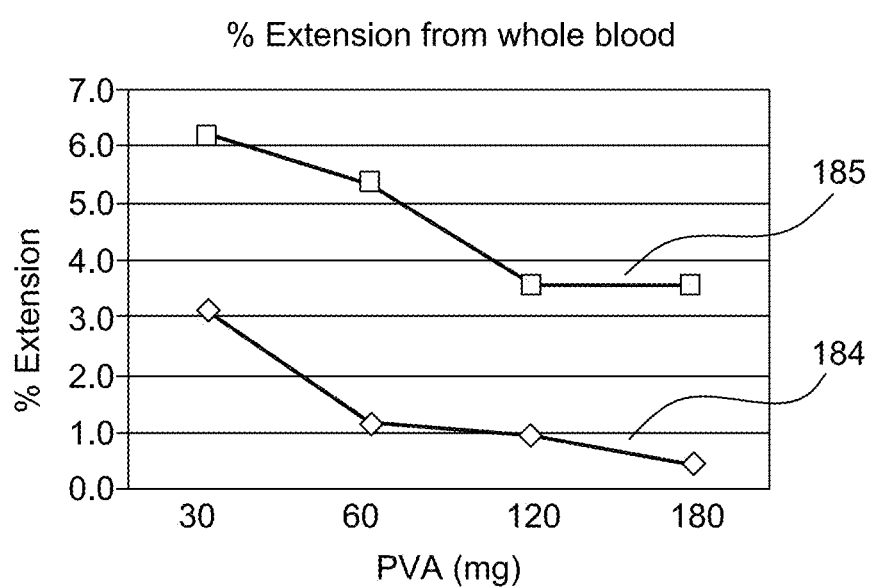

FIG. 12 provides further empirical evidence that a cross-linked SBQ-PVA may be used to impart a heparin neutralizing property or heparin insensitivity to an immobilized substrate PT assay. Specifically, FIG. 12 shows results of a PT assay performed on a whole blood sample (response curve 184) and a whole blood sample (response curve 185) spiked with 0.4 (response curve 184) or 1.2 IU/ml (response curve 185) of heparin without use of heparinase (a reagent conventionally included in a PT test for neutralizing heparin), but with the addition of increasing amounts of SBQ-PVA to the same size print. The data shows that increasing the concentration of the SBQ-PVA layer results in the lowering of the clotting time extensions from whole blood in the presence of heparin. This shows that the PT microenvironment sensor response can be modulated to reduce interference of heparin without the use of expensive heparinase.

Without being bound by theory, it appears that a positive charge imparted by the cross-linked or non-cross-linked SBQ-PVA may impart the heparin neutralizing property or heparin insensitivity to the immobilized substrate PT assay. More particularly, the SBQ pendent group is a cation, the PVA is an anion, and the heparin is an anion, and thus it is hypothesized that repulsion in the localized area of the electrode via the positively charged SBQ excludes heparin from the immobilized sensor micro-environment or the positively charged SBQ interacts with the negatively charged heparin and incapacitates the ability of heparin to act on coagulation factors. This theory is further evidenced by the fact that an anionic polymer such as hydroxypropyl cellulose may be used for diagnostic clotting time tests that monitor heparin therapy (e.g., aPTT and ACT) without imparting a heparin neutralizing property or heparin insensitivity to the assay.

In additional or alternative embodiments, the polymer may be a non-heparin neutralizing polymer that could then be subsequently treated or modified to become heparin neutralizing. For example, in embodiments in which the diagnostic clotting test to be performed using the immobilized polymer layer is heparin sensitive, the polymer may be selected to include at least one non-heparin neutralizing component, for example, selected from the group consisting of hydroxypropyl cellulose, and Elvace, carboxymethyl cellulose, polylactic acid, polylactic acid, poly(lactic co-glycolic acid), celluloses, derivatives of cellulose, hydroxypropylmethylcellulose acetate succinate, inulin, fructose, fructans, derivatives of fructans, and polyglycolic acid. The one or more components of the non-heparin neutralizing polymer may then be treated or modified to generate a heparin neutralizing layer. In some embodiments, the treatment or modification may include changing the charge of the one or more components of the non-heparin neutralizing polymer, adding heparinase to the polymer matrix, and/or configuring the polymer layer to preferentially bind sulfate groups on the heparin.

In additional or alternative embodiments, the polymer may be formed of a non-heparin neutralizing polymer. For example, in embodiments in which the diagnostic clotting test to be performed using the immobilized polymer layer is for monitoring heparin therapy (e.g., the aPTT and ACT test), the polymer layer may include at least one non-heparin neutralizing component optionally selected from the group consisting of hydroxypropyl cellulose, Elvace, carboxymethyl cellulose, polylactic acid, polylactic acid, poly(lactic co-glycolic acid), celluloses, derivatives of cellulose, hydroxypropylmethylcellulose acetate succinate, inulin, fructans, derivatives of fructans, and polyglycolic acid.

In embodiments comprising spin coating, the immobilized substrate and/or reagent polymer layer may be photolithographically patterned using ultraviolet light to crosslink the material using a mask followed by removal of the non-crosslinked material such that the immobilized substrate and/or reagent polymer layer is selectively coated. In embodiments comprising microdispensing (See, for example, U.S. Pat. No. 5,554,339, which is incorporated herein by reference in its entirety), an appropriate quantity of each coating may be applied to an area optionally circumscribed by an additional structural component configured as a containment boundary. Alternatively, surfaces treatments, e.g., exposure to gas plasmas, may be used to control the surface energy, and thus the spreading of the microdispensed material.

Figure 13A:
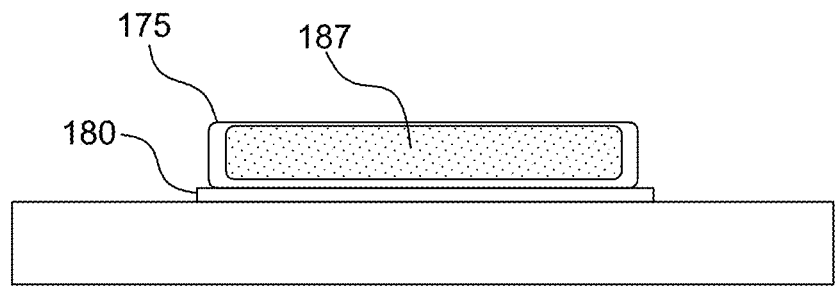
FIGS. 13A, 13B, and 13C show multiple arrangements for a diffusible reagent, immobilized substrate-polymer layer, and transducer in accordance with some aspects of the invention.

In some embodiments, the one or more reagents and substrates 187 may be immobilized within the polymer layer 175 as shown in FIG. 13A. In accordance with these aspects of the present invention, the aqueous substrate-polymerreagent matrix comprising one or more substrates, a polymer such as photoformable polymer (e.g., PVA), and one or more reagents may be utilized for immobilizing the one or more substrates and the one or more reagents on or near the transducer 180. The immobilized polymer layer 175 may be formed by either spin coating or by microdispensing the aqueous substrate-polymer-reagent matrix. In preferred embodiments, the one or more reagents or substrates 187 for an aPTT or ACT test may be immobilized within the polymer layer 175 and the dried volume of the immobilized reagent-substrate-polymer layer 175 comprising the one or more reagents or substrates 187 may be in the range of about 0.55-2.0 nL, preferably in the range of about 1.0-1.5 nL. In some embodiments, the immobilized polymer layer 175 is substantially planar and has a thickness in the range of about 0.1-100 µm. In additional or alternative embodiments, the immobilized polymer layer 175 is substantially domed and has a maximum thickness of the dome in the range of about 0.1-100 µm. Although the reagents are shown in FIG. 13A heterogeneously localized in the central region of the polymer layer 175, in preferable embodiments the reagent(s) is homogeneously dispersed throughout the substrate-polymer layer.

Figure 13B:
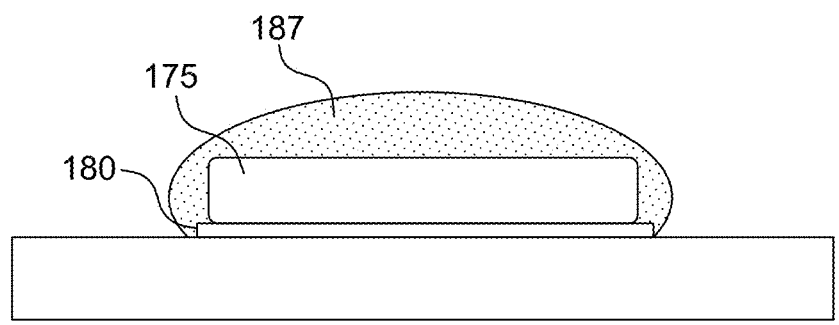
Figure 13C:
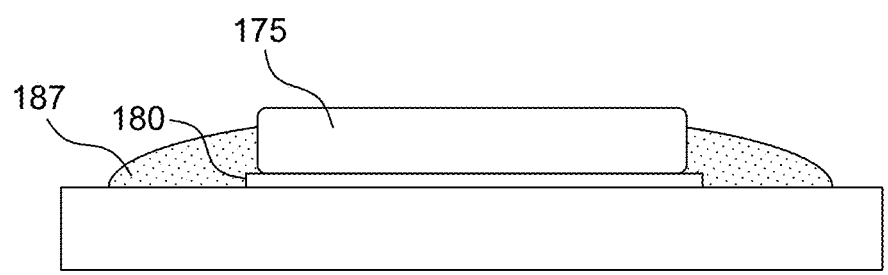

In some embodiments, the one or more reagents or substrates 187 may be formed as a separate layer over and/or adjacent to the immobilized polymer layer 175 as shown in FIGS. 13B and 13C. Further, the one or more regents or substrates may be localized/immobilized together or in separate locations. In accordance with these aspects of the present invention, the one or more reagents or substrates 187 may be spin coated or printed over and/or adjacent to the immobilized polymer layer 175 (e.g., the PVA layer) to localize electrochemical or optical signals over or near the transducer 180. In preferred embodiments, the one or more reagents or substrates 187 for a PT test may be formed separate from the immobilized polymer layer 175 and the dried volume of the immobilized polymer layer 175 may be in the range of 1.5-2.2 nL, preferably in the range of 1.60-2.00 nL. In some embodiments, the immobilized polymer layer 175 is substantially planar and has a thickness in the range of about 0.1-100 µm. In additional or alternative embodiments, the immobilized polymer layer 175 is substantially domed and has a maximum thickness of the dome in the range of about 0.1-100 µm.

Sensor and Chip Design

A preferred embodiment of a microfabricated sensor array comprises at least one transducer (e.g., a working electrode or optical detector). For example, the microfabricated sensor array may comprise a pair of micro-environment sensors or transducers comprising a first micro-environment sensor or transducer (e.g., a PT sensor) and optionally a second micro-environment sensor or transducer (e.g., an aPTT sensor). In some embodiments, the micro-environment sensors or transducers may be fabricated as adjacent structures, respectively, on a silicon chip.

In additional or alternative embodiments, the microfabricated sensor array may further comprise in addition to the first micro-environment sensor or transducer and optionally the second micro-environment sensor or transducer, one or more blood chemistry sensors. For example, the sensor array may further comprise one or more of sensors configured to measure one or more of sodium, potassium, calcium, chloride, carbon dioxide, glucose, blood urea nitrogen (BUN), creatinine, pH, partial pressure $CO_2$, partial pressure $O_2$, lactate, magnesium, or another analyte.

Figure 14:
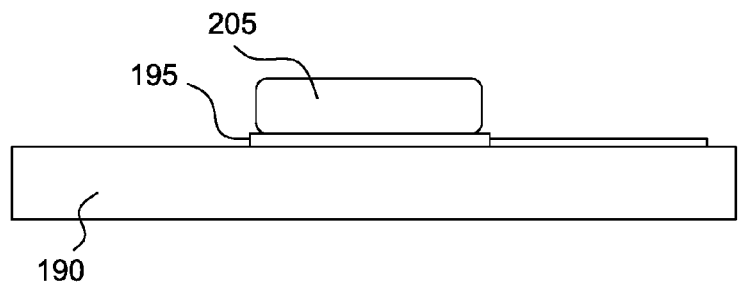
FIG. 14 shows a side view of the fabrication of a sensor in accordance with some aspects of the invention.

In some embodiments, the transducers may be formed as electrodes with gold surfaces coated with a photo defined polyimide layer. For example, wafer-level micro-fabrication of a preferred embodiment of the sensor array may be achieved as shown in FIG. 14. A planar non-conducting substrate 190 may be used as a base for the sensor array. A conducting layer 195 may be deposited on the substrate 190 by conventional means, e.g., conductive printing, or micro-fabrication technique known to those of skill in the art to form at least one transistor. The conducting layer 195 may comprise a noble metal such as gold, platinum, silver, palladium, iridium, or alloys thereof, although other unreactive metals such as titanium and tungsten or alloys thereof may also be used, as many non-metallic electrodes of graphite, conductive polymer, or other materials may also be used.

For example, a base electrode may comprise a square array of 5-10 µm gold disks, e.g., 7 µm gold disks, on 15 µm centers. The array may cover a region, e.g., a circular region, approximately 300 to 900 µm in diameter, optionally 400-800 µm or about 600 µm in diameter, and may be formed by photo-patterning a thin layer of polyimide or photoresist of thickness up to 1.5 µm over a substrate made from a series of layers comprising Si,$SiO_2$,TiW, and/or Au, or combinations thereof. In some embodiments, the base electrode has a working area of about 130,000 to 300,000 sq µm, the volume of sample directly over the sensor may be about 0.1-0.3 µL, and the volume of the sample over the chip may be 1-3 µL. In accordance with these aspects of the present invention, the conduit in a region of the base electrode has a volume to sensor area ratio of less than about 6 µL to about 1 square mm, preferably less than about 50 mm to about 2 square mm, more preferably less than about 100 µm to about 500 square µm. Accordingly, the array of microelectrodes affords high collection efficiency of a detectable moiety that is an electroactive species with a reduced contribution from any electrochemical background current associated with the capacitance of the exposed metal. In particular, openings in the insulating polyimide or photoresist layer define a region of gold electrodes at which the electroactive species, e.g., p-aminophenol, may be oxidized such as in a two electron per molecule reaction.

Micro-fabrication techniques (e.g. photolithography and plasma deposition) may be utilized for construction of the multilayered sensor structures in confined spaces. For example, methods for micro-fabrication of electrochemical immunosensors on silicon substrates are disclosed in U.S. Pat. No. 5,200,051, which is hereby incorporated by reference in its entirety, and include, for example, dispensing methods, methods for attaching substrates and reagents to surfaces including photoformed layers, and methods for performing electrochemical assays.

The microfabricated sensor array may also comprise an electrical connection 195 and an immobilized polymer layer 205 (as discussed above with respect to FIGS. 4, 7A, 7B, and 7C), which is deposited onto at least a portion of the conducting layer 195 and/or the non-conducting substrate 190. In the present invention, the immobilized polymer layer 205 may be a porous polymer layer comprising a thrombin-cleavable peptide with a detectable moiety that is configured to respond to the presence of active thrombin by producing a change that is capable of being measured.

Figure 15:
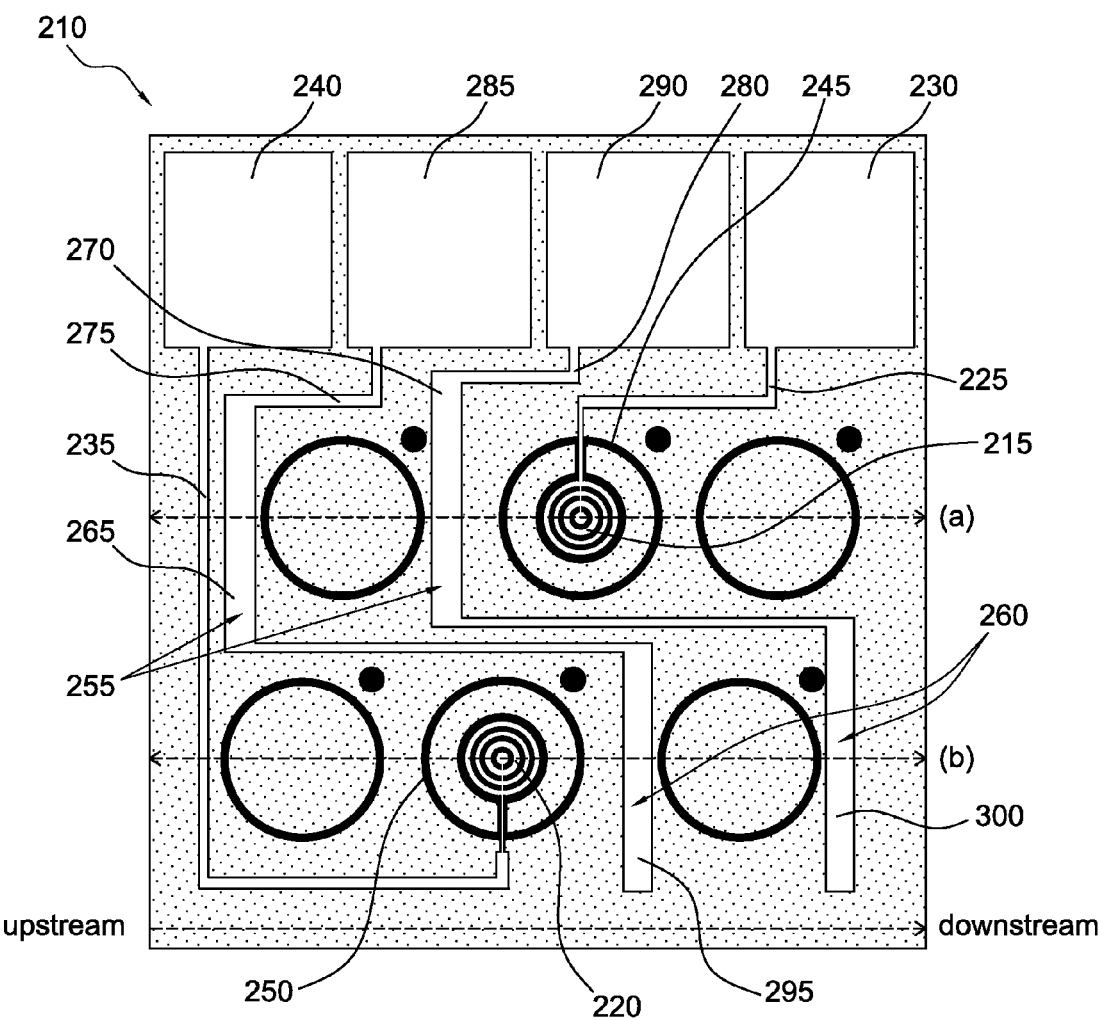
FIGS. 15 and 16 show multiple sensor configurations in accordance with some aspects of the invention.
Figure 16:
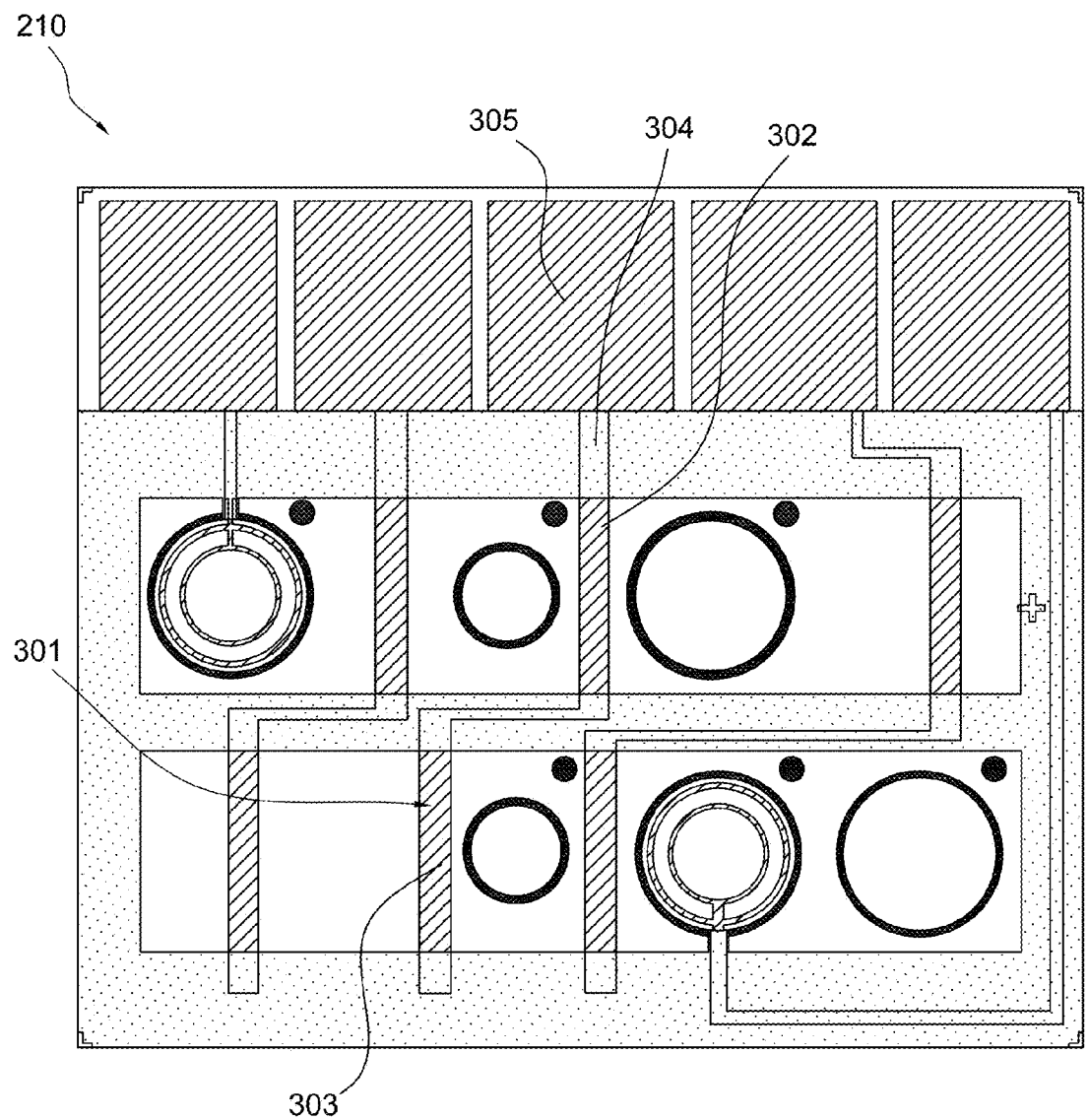

As shown in FIGS. 15 and 16, in some embodiments, the microfabricated sensor array may comprise a silicon chip 210 that includes micro-environment amperometric sensors or transducers 215 and 220 located on different vertical planes (a) and (b) of the silicon chip 210. The sensor 215 may be connected via wiring 225 to a first amperometric pin 230 (e.g., temporary electrical connector) and the sensor 220 may be connected via wiring 235 to a second amperometric pin 240 (e.g., temporary electrical connector). In some embodiments, the sensor 215 may be configured as an aPTT sensor and the sensor 220 may be configured as a PT sensor both of which are formed on the single silicon chip 210 and positioned within one or more conduits of the point of care test cartridge. As illustrated in FIG. 15, the sensor 215 may be constructed with a target reticle design preferably comprising a plurality of concentric rings (e.g., 2, 3, 4 or more concentric rings) in an upper area of the silicon chip 210 and the sensor 220 may be constructed with a target reticle design preferably comprising a plurality of concentric rings (e.g., 2, 3, 4 or more concentric rings) in a lower area of the silicon chip 210. Specifically, the design and arrangement of the sensors 215 and 220 on the chip 210 are selected based on printing and performance characteristics for each of the sensors 215 and 220. However, it should be understood to those of ordinary skill in the art that any design or arrangement for the sensors is contemplated without departing from the spirit and scope of the present invention. Furthermore, although the sensors 215 and 220 in the example in FIG. 15 are amperometric sensors, other electrochemical processes or optical processes which use other electrochemical or optical sensors, e.g., optical wave guides and charge-coupled device (CCD) camera chips, can be used. For example, a potentiometric sensor may be used to detect ion species such as $Na^+$ or $K^+$.

As described herein, the amperometric sensors or transducers 215 and 220 may be formed as electrodes with gold surfaces that are exposed (e.g., no polyimide or photoresist covering) to the inside environment of the conduit and configured to directly contact a biological sample disposed within the conduit. The wirings 225 and 235 may be formed with gold surfaces that are coated with a photo defined polyimide or photoresist layer such that the wirings 225 and 235 are insulated from exposure to the biological sample disposed within the conduit. The wirings 225 and 235 may be formed comprising containment ring structures 245 and 250 configured to contain the immobilized reagent-substrate-polymer layer. For example, the immobilized reagent-substrate-polymer layer (as discussed above with respect to FIGS. 4, 7A, 7B, and 7C) may be deposited onto at least a portion of the sensors 215 and/or 220 within the containment ring structures 245 and/or 250. The wirings 225 and 235 terminate at the first amperometric pin 230 and the second amperometric pin 240 respectively, which are used to make contact with a connector in an analyzer or cartridge reader (e.g., an i-STAT® cartridge reader as described in U.S. Pat. No. 4,954,087, the entirety of which is incorporated herein by reference).

In the preferred embodiments of the present invention, the analyzer applies a potential via the first amperometric pin 230 and the second amperometric pin 240 between each of the amperometric sensors 215 and 220 and a reference electrode (described in detail below with respect to FIG. 17), and measures current changes generated by cleaved substrate as an electrochemical signal. The electrochemical signal being proportional to the concentration of the product in the biological sample. The amperometric sensors 215 and 220 have an applied potential of approximately +0.4 V versus the reference electrode and, in another preferred embodiment, the amperometric sensors 215 and 220 have an applied potential of approximately +0.1 V versus the reference electrode. The signal generated by the enzyme reaction product at approximately +0.1V is distinguishable from the signal generated by the unreacted substrate at approximately +0.4 V.

In the embodiments of the invention which use the thrombin cleavable peptide Tos-Gly-Pro-Arg-, H-D-Phe-Pip-Arg, or Bz-Phe-Val-Arg attached to an N-phenyl-p-phenylenediamine or N-[p-methoxyphenyl-]-p-phenylenediamine detectable moiety, the intact substrates are detected at a voltage of approximately +0.4V. The electrogenic reaction products N-phenyl-p-phenylenediamine or N-[p-methoxyphenyl-]-p-phenylenediamine are detected at a voltage of approximately +0.1V. Thus in these embodiments, the analyzer applies a potential to the amperometric sensors 215 and 220 with the generation of an electrochemical signal which is proportional to the concentration of the substrate in the biological sample. Also, the analyzer applies a potential to the amperometric sensors 215 and 220 with the generation of an electrochemical signal which is proportional to the concentration of the product in the biological sample. After hydrolysis of the substrate by thrombin, a product is formed which reacts at the amperometric sensors 215 and 220 with the generation of a signal distinguishable from the signal generated by the substrate.

It should be noted that the exact voltages used to amperometrically detect the substrate and the product will vary depending on the chemical structure of the substrate and product. It is important that the difference in the voltages used to detect the substrate and the product be great enough to prevent interference between the readings. With some substrates, the voltage required to electrochemically detect the substrate is so high as to be beyond practical measurement in an aqueous buffered solution. In these cases, it is only necessary that the product be detectable amperometrically.

In some embodiments, the silicon chip 210 shown in FIG. 15 may further include multi-conduit conductometric sensors 255 and 260 (e.g., hematocrit sensors). The conductimetric sensors 255 and 260 are configured to determine biological sample arrival and/or departure at the amperometric sensors 215 and 220. More specifically, the conductometric sensors 255 and 260 lie perpendicular to a length of the conduit or sensor conduit, and an electrical resistance between pairs of electrodes for each sensor may be used to monitor a relative position of a fluid front of the biological sample. At the extremes, an open circuit reading indicates that the biological sample has been pushed off the amperometric sensors 215 and 220 and a closed circuit reading indicates the amperometric sensors 215 and 220 are covered with the biological sample.

As shown in FIG. 15, the conductometric sensor 255 may comprise at least two electrodes 265 and 270 (i.e., first electrode pair) positioned upstream of a midpoint of the amperometric sensor 215. The electrodes 265 and 270 may be connected via wirings 275 and 280 to a conductometric low pin 285 and an AC source or conductometric high pin 290, respectively (e.g., temporary electrical connectors). The wirings 275 and 280 may be formed with a gold surface that is coated with a photo defined polyimide or photoresist layer such that the wirings 275 and 280 are insulated from exposure to the biological sample disposed within the conduits. The conductometric sensor 260 may comprise at least two electrodes 295 and 300 (i.e., second electrode pair) positioned downstream of a midpoint of the amperometric sensor 220. The electrodes 295 and 300 may be connected via wirings 275 and 280 to a conductometric low pin 285 and an AC source or conductometric high pin 290, respectively (e.g., temporary electrical connectors). As such, in some embodiments, the fluid reaches the first electrode pair in a first fluidic conduit (e.g., prior to arriving at amperometric sensor 215), then subsequently arrives at the second electrode pair in a second fluidic conduit (e.g., after arriving at amperometric sensor 220).

As shown in FIG. 16, in another embodiment, the silicon chip 210 may further include a third conductometric sensor 301 comprising at least two electrodes 302 and 303. The electrodes 302 and 303 may be connected via wiring 304 to a second AC source or conductometric high pin 305 (e.g., temporary electrical connector). In accordance with these aspects of the present invention, the use of a third sensor allows for two binary fluid detection events, e.g., both are OFF/ON, which is easily detectable with the current circuitry and software limitations. In the case of two conductivity sensors (shown in FIG. 15), the current circuitry and software relies on the ability to detect two 'drops' in the resistance of the sample in quick succession. Typically the first drop is large as it goes from a dry state to a wet state and the circuit is completed. The second drop in resistance, when the sample arrives in the second fluidic conduit, is much smaller and therefore more difficult to differentiate from signal noise and small changes in the signal. In addition, the amplitude of each resistance change varies depending on the sample properties. Accordingly and advantageously, in some embodiments, the arrangement of having three conductometric sensors allows for two switchable conductivity paths using the conductometric sensor 255 (shown in FIG. 15) and the conductometric sensor 301 (shown in FIG. 16).

Figure 17:
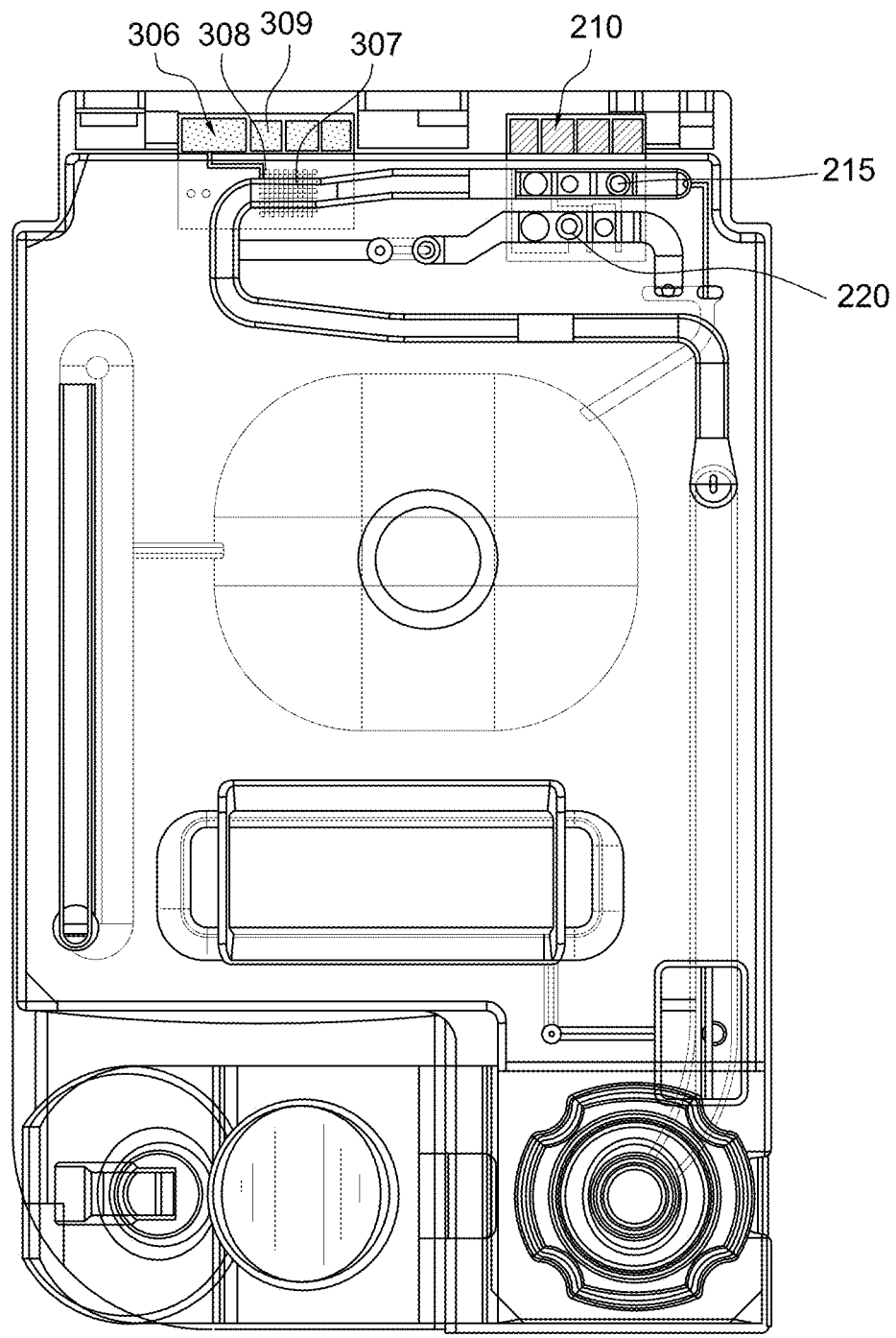
FIG. 17 shows a top view of a disposable sensing device in accordance with some aspects of the invention.

As shown in FIG. 17, in some embodiments, the microfabricated sensor array may further comprise a ground chip 306 that includes a reference sensor or electrode 307. In accordance with aspects of the present invention, in which the sensors 215 and 220 are amperometric sensors, the reference electrode 307 may be configured as a counter electrode to complete the circuitry. In a preferred embodiment, the reference electrode 307 may comprise silver metal (Ag) and its silver salt (AgCl) deposited on a solid substrate (i.e., an Ag/AgCl reference electrode). The reference electrode 307 may be connected via wiring 308 to a reference pin 309 (e.g., temporary electrical connector). The microfabricated sensor array may be designed such that the ground chip 306 is positioned upstream of the semiconductor chip 210 as discussed in further detail with respect to FIGS. 15 and 16. However, it should be understood that other arrangements for sensor and ground chips are possible without departing from the spirit and scope of the present invention. For example, the sensor array may further comprise one or more additional sensor chips (not shown) configured to detect various analytes of potential interest, such as troponin I, troponin T, CKMB, procalcitonin, bHCG, HCG, NTproBNP, proBNP, BNP, myoglobin, parathyroid hormone, d-dimer, NGAL, galectin-3, and/or PSA, among other analytes.

Figure 18:
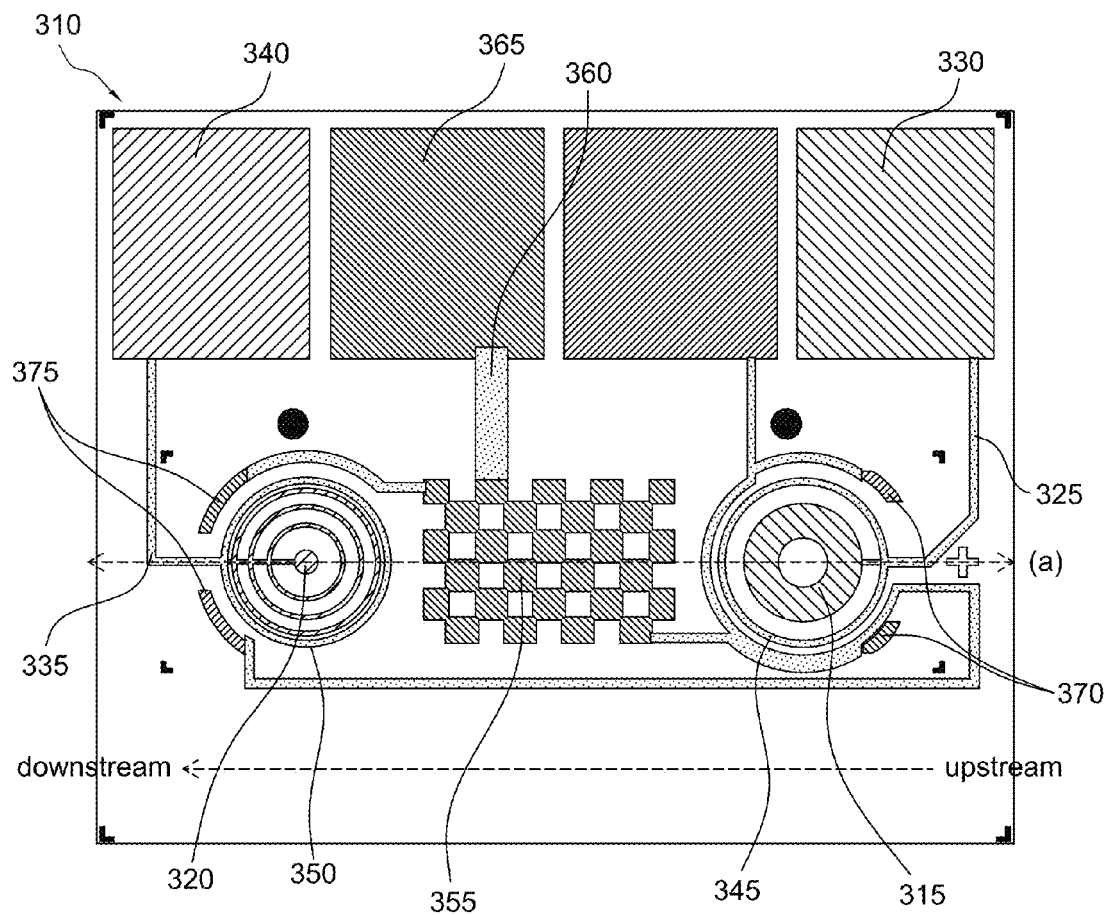
FIGS. 18-20 show multiple sensor configurations in accordance with some aspects of the invention.

As shown in FIG. 18, in preferred embodiments, the microfabricated sensor array may comprise a silicon chip 310 that includes micro-environment amperometric sensors or transducers 315 and 320 located on a same vertical plane (a) of the silicon chip 310. The sensor 315 may be connected via wiring 325 to a first amperometric pin 330 (e.g., temporary electrical connector) and the sensor 320 may be connected via wiring 335 to a second amperometric pin 340 (e.g., temporary electrical connector). In some embodiments, the sensor 315 may be configured as an aPTT sensor and the sensor 320 may be configured as a PT sensor both of which are formed on a single chip 310 and positioned within the conduit of the point of care test cartridge. As illustrated in FIG. 18, the sensor 315 may be constructed with a donut shaped design in an upstream position to that of the sensor 320 constructed with a target reticle design comprising a plurality of concentric rings (e.g., 2, 3, 4 or more concentric rings). Specifically, the design and arrangement of the sensors 315 and 320 on the chip 310 are selected based on printing and performance characteristics for each of the sensors 315 and 320. However, it should be understood to those of ordinary skill in the art that any design or arrangement for the sensors is contemplated without departing from the spirit and scope of the present invention. Furthermore, although the sensors 315 and 320 in the example in FIG. 18 are amperometric sensors, other electrochemical processes or optical processes which use other electrochemical or optical sensors can be used. For example, a potentiometric sensor may be used to detect ion species such as $Na^+$ or $K^+$.

As described herein, the sensors or transducers 315 and 320 may be formed as electrodes with gold surfaces that are exposed (e.g., no polyimide or photoresist covering) to the inside environment of the conduit and configured to directly contact a biological sample disposed within the conduit. The wirings 325 and 335 may be formed with gold surfaces that are coated with a photo defined polyimide layer such that the wirings 325 and 335 are insulated from exposure to the biological sample disposed within the conduit. The wirings 325 and 335 may be formed comprising containment ring structures 345 and 350 configured to contain the immobilized reagent-substrate-polymer layer. For example, the immobilized reagent-substrate-polymer layer (as discussed above with respect to FIGS. 4, 7A, 7B, and 7C) may be deposited onto at least a portion of the sensors 315 and/or 320 within the containment ring structures 345 and/or 350. The wirings 325 and 335 terminate at the first amperometric pin 330 and the second amperometric pin 340 respectively, which are used to make contact with a connector in an analyzer or cartridge reader (e.g., an i-STAT® cartridge reader as described in U.S. Pat. No. 4,954,087).

In some embodiments, the silicon chip 310 further includes an integrated reference electrode 355. In accordance with aspects of the present invention, in which the sensors 315 and 320 are amperometric sensors, the reference electrode 355 is configured as a counter electrode to complete the circuitry. The reference electrode 355 may comprise silver metal (Ag) and its silver salt (AgCl) deposited on a solid substrate (i.e., a Ag/AgCl reference electrode). The reference electrode may be connected via wiring 360 to an AC ground and reference pin 365 (e.g., temporary electrical connector). The wiring 360 may be formed with a gold surface that is coated with a photo defined polyimide or photoresist layer such that the wiring 360 is insulated from exposure to the biological sample disposed within the conduit. In preferred embodiments, the reference electrode 355 is designed in a checkerboard pattern as illustrated in FIG. 18 to improve wettability of a surface of the reference electrode 355. Specifically, it has been found unexpectedly that the wettability of the reference electrode 355 may be improved using the checkerboard pattern because AgCl is relatively hydrophobic and can promote the formation of an air bubble over the surface of the reference electrode 355 when a solid patch of AgCl is used, which results in a poor circuit.

Figure 19:
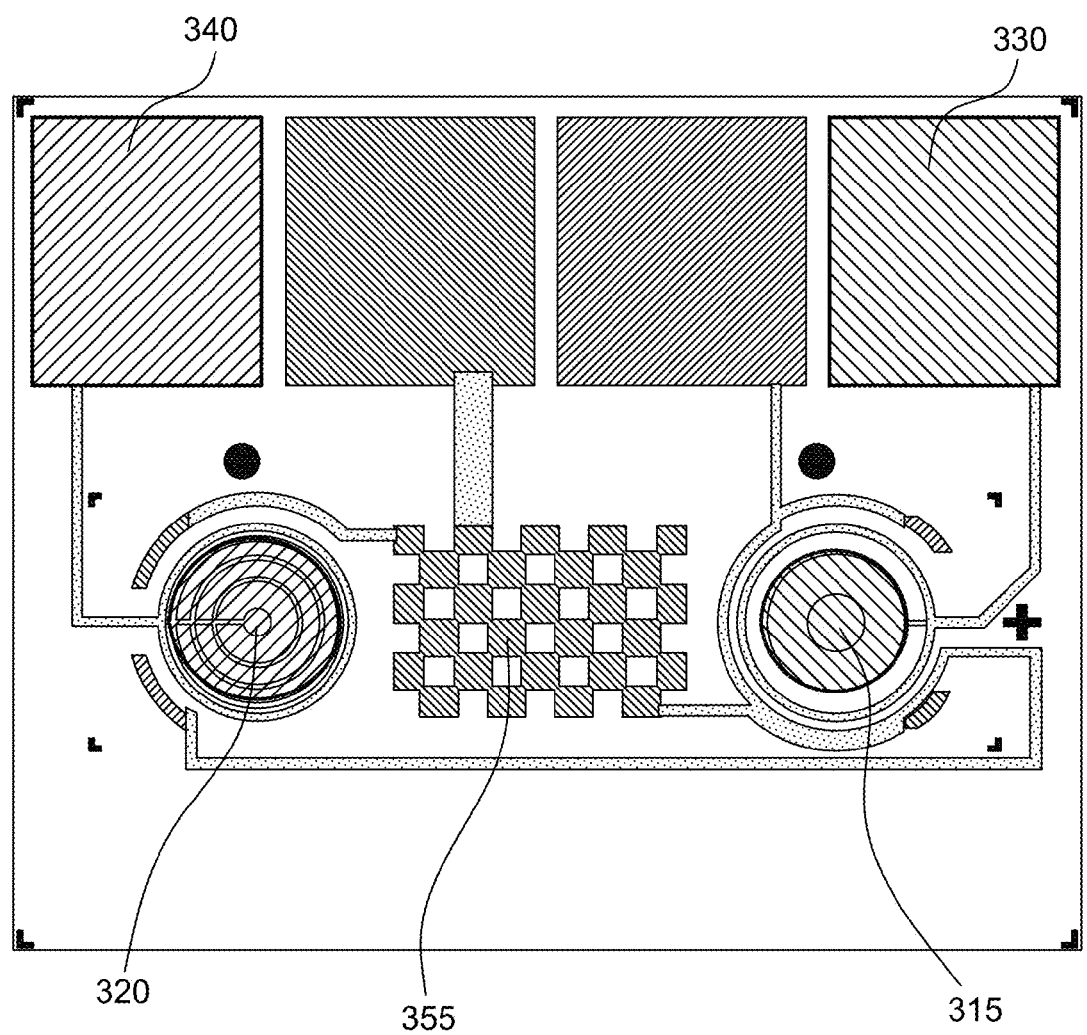

As discussed in detail above with respect to the silicon chip 310 and as shown in FIG. 19, in the preferred embodiments of the present invention the analyzer applies a potential via the first amperometric pin 330 and the second amperometric pin 340 between each of the amperometric sensors 315 and 320 and the reference electrode 355, and measures current changes generated by cleaved substrate as an electrochemical signal. The electrochemical signal being proportional to the concentration of the product in the biological sample. The amperometric sensors 315 and 320 have an applied potential of approximately +0.4 V versus the reference electrode 355 and, in another preferred embodiment, the amperometric sensors 315 and 320 have an applied potential of approximately +0.1 V versus the reference electrode 355. The signal generated by the enzyme reaction product at approximately +0.1 V is distinguishable from the signal generated by the unreacted substrate at approximately +0.4 V.

With reference back to FIG. 18, in some embodiments, the silicon chip 310 may further include conductometric sensors 370 and 375 (which can also function as hematocrit sensors). The conductimetric sensors 370 and 375 may be split to form two sensor pairs with one at each end of the chip 310. The conductimetric sensors 370 and 375 are configured to determine biological sample arrival and/or departure at the amperometric sensors 315 and 320, respectively. More specifically, the conductometric sensors 370 and 375 lie in an arc that is perpendicular to a length of the conduit or sensor conduit, and an electrical resistance between pairs of electrodes for each sensor may be used to monitor a relative position of a fluid front of the biological sample. At the extremes, an open circuit reading indicates that the biological sample has been pushed off the amperometric sensors 315 and 320 and a closed circuit reading indicates the amperometric sensors 315 and 320 are covered with the biological sample.

Figure 20:
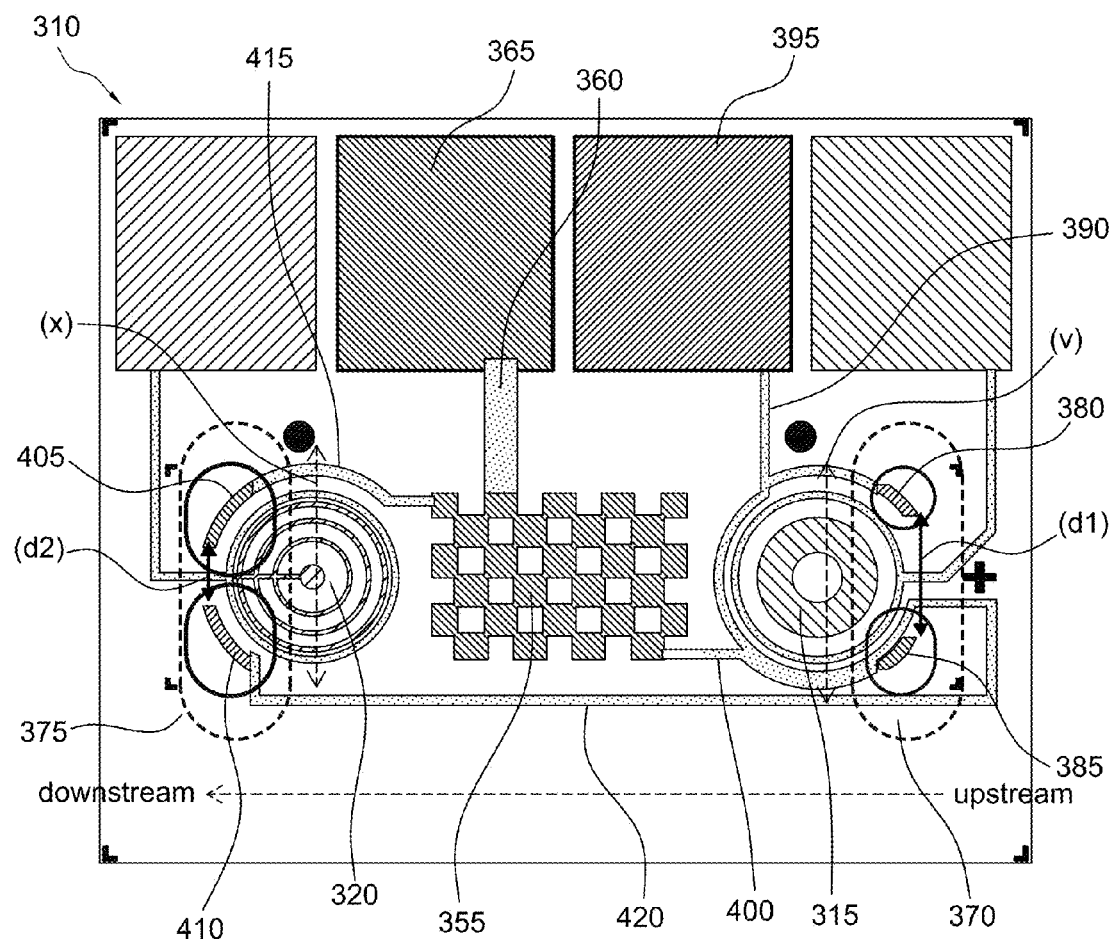

As shown in FIG. 20, the conductometric sensor 370 may comprise at least two electrodes 380 and 385 (i.e., first electrode pair) positioned at a predetermined distance (d1) from one another. In some embodiments, the conductometric sensor 370 may be positioned on the silicon chip 310 relative to a midpoint (v) of the amperometric sensor 315 (e.g., upstream, downstream, or in-line with the midpoint (v)). The electrode 380 may be connected via wiring 390 to an AC source pin 395 (e.g., temporary electrical connector). The electrode 385 may be connected via wiring 400, the reference electrode 355, and the wiring 360 to the AC ground and reference pin 365. The wirings 390 and 400 may be formed with a gold surface that is coated with a photo defined polyimide or photoresist layer such that the wirings 390 and 400 are insulated from exposure to the biological sample disposed within the conduit.

The conductometric sensor 375 may comprise at least two electrodes 405 and 410 (i.e., second electrode pair) positioned at a predetermined distance (d2) from one another. In some embodiments, the conductometric sensor 375 may be positioned on the silicon chip 310 relative to a midpoint (x) of the amperometric sensor 320 (e.g., upstream, downstream, or in-line with the midpoint (x)). The electrode 405 may be connected via wiring 415, the reference electrode 355, and the wiring 360 to the AC ground and reference pin 365. The electrode 410 may be connected via wiring 420 and the wiring 390 to the AC source pin 395. The wirings 415 and 420 may be formed with a gold surface that is coated with a photo defined polyimide or photoresist layer such that the wirings 415 and 420 are insulated from exposure to the biological sample disposed within the conduit.

Figure 21:
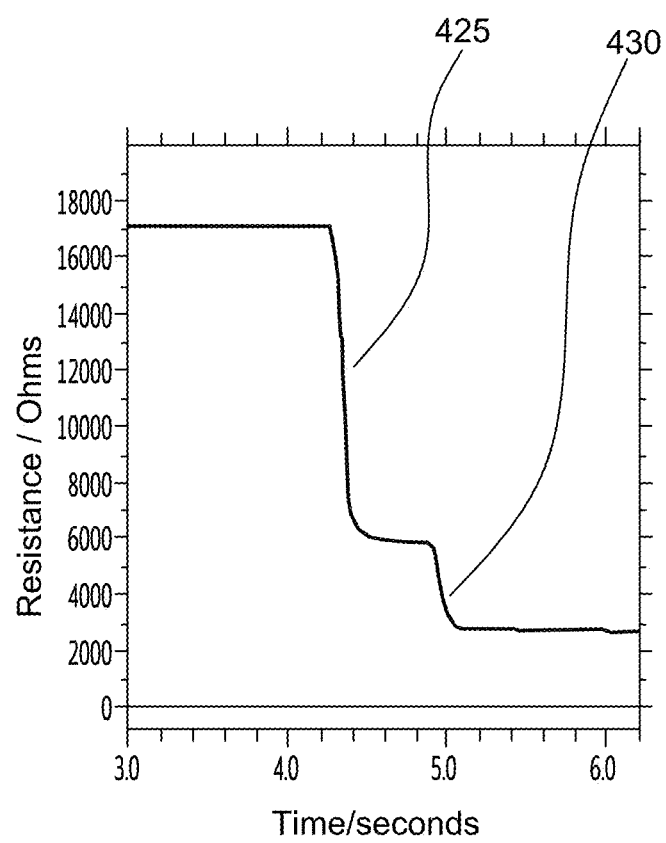
FIGS. 21, 22A, and 22B illustrate the principle of operation for conductometric sensors in accordance with some aspects of the invention.

In preferred embodiments, the conductometric sensors 370 and 375 are configured to detect arrival of the biological sample within the conduit at the amperometric sensors 315 and 320, respectively. As shown in FIG. 21, the arrival of the biological sample at the amperometric sensors 315 and 320 may be detected based on determination of a first resistance drop 425 when the biological sample reaches conductivity sensor 370 and a second resistance drop 430 when the biological sample reaches conductivity sensor 375. In additional or alternative embodiments, determination of a rise or spike (not shown) in the resistance at either or both of the conductometric sensors 370 and 375 may be used to detect the presence of an air bubble within the conduit that is positioned over either or both of the amperometric sensors 315 and 320.

Figure 22A:
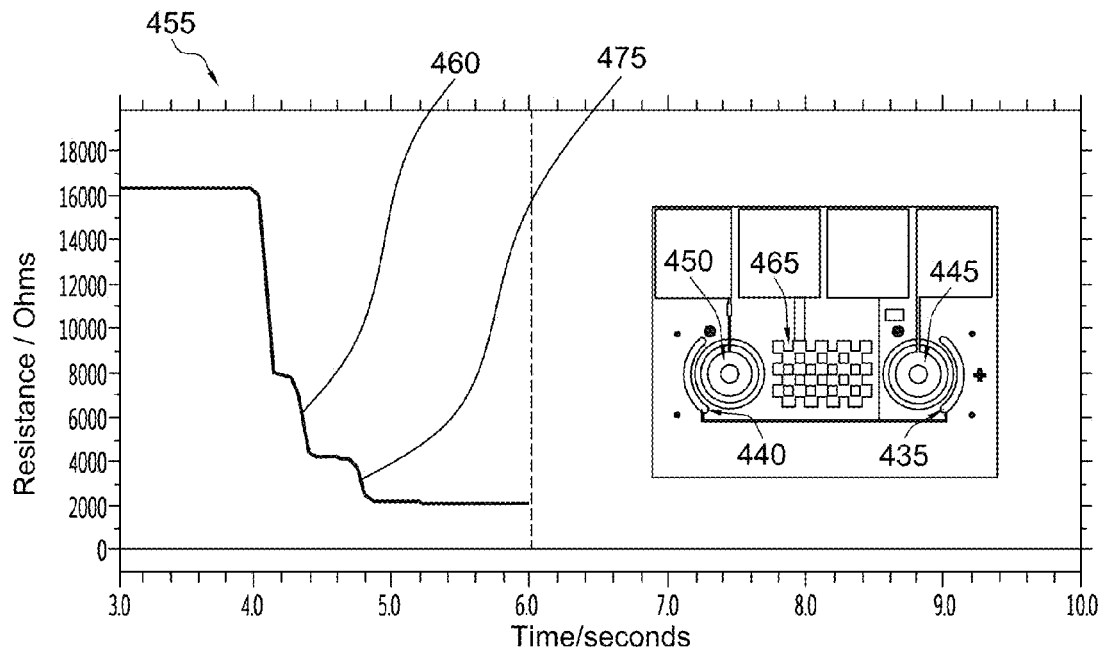

A resistance profile for the conductometric sensors 370 and 375 should preferably provide two well defined resistance drops of roughly equal amplitude. In some chip designs, as shown in FIG. 22A, conductometric sensors 435 and 440 may be configured as separate bars on opposite ends of the chip near respective amperometric sensors 445 and 450. However, the resistance profile 455 for such a design is found to often include an additional step 460, which is attributable to the sample temporarily stopping on the reference electrode 465 due to the hydrophobic nature of the reference electrode 465. As should be understood, this could make it difficult to decipher the second resistance drop as either the wetting of the reference electrode 465 or the sample arriving at the second conductometric sensor 440. Additionally, the time between the two steps is quite short, making the timing difficult, and the resistance drop of the second arrival is much smaller compared to the first drop, making the detection difficult.

Figure 22B:
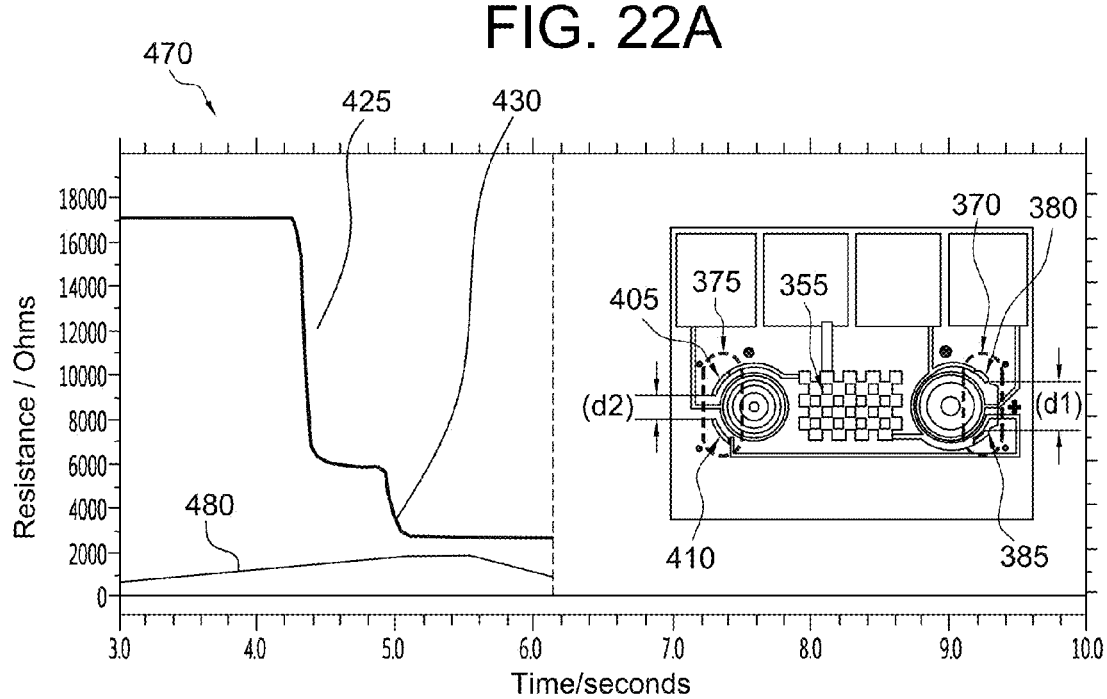

Accordingly, as shown in FIG. 22B, the chip design implemented in preferred embodiments of the present invention utilizes the conductometric sensors 370 and 375, which are each split to comprise at least two electrodes 380, 385 and 405, 410 spaced apart at predetermined distances (d1) and (d2), respectively. As illustrated in the resistance profile 470, the dominant resistance drops 425 and 430 occur at the two pairs of conductometric sensors 370 and 375. Thus, reducing the impact of the additional resistance drop 460 (shown in FIG. 22A) observed from the wetting of the reference electrode 355. Further, the conductometric sensors 370 and 375 are placed at a front and rear of the chip to increase a time between the resistance drops 425 and 430 to better differentiate the resistance drops 425 and 430. Moreover, in some embodiments, the spacing or predetermined distance (d1) provided between the electrodes 380 and 385 is a value "n" greater than that of the spacing or predetermined distance (d2) provided between the electrodes 405 and 410 such that an amplitude of the second resistance drop 430 is increased over a resistance drop 475 (shown in FIG. 22A) of the alternative chip design. For example, (d1) may be constructed twice as large as that of (d2) to achieve about a 1000 ohm increase in amplitude of the second resistance drop. The increase in (d1) over that of (d2) effectively increases the ratio of resistance drops for the chip design shown in FIG. 22B over that of the ratio of resistance drops for the chip design shown in FIG. 22A. Advantageously, this increase in resistance drops allows for better detection of the arrival of the biological sample at the conductometric sensors 370 and 375 during an on/forward motor or pump position 480.

In some embodiments, processes of the present invention may include continually moving the biological sample forward and back over the chip at a controlled velocity. Controlling the time for which the conductometric sensors 370 and 375 remain as open and closed circuits controls the position at which the biological sample changes direction. For example, a pneumatic pump within the analyzer may be configured to oscillate the biological sample in the conduit with the trailing edge of the biological sample positioned in the region of the conductometric sensor 370 in order to dissolve the substrate in that portion of the sample near the trailing edge. The oscillation may be at a frequency in the range of 0.2 to 10 Hertz for a period in the range of 1 to 100 seconds. In a preferred method, the oscillation may be at a frequency in the range of about 1.5 Hertz for a period of about 20 seconds. In another preferred method the oscillation may be at a frequency of about 0.3 Hertz and the amperometric sensors 315 and 320 (as shown in FIG. 20) may be configured to generate a signal at each oscillation. If erythrocytes are present in the biological sample, the oscillation may be at a frequency adequate to prevent the settling of erythrocytes on the the amperometric sensors 315 and 320.

In some embodiments, the amperometric sensors 315 and 320 determine the concentration of product each time the biological sample is oscillated past the amperometric sensors 315 and 320. For example, a first amperometric sensor signal may be stored by the analyzer for each of the amperometric sensors 315 and 320 and subsequent signals from the amperometric sensors 315 and 320 may be stored and compared to the first and other stored signals in order to determine a maximum rate of change in the amperometric sensor signals. These data points may then be analyzed to determine a fixed fraction of a maximum rate of change of the amperometric sensor signals. These data points may thus be used to determine a coagulation parameter of interest for each of the amperometric sensors 315 and 320.

In alternative embodiments, the sensors or transducers may be formed as an optical detector, e.g. CCD camera chip and optical wave guide. The optical detector may either be a detector of fluorescence, chemiluminescence, or bioluminescence emission from the detectable moiety or a detector of absorbance by the detectable moiety. In such embodiments, the detectable moiety may be an optical dye, a fluorescence emitter, chemiluminescence emitter or a bioluminescence emitter.

In other embodiments, the sensor or transducers may be formed as a test strip, e.g., a glucose test strip, as described in U.S. patent application Ser. No. 13/724,348, which is incorporated herein in its entirety. For example, a test strip may be included within the cartridges described herein. In some embodiments, the sample may be manually placed on the test strip and, as such, the microfluidic systems described herein would not need to be included with such embodiments. As is well known in the art, glucose test strip devices can include passive capillary fluidic elements to deliver the sample to a sensor or sensor array. As such, the elements, features, and functionality of a glucose test strip could be adapted to the present invention without departing from the spirit and scope of the present invention.

Systems and Processes for Sample Analysis

Figure 23:
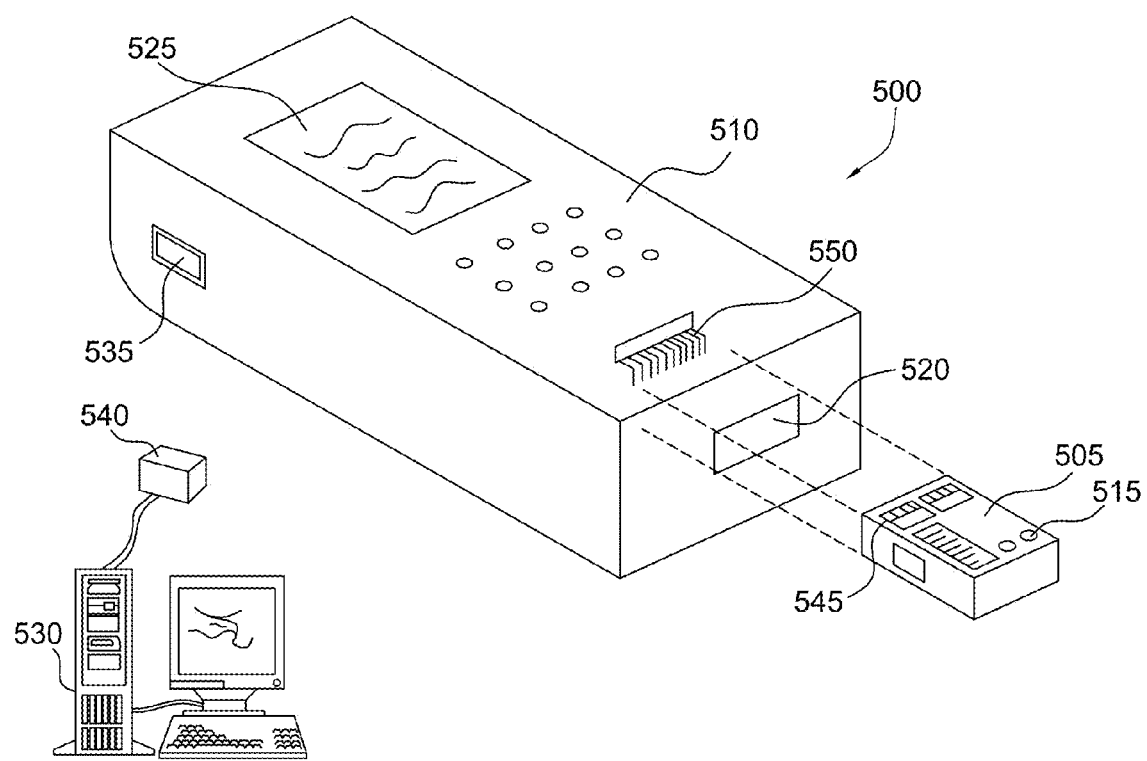
FIG. 23 shows an isometric view of a disposable sensing device and reader device in accordance with some aspects of the invention.

As shown in FIG. 23, the system 500 of the present invention may comprise a self-contained disposable sensing device or cartridge 505 and a reader device or instrument 510 (e.g., an analyzer). In some embodiments, the cartridge 505 is a single-use device configured to be disposable after the single-use. A fluid sample (e.g., whole blood) to be measured is drawn into a sample entry orifice or port 515 in the cartridge 505, and the cartridge 505 may be inserted into the reader 510 through a slotted opening 520. The reader 510 may comprise a processor configured to perform measurements of analyte concentrations, measurements of resistances, identify analytes or sets of analytes that a chip is configured to measure, and/or determinations of diagnostic clotting time within the fluid sample, as discussed herein in further detail. Measurements and determinations performed by the reader 510 may be output to a display 525 or other output device, such as a printer or data management system 530 via a port 535 on the reader 510 to a computer port 540. Transmission can be via Wifi, Bluetooth link, infrared and the like. In embodiments where the sensors 545 in the cartridge 505, e.g., micro-environment sensors, are based on electrochemical principles of operation, (e.g., a first sensor and optionally a second sensor) may be configured to make electrical contact with the reader 510 via an electrical connector 550. For example, the connector may be of the design disclosed in jointly owned U.S. Pat. No. 4,954,087, incorporated herein by reference in its entirety. In some embodiments, the PT and aPTT sensors may be configured to connect with an electrical connector of a test meter within the reader 510 via the the electrical connector 550 (see, e.g., U.S. Pat. Nos. 5,096,669 and 4,954,087, incorporated herein by reference in their entireties). The reader 510 may also include a method for automatic fluid flow compensation in the cartridge 505, as disclosed in jointly owned U.S. Pat. No. 5,821,399, which also is incorporated herein by reference in its entirety.

Figure 24:
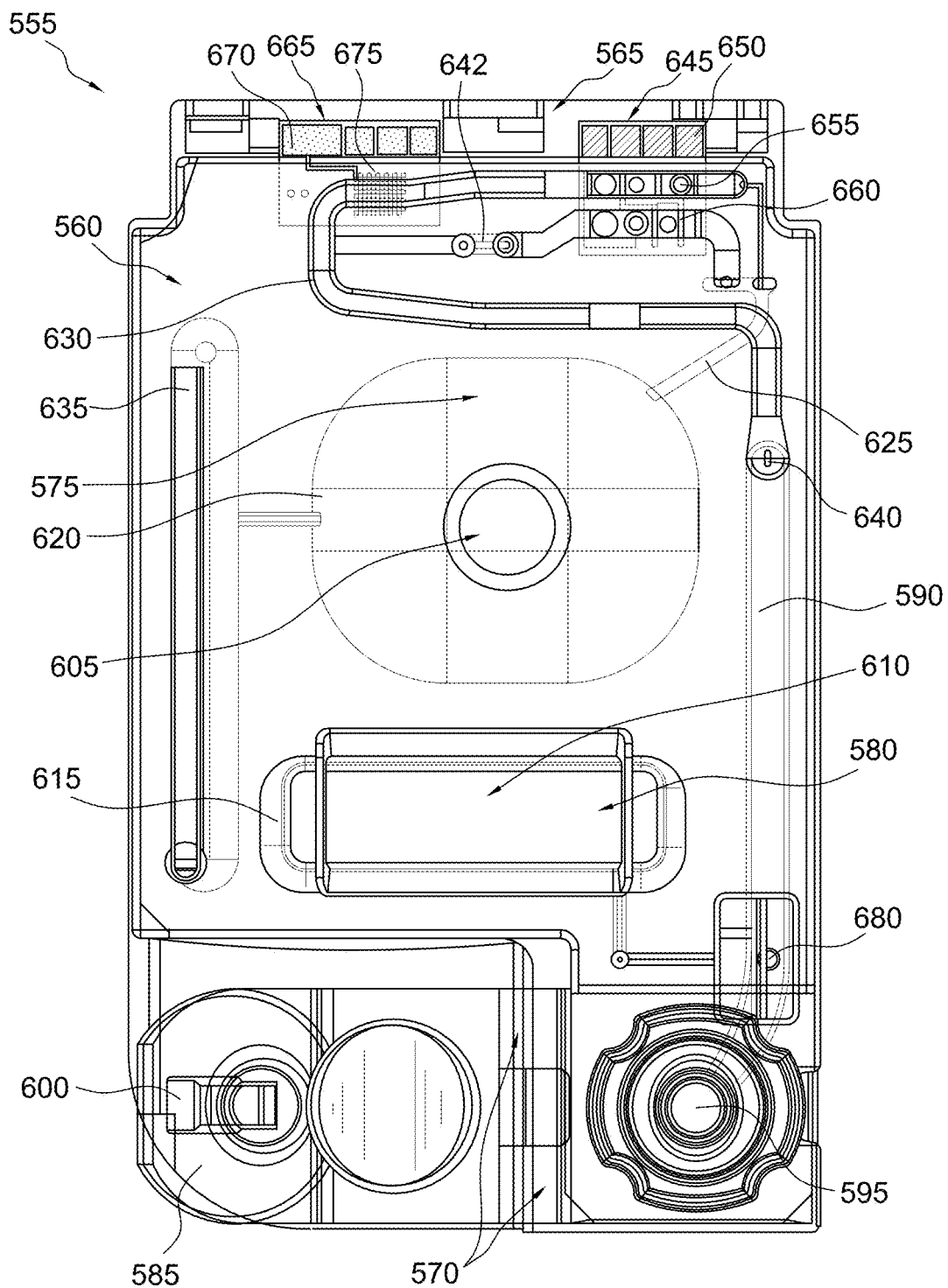
FIG. 24 shows a top view of a disposable sensing device in accordance with some aspects of the invention.

In one embodiment, as shown in FIG. 24, the self-contained disposable sensing device or cartridge 555 may comprise a cover 560, a base 565, and a thin-film adhesive gasket (not shown) that is disposed between the base 565 and the cover 560. The cartridge 555 may be configured for insertion into the reader 510, and therefore the cartridge 555 may comprise a plurality of mechanical and electrical connections (not shown) for this purpose. Advantageously, a feature of the cartridge 555 is that once a fluid or biological sample is loaded within the cartridge 555, analysis of the fluid or biological sample may be completed and the cartridge 555 may be discarded without an operator or others contacting the fluid or biological sample.

Referring to FIG. 24, the cover 560 may be made of a rigid material, preferably plastic, and capable of repetitive deformation at flexible hinge regions 570, 575, and 580 without cracking. The cover 560 may comprise a lid 585, attached to a main body of the cover 560 by the flexible hinge 570. In operation, after introduction of the fluid or biological sample into a sample holding chamber 590 through a sample entry port 595, the lid 585 may be secured over an entrance to the sample entry port 595, preventing sample leakage. The lid 585 may be held in place by a hook 600. The cover 560 may further comprise two deformable members 605 and 610 that are moveable relative to the body of the cover 560, and which may be attached to the cover 560 by the flexible hinge regions 575 and 580.

The deformable member 610 may be configured to be operated by a first pumping means such that a force is exerted upon an air bladder comprised of cavity 615 and the gasket. Operation of the deformable member 610 displaces fluid within conduits of the cartridge 555. The deformable member 605 may be configured to be operated upon by a second pumping means such that a force is exerted upon the gasket, which can deform because of slits cut therein. In some embodiments, deformation of the gasket may transmit pressure onto a fluid-containing foil pack filled with a fluid, e.g., approximately 130 μL of analysis/wash solution, a control fluid, or calibrant fluid, located in cavity 620, rupturing the foil pack, and expelling fluid into conduit 625 for subsequent use in other conduits during sample analysis. As should be understood, while coagulation assay formats do not generally require the use of these fluids, the fluids may generally be required in a single device that combines coagulation tests with other tests, e.g., a wash fluid in immunoassays for analytes such as BNP and troponin, and a calibrant fluid in chemistry tests such as potassium, creatinine and glucose. In alternative embodiments, the deformation of the gasket may transmit pressure onto an air bladder comprised of cavity 620 for displacing fluid within conduits of the cartridge 555. In yet additional embodiments, the second pumping means may not operate upon the cavity 620, and instead, the cavity 620 may be configured as a waste chamber.

Additional action in the cartridge 555 generated by mechanisms within the reader 510 (discussed with respect to FIG. 23) applied to the cartridge 555 may be used to inject one or more air segments into the fluid or biological sample at controlled positions within the sample holding chamber 590 and conduit 630. The air segments may be used to wash a sensor surface of the sensor array and the surrounding conduit 630 with a minimum amount of fluid (e.g., a limited wash cycle in which the volume of wash may be less than fifty times a volume of the fluid or biological sample and/or fewer than three independent cycles of clean wash buffer (e.g., three independent washing steps with fresh wash buffer)), as should be understood by those of ordinary skill in the art of immunoassay procedures. For example, the cover 560 may further comprise a hole covered by a thin pliable film. In operation, pressure exerted upon the film may expel one or more air segments into the conduit 630 through a small hole in the gasket. In some embodiments, a cross-sectional area of the conduit 630 may be in the range of about 0.1 mm$^2$ to about 10 mm$^2$.

In some embodiments, a lower surface of the cover 560 further comprises sample holding chamber 590, the conduit 630 and another conduit 635 (e.g., a waste conduit). The sample holding chamber 590 and the conduit 630 may include one or more constrictions or capillary stops 640 and 642 that control fluid flow by providing resistance to the flow of the fluid or biological sample. Optional coatings (not shown), e.g., dry reagent coatings, may provide hydrophobic surfaces on the conduit 630, which together with gasket holes control fluid flow between the sample holding chamber 590 and the conduit 635. The sample holding chamber 590 may be configured to connect the sample entry port 595 to the conduit 630 in the assembled cartridge 555.

In accordance with aspects of the present invention in which there are multiple chips (e.g., a ground chip and a sensor chip), the cutaway 645 may house one or more sensor chips 650 comprising at least one sensor 655 (e.g., a PT, aPTT, or ACT micro-environment sensor), or a responsive surface, together with an optional conductimetric sensor or sensors 660. The cutaway 665 may house a ground chip 670 comprising a ground electrode 675 if needed as a return current path for an electrochemical sensor, and may also house an optional conductimetric sensor. In accordance with aspects of the present invention in which there is only a single chip, (e.g., a combined ground and sensor chip) the cutaway 665 and the ground chip 670 may not be included with the cartridge 555.

In some embodiments, a metering means may be provided that comprises the sample holding chamber 590 bounded by the constriction or capillary stop 640 and having along the sample holding chamber 590 length an air entry point 680 from the bladder comprising cavity 615. Air pressure exerted at the entry point 680 drives a metered volume of the sample past the constriction or capillary stop 640. Therefore, a metered volume of sample may be predetermined by a volume of the sample holding chamber 590 between the air entry point 680 and the constriction or capillary stop 640. An amount of the sample corresponding to this volume may be displaced into the conduit 630 when the deformable member 605 is displaced. This arrangement may therefore provide a metering means for delivering a metered amount of an unmetered sample into the various downstream conduits of the cartridge 555. The metering may be advantageous in some embodiments if quantization of an analyte is required. Thus, an operator may be relieved of accurately measuring the volume of the sample prior to measurement saving time, effort, and increasing the accuracy and reproducibility.

In preferred embodiments, the invention is a process for using a cartridge to determine diagnostic clotting times in a whole blood sample. The process may include introducing an unmetered fluid sample into the sample holding chamber 590 of the cartridge 555 through the sample entry port 595 (as shown in FIG. 24). Capillary stop 640 prevents passage of the fluid sample into conduit 630 at this stage, and the sample holding chamber 590 is filled with the sample. Lid 585 is closed to prevent leakage of the fluid sample from the cartridge 555. The cartridge 555 may then be inserted into the reading device or apparatus 510, as shown in FIG. 23 and further disclosed in U.S. Pat. No. 5,821,399, which is incorporated herein by reference in its entirety. In some embodiments, insertion of the cartridge into the reading apparatus 510 activates a mechanism, which punctures the fluid-containing package located in the cavity 620 when the package is pressed against a spike (not shown). Fluid may thereby be expelled into one or more conduits (e.g., conduit 630) arriving in sequence at the sensor region. Thereafter, operation of a pump means (e.g., a pneumatic pump) applies pressure to the air-bladder comprised of cavity 615, forcing air through a conduit into the sample holding chamber 590 at the air entry point 680. Capillary stop 640 delimits a metered portion of the original fluid sample. The metered portion of the sample is then expelled through the capillary stop 640 by air pressure produced within air bladder comprised of cavity 615. The sample passes into the conduit 630 and into contact with the one or more reagents, the one or more substrates (e.g., an immobilized reagent-substrate-polymer layer), and/or the one or more sensors comprising one or more transducers and optionally the reference electrode located within the cutaway 665.

As also shown in FIG. 24, to promote (i) diffusion of the one or more reagents into the fluid sample, or diffusion of sample into the polymer layer containing the reagents (depending on the specific embodiment), (ii) activation of the coagulation cascade by one of two pathways to generate thrombin, (iii) diffusion of the active thrombin through the immobilized substrate and/or reagent polymer layer, (iv) cleavage of the thrombin-cleavable peptide, (v) activation of the detectable moiety, and/or (vi) detection of the detectable moiety by the at least one transducer, the fluid sample may be positioned within the conduit 630 to contact the one or more reagents and/or substrates, the one or more immobilized polymer layers, and/or the one or more sensors, e.g., micro-environment sensors, for a predetermined period of time.

Use of a cartridge is herein illustrated by a specific embodiment in which diagnostic clotting time is determined for a fluid sample, which is introduced into the sample holding chamber of the cartridge followed by cartridge insertion into the cartridge reading device. The cartridge reading device makes electrical contact with the electrodes/sensors through pads, and performs certain diagnostic tests. The diagnostic tests determine whether fluid or sample is present in the conduits using the conductivity electrodes; determine whether electrical short circuits are present in the electrodes; and ensure that the sensor and ground electrodes are thermally equilibrated to, preferably, 37° C. prior to the assay cycle.

In preferred embodiments, a metered portion of the fluid sample, preferably between 4 and 200 μL, more preferably between 4 and 20 μL, and most preferably 7 μL, may be used to carry out the assay, while a sub-volume (between 0.1 and 3.5 uL) thereof may be used to contact the electrodes/sensors. The fluid sample is positioned with respect to the sensor region such that a portion of the fluid sample is positioned over the one or more reagents, the one or more substrates (e.g., immobilized polymer layers), and the one or more sensors comprising one or more transducers and the ground electrode. After the predetermined period of time, e.g., 0-10 seconds of oscillation in the upper or lower section of 630 (or in any of the assay conduits in FIGS. 24, 25, 26, 31, 34, 36 for example) the sample may move to a second conduit or area for subsequent mixing or interactions, or become static or become locked within the conduit(s) or cartridge prior to signal generation. One or more conductivity sensors on the sensor chip may be used to control these processes as discussed with respect to FIGS. 20, 21, 22A, and 22B. During subsequent splitting or diversion of the fluids, there may be passage through pressure- or size-controlled elements. These aspects are described in more detail later on.

During the time of contact between the sample and the sensors, (i) the amending reagents have time to diffuse into the fluid sample or the fluid sample has time to diffuse into the amending reagents (which could be immobilized in some embodiments) in order to promote activation of the coagulation cascade by one of two pathways to generate thrombin, (ii) the active thrombin has time to diffuse through a substrate layer, e.g., an immobilized substrate and/or reagent polymer layer, and cleave the thrombin-cleavable peptide, and (iii) the activated detectable moiety has time to be detected by the at least one transducer.

Fluidic Function and Configurations of Cartridges

In preferred embodiments, a disposable cartridge configuration is provided for that enables two physically separated tests to be conducted simultaneously or subsequently on a single whole blood sample within the same disposable cartridge. The elements of the disposable cartridge configuration include the use of passive fluidic features (e.g., valves, resistances, and fluidic locking elements) in addition to active mechanisms from the analyzer (e.g., a pump) to split the sample into separate conduits/regions such that each sample segment can subsequently be moved to a specific sensor. A number of separate configurations are discussed herein which allow for maintaining the sample in a single channel, splitting the sample into separate fluidic conduits, controlling the fluid movement in each conduit to, for example, mix dried reagent and/or substrate into the sample segment, and/or subsequently park (and lock) the sample over the sensors for analysis. However, it should be understood that various modifications, substitutions, omissions and changes of the configurations can be made without departing from the spirit and scope of the present invention.

In each embodiment below, the sample may be inserted into the inlet chamber of the cartridge by a user. The cartridge is then closed and inserted into the analyzer. The diaphragm pump formed as an air bladder in the cartridge and a mechanical plunger in the analyzer (as discussed with respect to FIG. 24) are used to move the sample throughout the cartridge.

The embodiments of the present invention discussed with respect to FIGS. 25-29 are configured to split a single biological (e.g., whole blood) sample and allow independent mix control of at least two segments of the sample in two conduits where dried reagents and/or substrates specific to each test are located. In accordance with aspects of the present invention, the substrates may or may not be localized (e.g., in accordance with some embodiments, may or may not be immobilized) over the sensor. The reagents and/or substrates dissolved into the sample remain within the conduit where they were formed, therefore eliminating any potential cross-interference between the tests. This is an important element of multiplexing for any two tests where chemical or physical interference could be present (e.g., coagulation tests).

Figure 25:
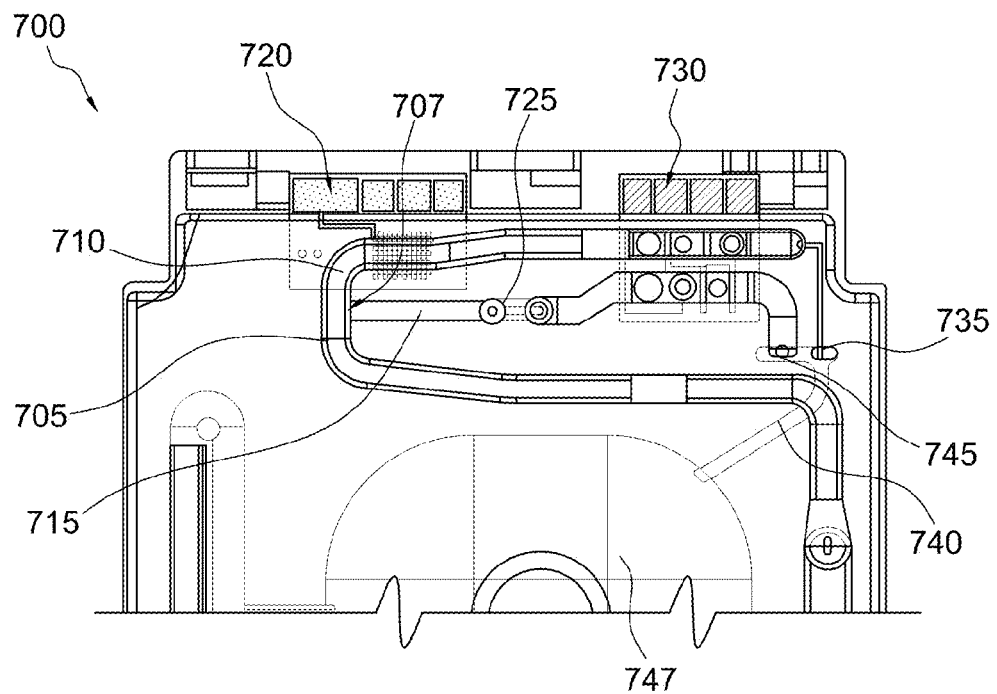
FIGS. 25 and 26 show a top view of a portion of disposable sensing devices in accordance with some aspects of the invention.

As shown in FIG. 25, some embodiments of the present invention pertain to a ground sensor first configuration for a cartridge 700 in which a conduit 705 splits at a junction 707 into a first conduit 710 and a second conduit 715 prior to or upstream of a ground chip 720. The second conduit 715 may comprise a constriction or capillary stop 725 and is configured to pass over a lower region of the sensor chip 730 comprising at least one analyte detection electrode (as described with respect to FIGS. 15 and 16). The first conduit 710 is configured to pass over the ground chip 720 (e.g., ground chip with reference sensor as described with respect to FIG. 17) and the upper region of the sensor chip 730 comprising at least one analyte detection electrode (as described with respect to FIGS. 15 and 16). The cartridge 700 may further comprise at least one fluidic lock mechanism 735 (e.g., a membrane sponge valve, a microchannel capillary, or a micro-array valve) positioned within the first conduit 710, and one or more conduits 740 (e.g., vents), which lead from the first conduit 710 and the second conduit 715 to the cavity 747. In this embodiment, the cavity 747 is configured as a waste chamber (as discussed with respect to FIG. 24). However, it should be understood by those of skill in the art that the one or more conduits 740 may be configured to lead to a waste conduit (as discussed with respect to FIG. 24).

Figure 26:
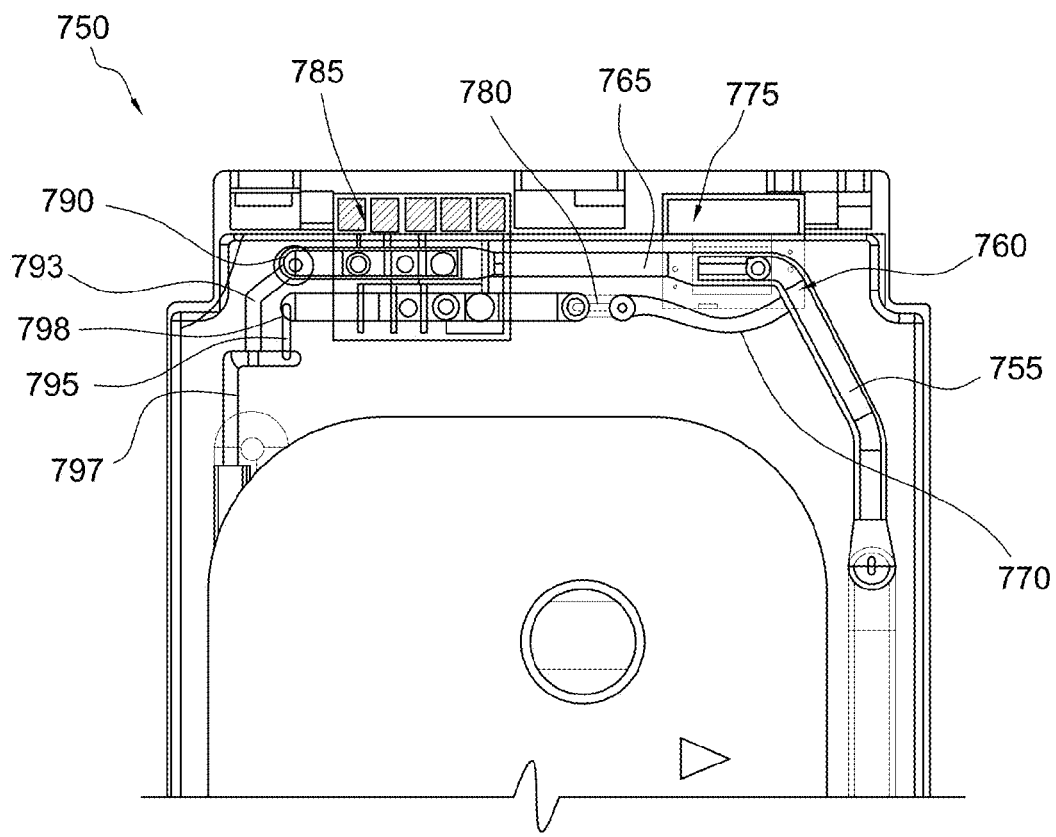

FIG. 26 shows an alternative ground sensor first configuration for a cartridge 750 in which the conduit 755 splits at a junction 760 into a first conduit 765 and a second conduit 770 prior to or upstream of a ground chip 775. The second conduit 770 may comprise a constriction or capillary stop 780 and is configured to pass over a lower region of the sensor chip 785 comprising at least one analyte detection electrode (as described with respect to FIGS. 15 and 16). The first conduit 765 is configured to pass over the ground chip 775 (e.g., ground chip with reference sensor as described with respect to FIG. 17) and the upper region of the sensor chip 785 comprising at least one analyte detection electrode (as described with respect to FIGS. 15 and 16). The cartridge 750 may further comprise at least one fluidic lock mechanism 790 positioned within the first conduit 765. And one or more conduits 793 and 795 (e.g., vents), which lead from the first conduit 765 and the second conduit 770 respectively to a waste conduit 797 (as discussed with respect to FIG. 24).

Figure 27:
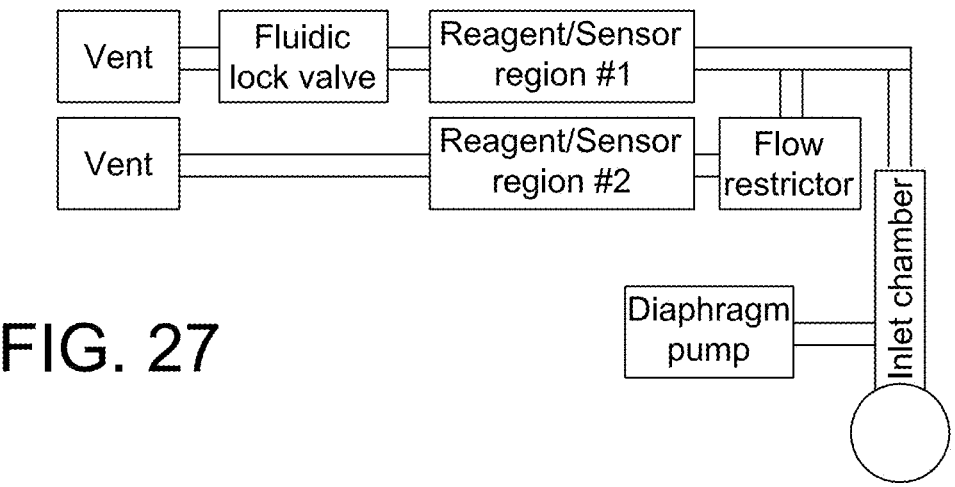
FIGS. 27-29 show advanced microfluidic systems in accordance with some aspects of the invention.

As shown in FIG. 27, during operation of the cartridges 700 and 750, the fluid or biological sample is moved using the bi-directional diaphragm pump (as described with respect to FIG. 24) from the inlet or sample holding chamber to the conduits 705/755. The biological sample is split into a first portion and a second portion at the junction 707/760 (e.g., a T-junction). In preferred embodiments, the constriction or capillary stop 725/780 (e.g., a capillary burst valve or fluidic resistance/constriction) positioned within the second conduit 715/770 causes the sample to preferentially fill the first conduit 710/765 and move over the ground chip 720/775 and the at least one electrode (e.g., an aPTT electrode) within the upper region of the sensor chip 730/785. The diaphragm pump can therefore move a first portion of the sample back and forth in the first conduit 710/765 to dissolve and mix the reagent and/or substrate into sample, while a second portion of the sample in the second conduit 715/770 neither vacates the second conduit 715/770 nor moves to the sensor chip 730/785. Once adequate mixing has been achieved in the first conduit 710/765, the first portion of the sample is pushed over the sensor chip 730/785 to the fluidic lock mechanism 735/790 (e.g., a membrane "sponge valve" or a microchannel formed in either the double-sided adhesive or one of the molded plastic components), which provides pressure resistance and effectively locks the first portion of the sample into the first conduit 710/765. Analysis in the first conduit 710/765 can thereafter begin. As the pressure resistance in the first conduit 710/765 increases significantly, the remaining second portion of the sample is forced through the constriction or capillary stop 725/780 in the second conduit 715/770. A similar back and forth mixing process can then be applied to the second conduit 715/770. Once the reagent and/or substrate is mixed into the second portion of the sample, the second portion of the sample can be positioned over the sensor chip 730/785 and analysis in the second conduit 715/770 can begin. For example, the second portion can be moved through the second conduit 715/770 over at least one electrode (e.g., a PT electrode) within the lower region of the sensor chip 730/785. In accordance with aspects of the present invention, the electrodes within the upper and lower region of the sensor chip 730/785 may be formed with or without immobilization of the reagent/substrate using one or more of the arrangements as discussed with respect to FIGS. 2, 3, 4, 7A, 7B, 7C and 9.

Figure 28:
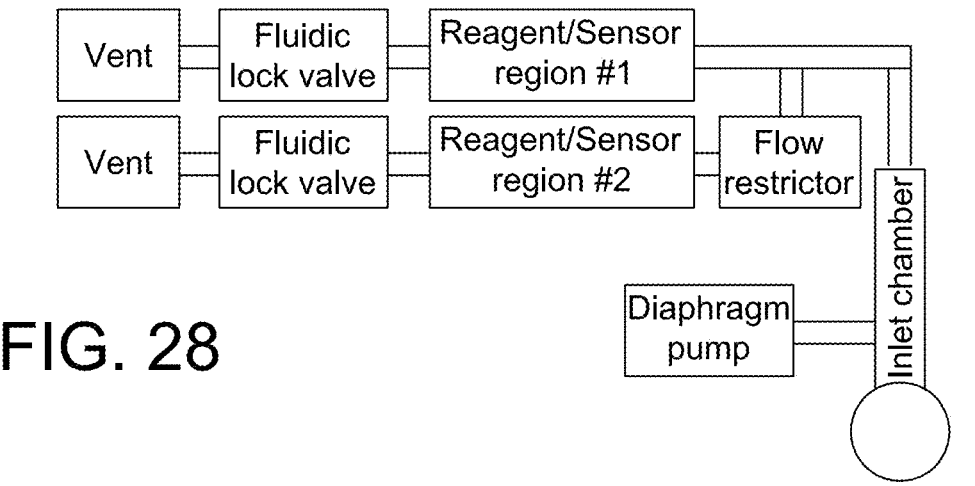

As shown in FIG. 28, during additional operation of the cartridges 700 and 750 the fluid or biological sample may be moved using the bi-directional diaphragm from the inlet or sample holding chamber to the sensor chip 730/785 (as described with respect to FIG. 24). Additionally, once the reagent and/or substrate is mixed into the second portion of the sample, the second portion of the sample is pushed over the sensor chip 730/785 to an additional fluidic lock mechanism 745/798 (shown in FIGS. 25 and 26) (e.g., a membrane "sponge valve" or a microchannel formed in either the double-sided adhesive or one of the molded plastic components), which provides pressure resistance and effectively locks the second portion of the sample into the second conduit 715/770. Once the second portion of the sample is locked in position over the sensor chip 730/785, analysis in the second conduit 715/770 can begin.

Figure 29:
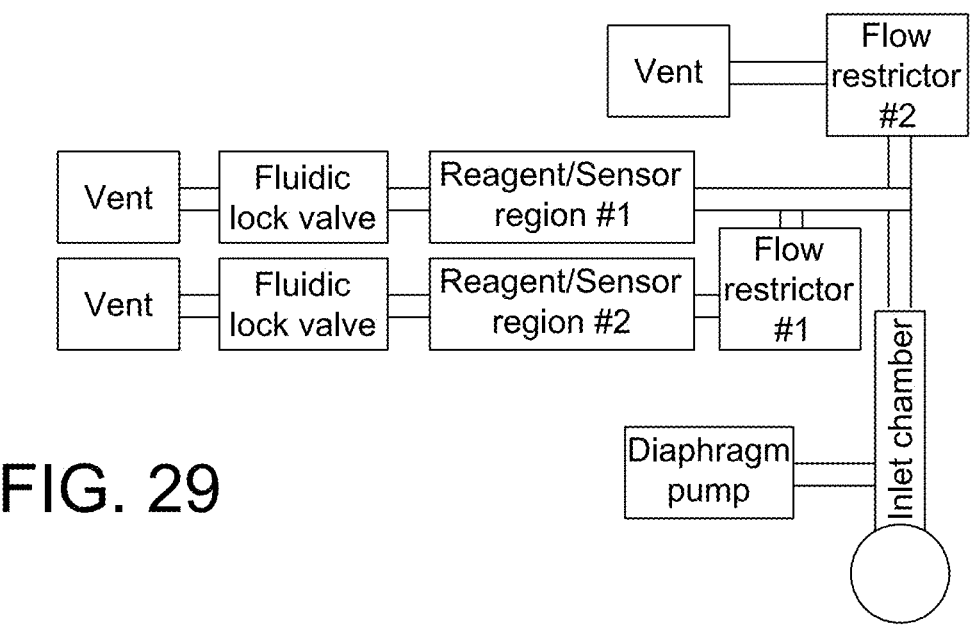

As shown in FIG. 29, during additional operation of the cartridges 700 and 750 the fluid or biological sample may be moved using the bi-directional diaphragm from the inlet or sample holding chamber to the conduits 705/755. However, prior to the sample being moved to the junction 707/760, the sample may be moved through an additional junction (e.g., T-junction) (not shown in FIGS. 25 and 26). The additional junction is configured to separate the first conduit 710/765 and the second conduit 715/770 from a relief conduit (e.g., a vent), which has a constriction or capillary stop (e.g., a capillary burst valve or fluidic resistance/constriction) to divert flow of the sample through the junction 707/760. Any residual pressure or movement of the sample will then proceed into the relief conduit. In preferred embodiments, the additional constriction or capillary stop in the relief conduit is designed such that it has a lower pressure resistance than the fluidic locking features in the first conduit 710/765 and/or the second conduit 715/770.

Figure 30:
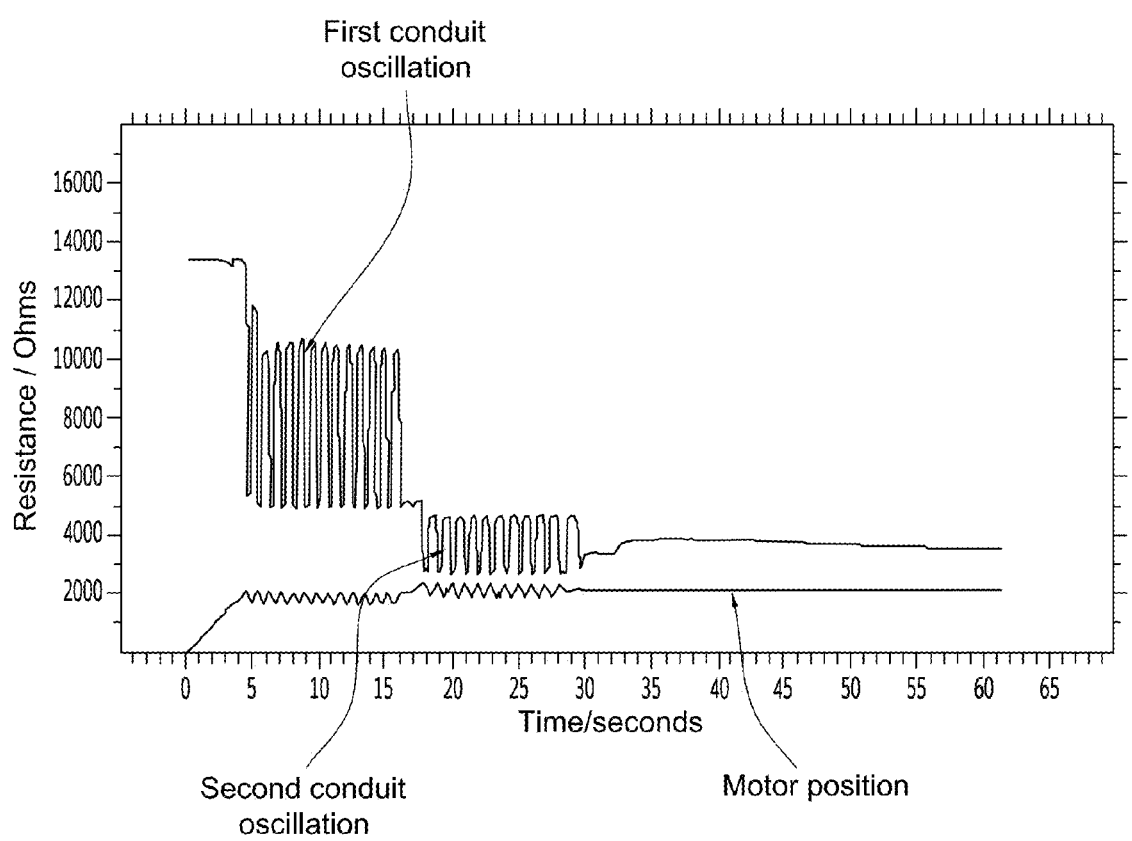
FIG. 30 shows a graph of independent mixing control in accordance with aspects of the invention.

As shown in FIG. 30, the mixing within the conduits may be performed by oscillating the first and second portions of the sample over the electrodes using the multi-conduit conductometric sensors to determine and maintain positioning of the sample as discussed herein. In some embodiments, the first portion of the biological sample is mixed first to initiate a reaction between the first portion of the biological sample and the reagent and/or substrate within the first conduit prior to initiation of a reaction between the second portion of the biological sample and the reagent and/or substrate within the second conduit. For example, an aPTT test conventionally requires a longer test time than that of the PT test, and thus an aPTT test performed within the first conduit could be started earlier than that of the PT test performed within the second conduit such that the tests are completed at approximately the same time.

As should be understood, the ground sensor first design for the cartridges 700 and 750 advantageously provides for a single cartridge capable of performing simultaneously or subsequently two independent assays (e.g., PT and aPTT) within two separate conduits. In embodiments in which mixing is required or advantageous, the features of the cartridges 700 and 750 allow for independent mixing control within the first and second conduits without concern for cross-activation of the cascade pathways or other cross-electrode interference once the one or more reagents have become exposed to the biological sample because the sensors are physically separate from one another via use of at least the first and second conduits.

The embodiments of the present invention discussed with respect to FIGS. 31-35 are configured to split a single biological (e.g., whole blood) sample into two segments in two conduits where dried reagents and/or substrates specific to each test are located. The primary difference between the configurations discussed with respect to FIGS. 31-35 to that of FIGS. 25-29 is that in the configurations of FIGS. 31-35 the sample is pushed over the sensors and locked in place and the reagents and/or substrates located on the sensors are specifically designed to dissolve into the sample by passive diffusion or remain within an immobilization layer. In the example of performing a coagulation analysis, the activation of the cascade pathways and detection thereof occurs at a high concentration region in close proximity to the sensors. The reagents and/or substrates dissolved into the sample or contained in the immobilized layer remain within the conduit where they were printed, therefore eliminating any potential cross-interference between the tests (data not shown). This is an important element of multiplexing for any two tests where chemical or physical interference could be present (e.g., coagulation tests).

Figure 31:
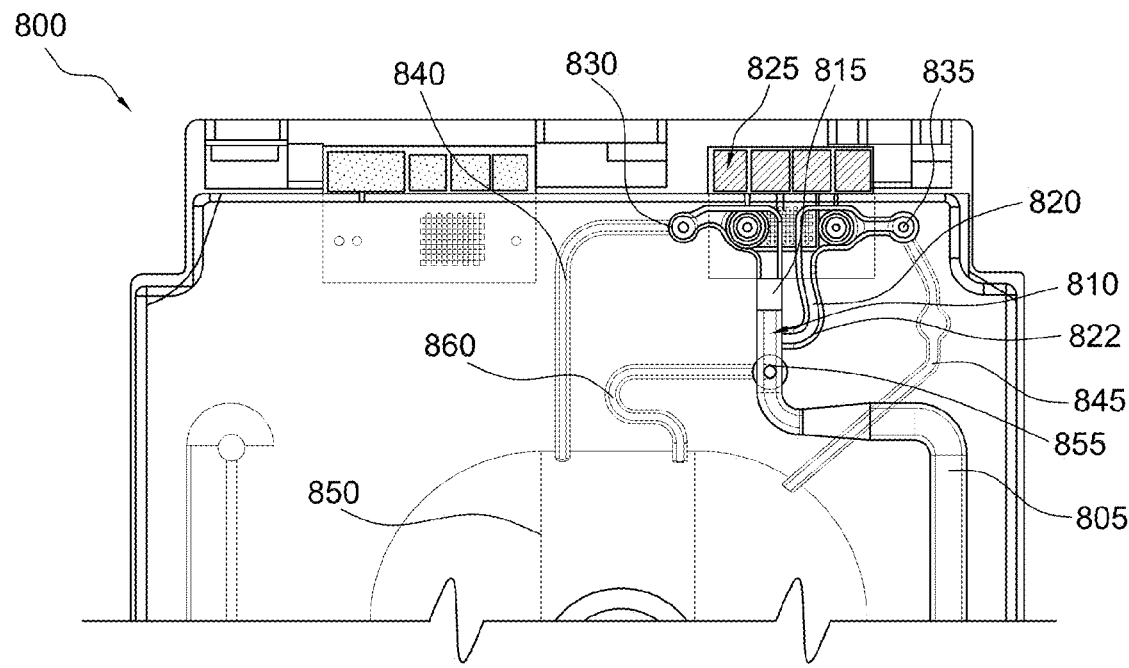
FIG. 31 shows a top view of a portion of a disposable sensing device in accordance with some aspects of the invention.

As shown in FIG. 31, some embodiments of the present invention pertain to an integrated ground sensor and split sensor conduit design for a cartridge 800 in which a conduit 805 splits at a junction 810 into a first conduit 815 and a second conduit 820 prior to or upstream of a ground/sensor chip 825. The first conduit 815 is configured to pass over a first region of the ground/sensor chip 825 (as discussed with respect to FIG. 18) comprising a portion of the reference electrode and at least one analyte detection electrode (e.g., an aPTT electrode). The second conduit 820 comprises a constriction or capillary stop 822 and is configured to pass over a second region of the sensor chip 825 (as discussed with respect to FIG. 18) comprising another portion of the reference electrode and at least one other analyte detection electrode (e.g., a different analyte detection electrode, such as a PT electrode). In accordance with aspects of the present invention, the analyte detection electrodes within the first conduit 815 and the second conduit 820 may be formed with or without immobilization of the reagent/substrate using one or more of the arrangements as discussed with respect to FIGS. 2, 3, 4, 7A, 7B, 7C and 9.

The cartridge 800 may further comprise at least two fluidic barrier mechanisms 830 and 835 (e.g., a fluidic lock mechanism, a capillary stop, or a fluidic constriction) positioned within the first conduit 815 and the second conduit 820 respectively, and one or more conduits 840 and 845 (e.g., vents), which lead from the first conduit 815 and the second conduit 820 respectively to a cavity 850. In this embodiment, the cavity 850 is configured as a waste chamber (as discussed with respect to FIG. 24). However, in alternative embodiments the one or more conduits 840 and 845 may be configured to lead to a waste conduit (as discussed with respect to FIG. 24).

Figure 32:
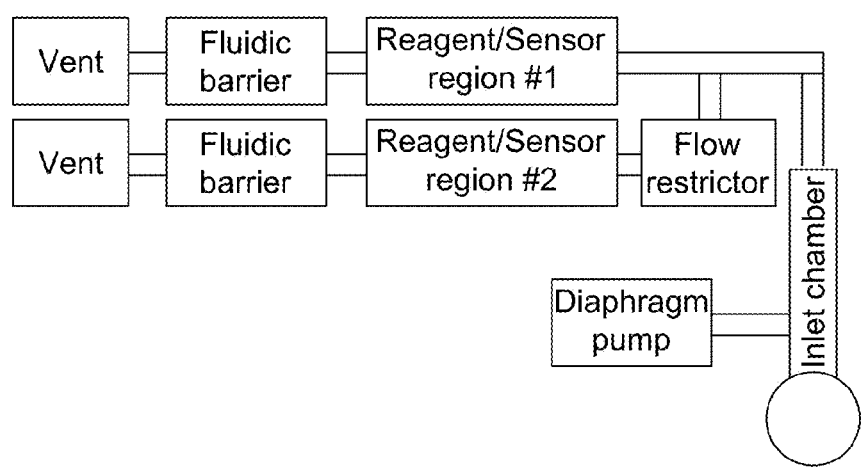
FIGS. 32 and 33 show advanced microfluidic systems in accordance with some aspects of the invention.

As shown in FIG. 32, during operation of the cartridge 800, the fluid or biological sample is moved using the bi-directional diaphragm pump (as described with respect to FIG. 24) from the inlet or sample holding chamber to the conduit 805. The biological sample is split into a first portion and a second portion at the junction 810 (e.g., a T-junction). In preferred embodiments, the constriction or capillary stop 822 (e.g., a capillary burst valve or fluidic resistance/constriction) positioned within the second conduit 820 causes the sample to preferentially fill the first conduit 815 and move over the first region of the ground/sensor chip 825. The first portion of the sample is pushed over the ground/sensor chip 825 to the fluidic barrier mechanism 830 (e.g., a membrane "sponge valve" or a microchannel formed in either the double-sided adhesive or one of the molded plastic components), which provides pressure resistance greater than that of the second conduit 820, and effectively locks the first portion of the sample into the first conduit 815. Analysis in the first conduit 815 can thereafter begin. As the pressure resistance in the first conduit 815 increases significantly, the remaining second portion of the sample is forced through the constriction or capillary stop 822 in the second conduit 820. Similarly, the second portion of the sample is pushed over the ground/sensor chip 825 to the fluidic barrier mechanism 835 (e.g., a membrane "sponge valve" or a microchannel formed in either the double-sided adhesive or one of the molded plastic components), and effectively locks the second portion of the sample into the second conduit 820. Analysis in the second conduit 820 can thereafter begin.

Figure 33:
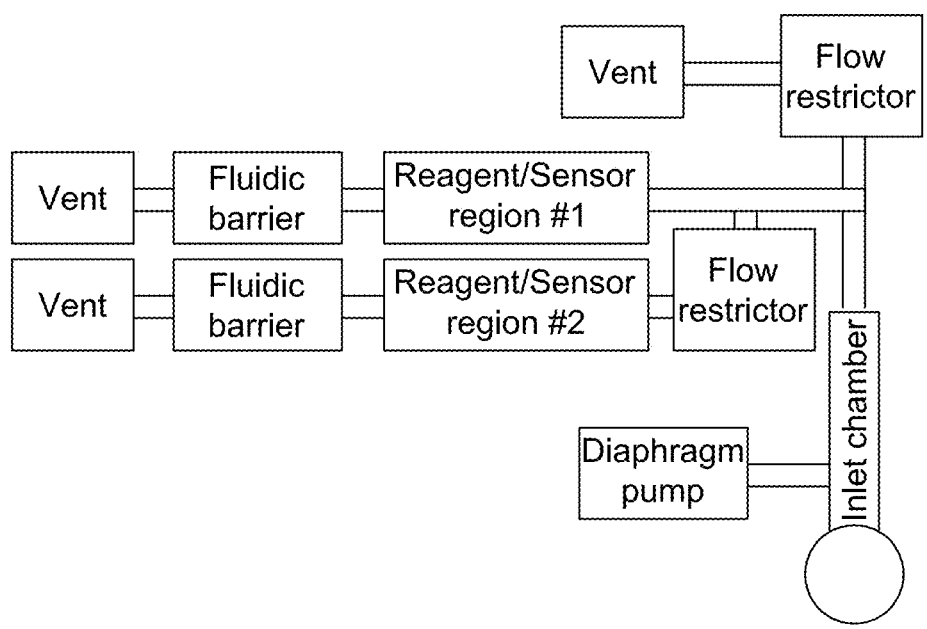

As shown in FIG. 33, during additional operation of the cartridge 800 the fluid or biological sample may be moved using the bi-directional diaphragm from the inlet or sample holding chamber to the conduit 805. However, prior to the sample being moved to the junction 810, the sample may be moved through an additional junction 855 (e.g., a T-junction) (shown in FIG. 31). The additional junction 855 (e.g., T-junction) is configured to separate the first conduit 810 and the second conduit 820 from a relief conduit 860 (e.g., a vent), which has a constriction or capillary stop (e.g., a capillary burst valve or fluidic resistance/constriction) to divert flow of the sample through the junction 810. Any residual pressure or movement of the sample will then proceed into the relief conduit 860. In preferred embodiments, the additional constriction or capillary stop in the relief conduit is designed such that it has a lower pressure resistance than the fluidic barrier mechanisms in the first and second conduits 815 and 820.

As should be understood by those of ordinary skill in the art, the integrated ground sensor and split sensor conduit design for the cartridge 800 advantageously provides for a single cartridge capable of performing simultaneously or subsequently two independent assays (as should be understood the assays may be different or the same, e.g., PT and aPTT, PT and PT, aPTT and aPTT, etc) within two separate conduits without the requirement of mixing the biological sample with the reagent and/or substrate. In accordance with aspects of this embodiment, the features of the cartridge 800 allow for performing two separate analytical tests within the first and second conduits 815 and 820 without concern for cross-activation of the cascade pathways or other cross-electrode interference once the one or more reagents have become exposed to the biological sample because the electrodes are physically separate from one another via use of at least the first and second conduits 815 and 820. Moreover the integrated ground sensor design for the cartridge 800 provides for a simpler more compact cartridge design than that of the ground sensor first designs described above because the design eliminates the space requirement for a completely separate ground sensor and additional length of conduit necessary to move the biological sample to the separate ground sensor.

Figure 34:
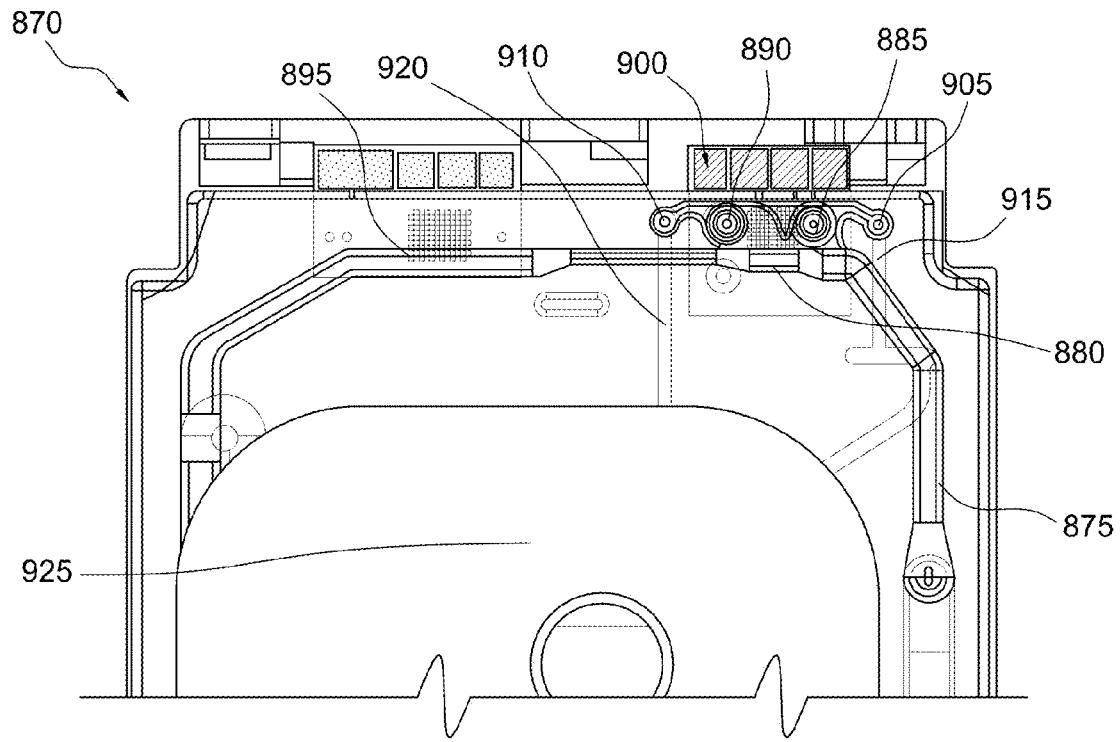
FIG. 34 shows a top view of a portion of a disposable sensing device in accordance with some aspects of the invention.

As shown in FIG. 34, alternative embodiments of the present invention pertain to an integrated ground sensor and split conduit design for a cartridge 870 comprising a conduit 875 with a junction 880 (e.g., T-junction). The junction 880 is configured to separate a first sensor conduit 885 and a second conduit 890 from a relief conduit 895 (e.g., a vent). The first sensor conduit 885 is configured to pass over a first region of a ground/sensor chip 900 (as discussed with respect to FIG. 18) comprising a portion of a reference electrode and at least one analyte detection electrode (e.g., an aPTT electrode). The second sensor conduit 890 is configured to pass over a second region of the sensor chip 900 (as discussed with respect to FIG. 18) comprising another portion of the reference electrode and at least one different analyte detection electrode (e.g., a PT electrode). In accordance with aspects of the present invention, the analyte detection electrodes within the first sensor conduit 885 and the second sensor conduit 890 may be formed with or without immobilization of the substrate using one or more of the arrangements as discussed with respect to FIGS. 2, 3, 4, 7A, 7B, 7C and 9.

The cartridge 870 may further comprise at least two fluidic barrier mechanisms 905 and 910 positioned within the first sensor conduit 885 and the second sensor conduit 890 respectively, and one or more conduits 915 and 920 (e.g., vents), which lead from the first sensor conduit 885 and the second conduit 890 respectively to a cavity 925. In this embodiment, the cavity 925 is configured as a waste chamber (as discussed with respect to FIG. 24). However, in alternative embodiments the one or more conduits 915 and 920 may be configured to lead to a waste conduit (as discussed with respect to FIG. 24).

Figure 35:
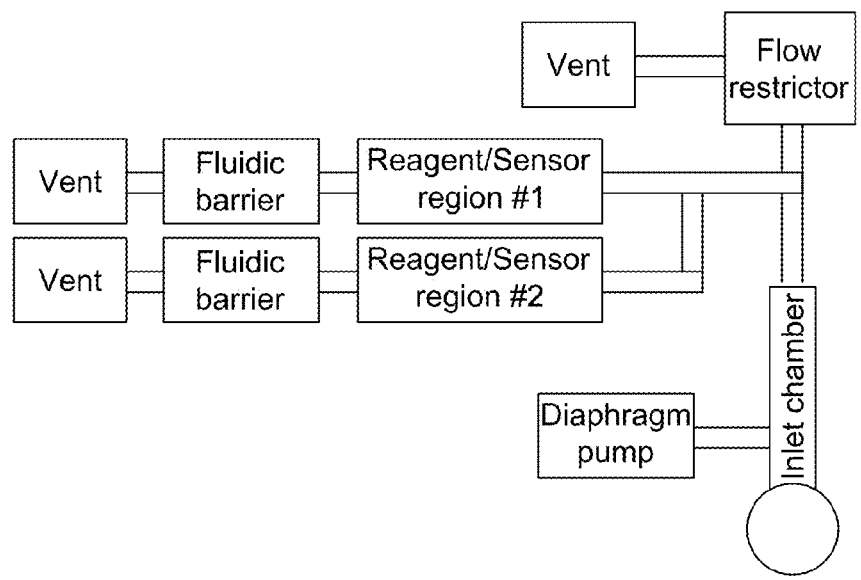
FIG. 35 shows an advanced microfluidic system in accordance with some aspects of the invention.

As shown in FIG. 35, during operation of the cartridges 870, the fluid or biological sample is moved using the bi-directional diaphragm pump (as described with respect to FIG. 24) from the inlet or sample holding chamber to the conduit 875 and through the junction 880. The relief conduit 895 (e.g., a vent) has a constriction or capillary stop (e.g., a capillary burst valve or fluidic resistance/constriction) to divert flow of the sample to the first sensor conduit 885 and the second sensor conduit 890. A first portion of the sample is pushed over the ground/sensor chip 900 to the fluidic barrier mechanism 905 (e.g., a membrane "sponge valve" or a microchannel formed in either the double-sided adhesive or one of the molded plastic components), which effectively locks the first portion of the sample into the first sensor conduit 885. Analysis in the first conduit 885 can thereafter begin. A second portion of the sample is pushed over the ground/sensor chip 900 to the fluidic barrier mechanism 910 (e.g., a membrane "sponge valve" or a microchannel formed in either the double-sided adhesive or one of the molded plastic components), which effectively locks the second portion of the sample into the second sensor conduit 890. Analysis in the second conduit 890 can thereafter begin. Any residual pressure or movement of the sample will then proceed into the relief conduit 895. In preferred embodiments, the constriction or capillary stop in the relief conduit is designed such that it has a lower pressure resistance than the fluidic barrier mechanisms in the first and second sensor conduits 885 and 890.

As should be understood, the alternative integrated ground sensor and split conduit design for the cartridge 870 advantageously provides for a single cartridge capable of performing simultaneously or subsequently two independent assays (as should be understood the assays may be different or the same, e.g., PT and aPTT, PT and PT, aPTT and aPTT, etc.) within two separate sensor conduits without the requirement of mixing the biological sample with the reagent and/or substrate. In accordance with aspects of this embodiment, the features of the cartridge 870 allow for performing two separate analytical tests within the first and second sensor conduits 885 and 890 without concern for cross-activation of the cascade pathways or other cross-electrode interference once the one or more reagents have become exposed to the biological sample because the electrodes are physically separate from one another via use of at least the first and second sensor conduits 885 and 890. Moreover, the integrated ground sensor design for the cartridge 870 provides for a simpler more compact cartridge design than that of the ground sensor first designs described above because the design eliminates the space requirement for a completely separate ground sensor and additional length of conduit necessary to move the biological sample to the separate ground sensor. In addition, the sample volume required to cover the complete sensor circuit is significantly reduced.

Figure 36:
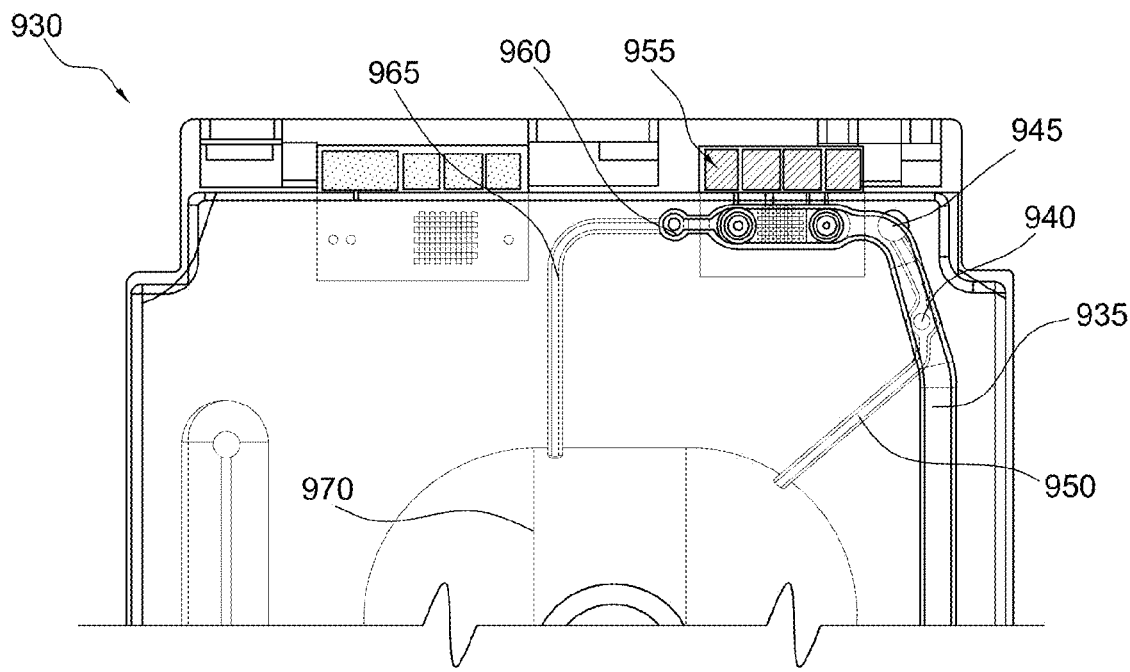
FIG. 36 shows a top view of a portion of a disposable sensing device in accordance with some aspects of the invention.
Figure 37:
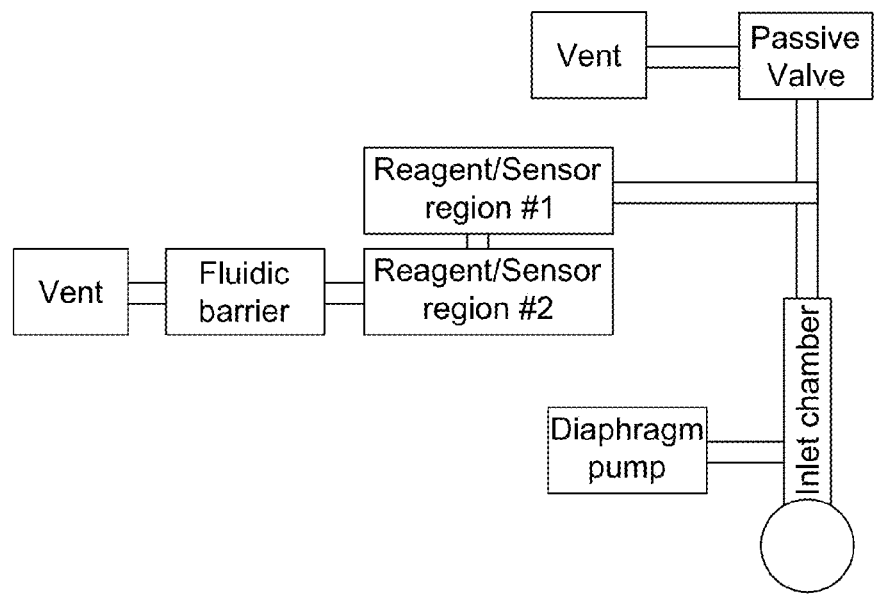
FIGS. 37 and 38 show advanced microfluidic systems in accordance with some aspects of the invention.
Figure 38:
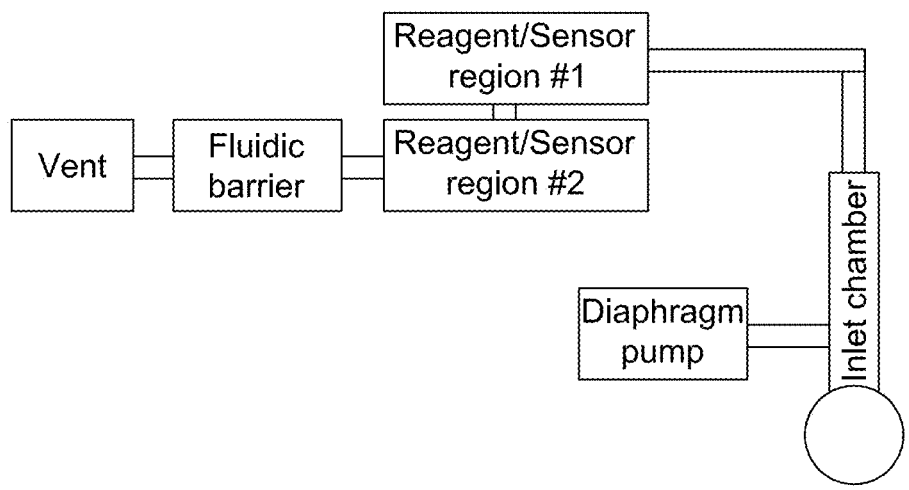

The embodiments of the present invention discussed with respect to FIGS. 36-38 are configured to maintain a single biological (e.g., whole blood) sample in a single conduit where dried reagents and/or substrates specific to each test are located. The primary difference between the configurations discussed with respect to FIGS. 36-38 to that of FIGS. 27-29 is that in the configurations of FIGS. 36-38 the sample is maintained in a single conduit and pushed over the sensors in series and locked or held in place and the reagents and/or substrates located on the sensors are specifically designed to dissolve into the sample by passive diffusion or remain within an immobilization layer. In the example of performing a coagulation analysis, the activation of the cascade pathways and detection thereof occurs at a high concentration region in close proximity to the sensors. The reagents and/or substrates dissolved into the sample remain near the sensors where they were printed, therefore eliminating any potential cross-interference between the tests. This is an important element of multiplexing for any two tests where chemical or physical interference could be present (e.g., coagulation tests).

As shown in FIG. 36, some embodiments of the present invention pertain to an integrated ground sensor and single conduit design for a cartridge 930 comprising a conduit 935 with a junction 940 (e.g., T-junction). The junction 940 is configured to separate a single conduit sensor conduit 945 from a relief conduit 950 (e.g., a vent). The single sensor conduit 945 is configured to pass over a first region of a ground/sensor chip 955 (as discussed with respect to FIG. 18) comprising at least one analyte detection electrode (e.g., an aPTT electrode), a second region comprising at least a portion of the reference electrode, and a third region comprising at least one same or different analyte detection electrode (e.g., a PT electrode). In accordance with aspects of the present invention, the analyte detection electrodes within the single conduit sensor conduit 945 are formed with immobilization of the reagent/substrate using one or more of the arrangements as discussed with respect to FIGS. 4, 7A, 7B, 7C and 9.

The cartridge 930 may further comprise a fluidic barrier mechanism 960 positioned within the sensor conduit 945, and a conduit 965 (e.g., vents) that leads from the sensor conduit 945 to a cavity 970. In this embodiment, the cavity 970 is configured as a waste chamber (as discussed with respect to FIG. 24). However, in alternative embodiments the conduit 965 may be configured to lead to a waste conduit (as discussed with respect to FIG. 24).

As shown in FIGS. 36 and 37, during operation of the cartridge 930, the fluid or biological sample is moved using the bi-directional diaphragm pump (as described with respect to FIG. 24) from the inlet or sample holding chamber to the conduit 935 and through the junction 940. The relief conduit 950 (e.g., a vent) has a constriction or capillary stop (e.g., a capillary burst valve or fluidic resistance/constriction) to divert flow of the sample to the sensor conduit 945. The sample is pushed over the ground/sensor chip 955 to the fluidic barrier mechanism 960 (e.g., a membrane "sponge valve" or a microchannel formed in either the double-sided adhesive or one of the molded plastic components), which effectively locks the sample into the sensor conduit 945. Analysis in the sensor conduit 945 can thereafter begin. Any residual pressure or movement of the sample will then proceed into the relief conduit 950. In preferred embodiments, the constriction or capillary stop in the relief conduit 950 is designed such that it has a lower pressure resistance than the fluidic barrier mechanisms in the sensor conduit 945.

As shown in FIGS. 36 and 38, during alternative operation of the cartridge 930, the fluid or biological sample may be moved using the bi-directional diaphragm from the inlet or sample holding chamber to the conduit 935. The sample is thereafter pushed over the ground/sensor chip 955 to the fluidic barrier mechanism 960 (e.g., a membrane "sponge valve" or a microchannel formed in either the double-sided adhesive or one of the molded plastic components), which effectively locks the sample into the sensor conduit 945. Analysis in the sensor conduit 945 can thereafter begin.

As should be understood, the integrated ground sensor and single conduit design for the cartridge 930 advantageously provides for a single cartridge capable of performing simultaneously or subsequently two independent assays (e.g., as should be understood the assays may be different or the same, e.g., PT and aPTT, PT and PT, aPTT and aPTT, etc) within a single conduit without the requirement of mixing the biological sample with the reagent and/or substrate. In accordance with aspects of this embodiment, the features of the cartridge 930 allow for performing two separate analytical tests within the sensor conduit 945 without concern for cross-activation of the cascade pathways or other cross-electrode interference once the one or more reagents have become exposed to the biological sample because the analyte detection electrodes are micro-environment sensors with a localized (e.g., immobilized) reagent/substrate formed using one or more of the arrangements as discussed herein in detail. Moreover the integrated ground sensor design for the cartridge 930 provides for a simpler more compact cartridge design than that of the ground sensor first designs described above because the design eliminates the space requirement for a completely separate ground sensor and additional length of conduit necessary to move the biological sample to the separate ground sensor. In addition, the sample volume required to cover the complete sensor circuit is significantly reduced.

Figure 39:
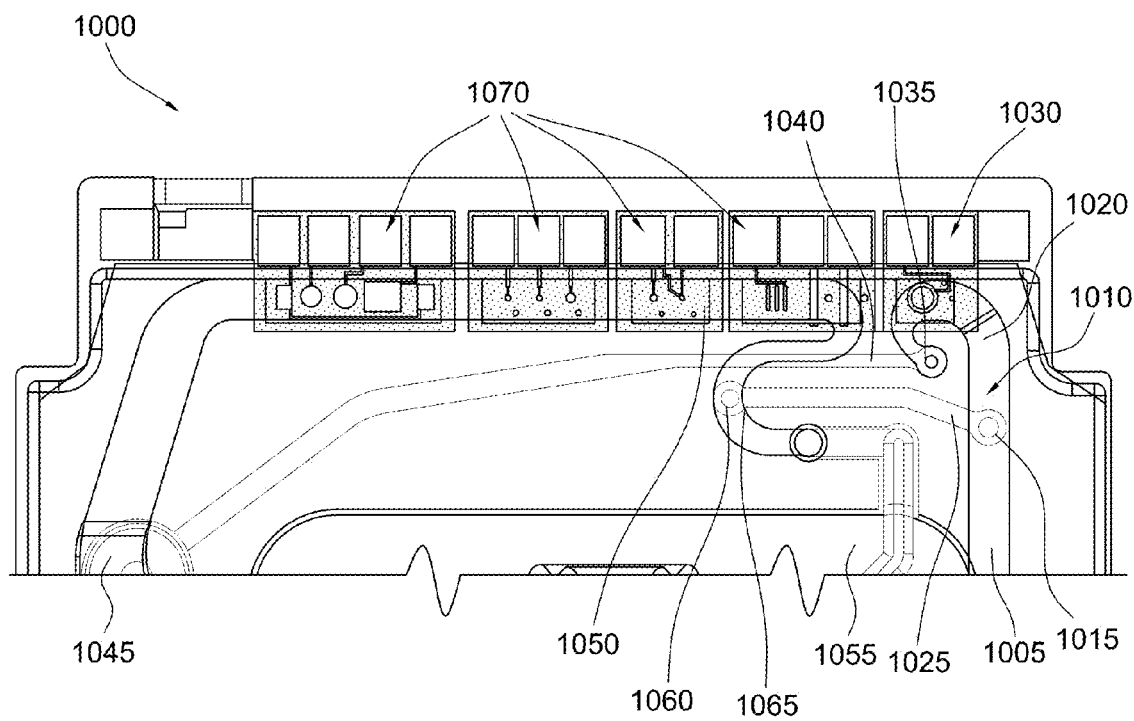
FIG. 39 shows a top view of a portion of a disposable sensing device in accordance with some aspects of the invention.

The embodiments of the present invention discussed with respect to FIG. 39 are configured to split a single biological (e.g., whole blood) sample and allow for multiple physically separated tests (e.g., coagulation tests and analytical chemistry tests) to be conducted simultaneously or subsequently on a single whole blood sample within the same disposable cartridge. In some embodiments, independent mix control is provided for at least two segments of the sample in two conduits where dried reagents and/or substrates specific to each test may be located. In accordance with aspects of the present invention, the substrates may or may not be localized (e.g., immobilized) over the sensors. The reagents and/or substrates dissolved into the sample remain within the conduit and close to the sensor where they were printed or deposited, therefore eliminating any potential cross-interference between the tests. This is an important element of multiplexing for any two tests where chemical or physical interference could be present (e.g., coagulation tests and analytical chemistry tests).

As shown in FIG. 39, some embodiments of the present invention pertain to a multiple sensor configuration for a cartridge 1000 comprising a conduit 1005 with a junction 1010 (e.g., T-junction). The junction 1010 may comprise a first constriction or capillary stop 1015 and is configured to separate a first sensor conduit 1020 from an ancillary conduit 1025. The first sensor conduit 1020 is configured to pass over at least a portion of a sensor chip 1030 comprising at least one analyte detection electrode (e.g., a PT electrode). In accordance with aspects of the present invention, the analyte detection electrode within the first sensor conduit 1020 may be formed with or without localization (e.g., immobilization) of a reagent/substrate using one or more of the arrangements as discussed with respect to FIGS. 2, 3, 4, 7A, 7B, 7C and 9. A second constriction or capillary stop 1035 may be positioned within the first sensor conduit 1020, and a conduit 1040 (e.g., vents) may be configured to lead from the first sensor conduit 1020 to a waste conduit 1045 (as discussed with respect to FIG. 24).

The cartridge 1000 may further comprise a second sensor conduit 1050 that connects a cavity 1055 with the waste conduit 1045. The ancillary conduit 1025 connects to the second sensor conduit 1050 at a junction 1060. The junction 1060 may comprise a third constriction or capillary stop 1065. In some embodiments, the first constriction or capillary stop 1015 and the third constriction or capillary stop 1065 are configured larger (e.g., larger in width) than the second constriction or capillary stop 1035 to allow for control of the sample as discussed hereafter in detail. The second sensor conduit 1050 is configured to pass over at least a portion of each of one or more sensor chips 1070 comprising at least one analyte detection electrode (e.g., a sodium or chloride electrode). The one or more sensor chips 1070 may be configured to perform any number of assays, including electrolytes, general chemistries, blood gases and hematology (See, for example, U.S. Pat. Nos. 7,419,821, 6,379,883, 5,514,253, 5,200,051, and 5,096,669, which are incorporated herein by reference in their entireties). For example, the one or more sensor chips 1070 may be configured to perform any number of assays capable of detecting one or more analytes selected from the group consisting of oxygen partial pressure, carbon dioxide partial pressure, total carbon dioxide, pH, potassium, sodium, chloride, glucose, BUN, creatinine, lactate, magnesium, hematocrit, ionized calcium, troponin I, troponin T, CKMB, procalcitonin, bHCG, HCG, NTproBNP, proBNP, BNP, myoglobin, parathyroid hormone, d-dimer, NGAL, galectin-3, and/or PSA, among other analytes. In embodiments in which a substrate is utilized for performing the assay, the at least one analyte detection electrode within the second sensor conduit 1050 may be formed with or without localization (e.g., immobilization) of a reagent/substrate using one or more of the arrangements as discussed with respect to FIGS. 2, 3, 4, 7A, 7B, 7C and 9. In other embodiments that do not utilize a substrate, the at least one analyte detection electrode within the second sensor conduit 1050 may be formed without any substrate.

As shown in FIG. 39, during operation of the cartridge 1000, deformation of a gasket by the analyzer may transmit pressure onto a fluid-containing foil pack filled with a fluid, e.g., approximately 130 μL of analysis/wash solution, control fluid, or calibrant fluid, located in the cavity 1055, rupturing the foil pack, and expelling fluid into the second sensor conduit 1050 and past the third constriction or capillary stop 1065 for subsequent use in sample analysis (as discussed with respect to FIG. 24). In some embodiments, the foil pack is a calibrant package (CALPAK) that contains a calibrant solution. The typical sequence of events includes the CALPAK being ruptured and then the calibration solution passing over the one or more sensor chips 1070 to wet up the one or more sensor chips 1070. Thereafter, the fluid or biological sample is moved using the bi-directional diaphragm pump (as described with respect to FIG. 24) from the inlet or sample holding chamber to the conduit 1005. The biological sample is split into a first portion and a second portion at the junction 1010 (e.g., a T-junction). In preferred embodiments, the first constriction or capillary stop 1015 (e.g., a capillary burst valve or fluidic resistance/constriction) positioned within the ancillary conduit 1025 causes the first portion of the sample to preferentially fill the first sensor conduit 1020 and move over the sensor chip 1030 and the at least one electrode (e.g., a PT electrode). The first portion of the sample within the first sensor conduit 1020 stops at the second constriction or capillary stop 1035, which causes the second portion of the sample to push through the first constriction or capillary stop 1015 and the third constriction or capillary stop 1065. The second portion of the sample fills the second sensor conduit 1050 and moves over one or more sensor chips 1070 and the at least one analyte detection electrode (e.g., a sodium or chloride electrode). In some embodiments, the second portion of the sample may be configured to mix with the analysis/wash solution, control fluid, or calibrant fluid present within the second sensor conduit 1050. To enable mixing of the fluid segments, features, including retention structures such as post arrays, conduit cut-outs, grooves, or dimples, can be designed into second sensor conduit 1050 to retain the analysis/wash solution, control fluid, or calibrant fluid. Alternatively, mixing of the two fluid segments can be accomplished by merging the two streams of fluid from conduit 1025 and the foil-pack 1055 at junction 1060. In other embodiments, the analysis/wash solution, control fluid, or calibrant may have been pumped through the second sensor conduit 1050 to the waste conduit 1045 such that the second portion of the sample does not mix with the analysis/wash solution, control fluid, or calibrant. Furthermore, to minimize carry-over of the analysis/wash solution, control fluid, or calibrant, the cartridge may be designed in such a way as to introduce an air segment between the first fluid and the second portion of the sample. The volume of ancillary conduit 1025 should determine the size of the air gap between the fluid segments.

As should be understood, the multiple sensor configurations for the cartridge 1000 advantageously provide for a single cartridge capable of performing simultaneously or subsequently two independent assays (e.g., PT and an analytical chemistry assay, PT and PT, aPTT and PT, aPTT and aPTT, etc.) within two separate conduits. In embodiments in which mixing is required or advantageous, the features of the cartridge 1000 allow for independent mixing control within the first and second conduits without concern for cross-activation or other cross-electrode interference once the one or more reagents have become exposed to the biological sample because the sensors are physically separate from one another via use of at least the first and second sensor conduits.

Figure 40:
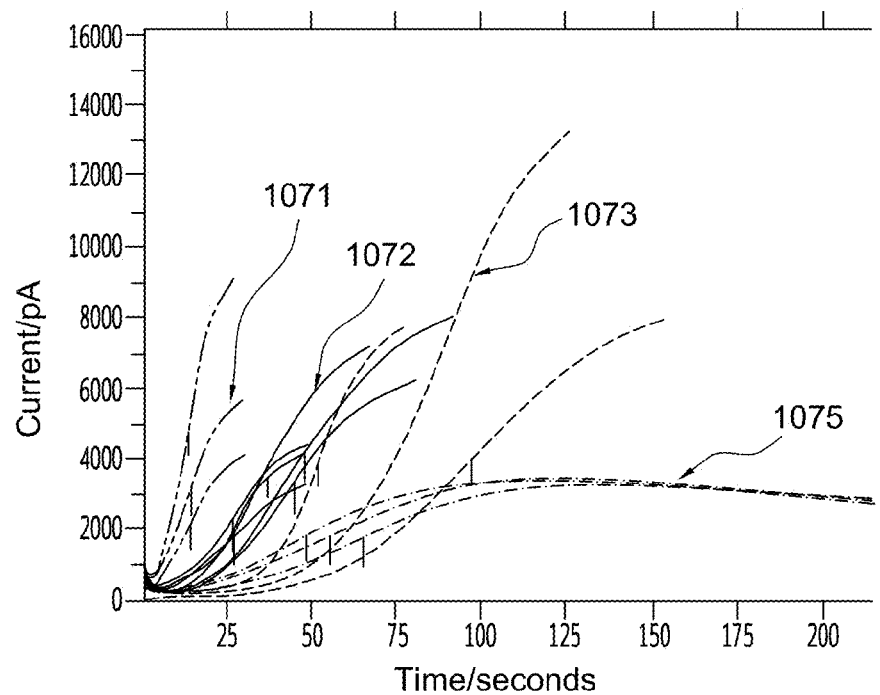
FIGS. 40, 41A, and 41B show graphs that provide empirical evidence for aspects of the present invention.
Figure 41A:
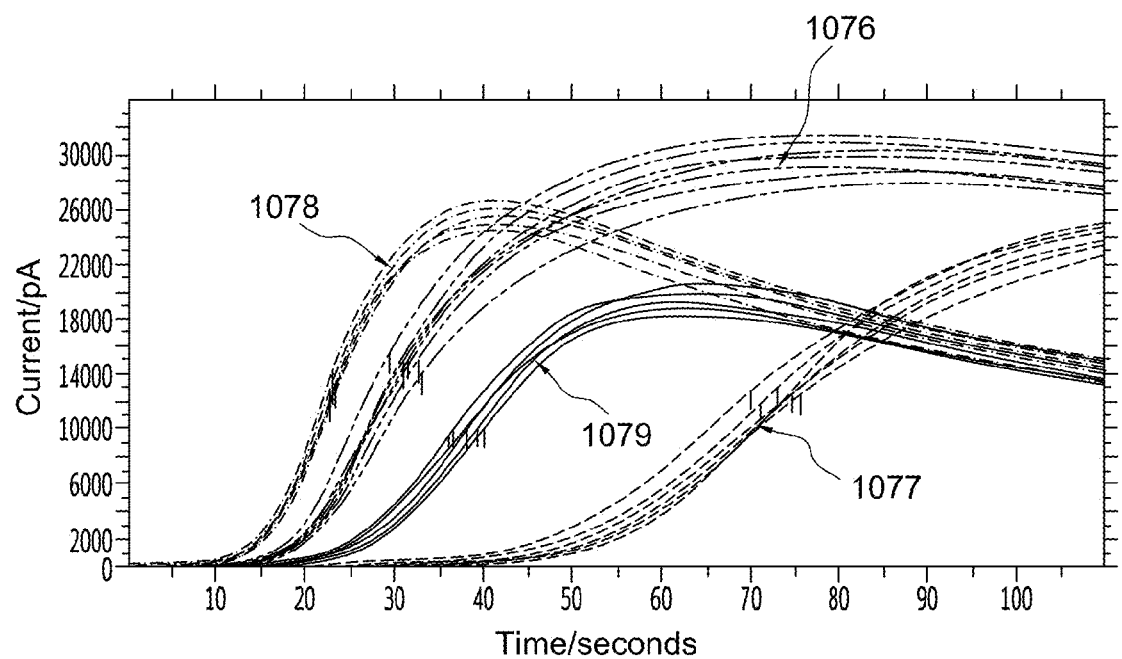
Figure 41B:
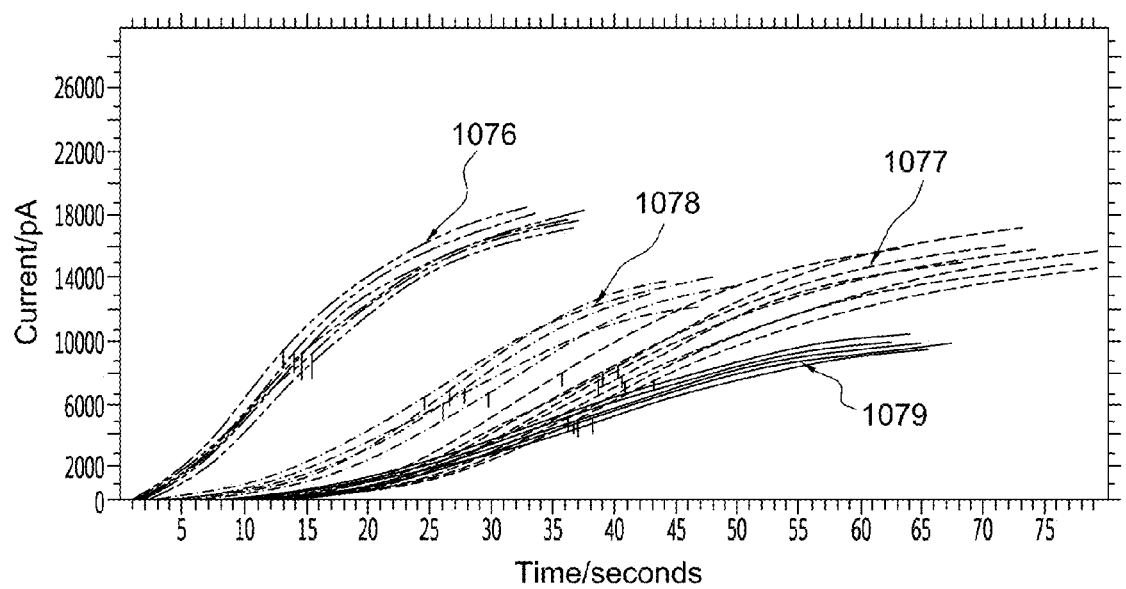

As shown in FIG. 40 where the x-axis is time/seconds and the y-axis is current/pA, embodiments pertaining to independent mix control of a sample in two separate conduits of a cartridge (as shown in FIGS. 25-29 and 39) and fully mixing the reagent/substrate (i.e., no localized micro-environment) are capable of achieving clotting results (for e.g., PT times indicated by the vertical line marked on each of the clot curves) using multiple sample types (whole blood represented by response curves 1071, two levels of factor depleted blood represented by response curves 1072 and 1073, one level of control plasma represented by response curves 1075). As shown in FIG. 41A, embodiments of the present invention pertaining to no mixing of a sample over the immobilized or localized reagents/substrates in one or more conduits of a cartridge (as shown in FIGS. 30-38) are also capable of achieving clotting results using samples (whole blood represented by response curves 1076, factor depleted blood represented by response curves 1077, and two levels of control plasma represented by response curves 1078 and 1079) similar to those used in FIG. 40. As shown in FIG. 41B (whole blood represented by response curves 1076, factor depleted blood represented by response curves 1077, and two levels of control plasma represented by response curves 1078 and 1079), the sensor responses for the embodiments pertaining to mixing of the sample over the immobilized or localized reagents/substrates are also achievable, however resolution of the factor depleted and extended plasma control samples is not as clear as in the immobilized no mixing embodiment (as shown in FIG. 41A). Further, the preference is that the clotting times of whole blood (curves 1071 and 1076) be very close to the normal plasma control clotting times (curves 1072 and 1078); the no mixed, immobilized/localized embodiments reflect this the best, further giving credence to their improvement over the system of FIG. 40. Although no-mixed or mixed versions of the embodiments are possible, the current (pA) generation is higher and variability (pA and clotting time) is lower in the no-mixed version (as shown in FIG. 41A) of the embodiments. These unexpected and more consistent results are directly attributable to the use of the micro-environment sensors as described herein with respect to the no mixing embodiments. The no mixing embodiment in combination with the localized (e.g., immobilized) reagent/substrate print represents a system improvement in the activation/propagation of the coagulation signal in a higher reagent/substrate to lower sample volume ratio, thus producing a faster assay/sensor response time. In addition, localization (e.g., immobilization) of the reagent/substrate print directly over the sensor results in the immediate turnover (oxidation) of the diffused substrate leaving group once generated by active thrombin. This ultimately leads to greater (and more reproducible) current signal being generated directly at the amperometric assay sensor. Finally, the combination of quick thrombin response (evident from the quick rise in curves in FIG. 41A as compared to the slower rise in FIG. 41B) with higher currents and higher reproducibility produces response curves which are more easily and reproducibly analyzed, thus yielding an improved assay (the current embodiment, represented in FIG. 41A) over either of those in FIG. 40 or 41B.

Ground Chip Elimination and Cartridge Identification

In preferred embodiments, the ground chip may be incorporated or integrated into the sensor chip as described in detail herein. A typical ground chip (as described with respect to FIG. 17) may include a ground electrode serving as a return of the sensor chip and four contact pins for cartridge identification (see, e.g., U.S. Pat. No. 7,419,821, which is incorporated herein in its entirety). Accordingly, integration of the ground chip into the sensor chip encompasses moving these two functions into the sensor chip. The advantages of integrating the ground chip with the sensor chip include (i) a simplified manufacturing process since there is one component less to deal with during wafer fabrication, metallization, dicing, and cartridge assembly, (ii) reduced cost, and (iii) reduced sample volume since the sensor conduit can be shortened as shown in a comparison between at least FIGS. 25 and 31.

Figure 42:
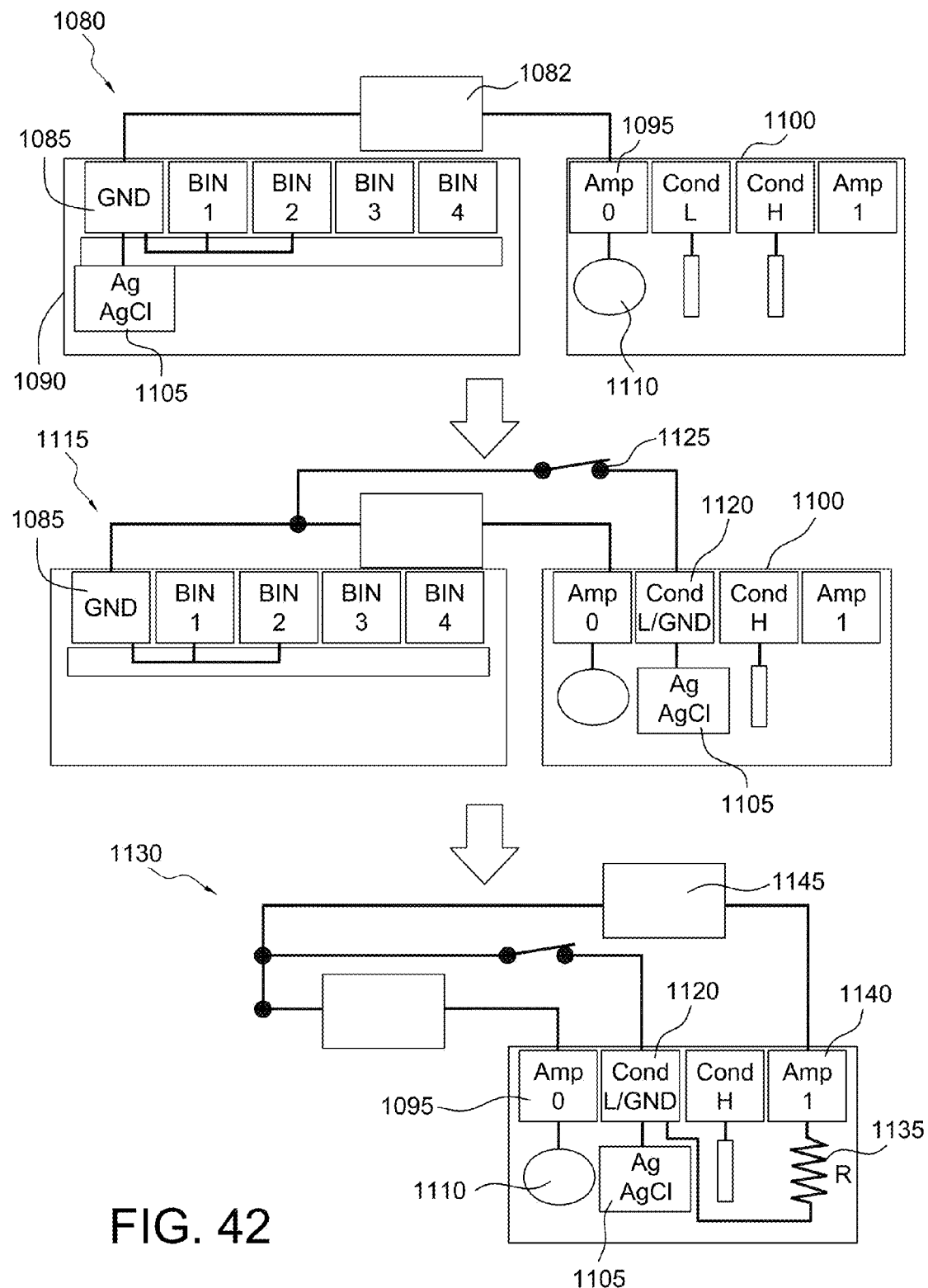
FIGS. 42 and 43 illustrate the principle of operation for eliminating the ground chip in accordance with some aspects of the invention.

As shown in FIG. 42, the separate ground chip and sensor chip arrangement 1080 (e.g., the arrangement shown in FIG. 17) typically functions by using a detector 1082 connected with the ground pin 1085 on the ground chip 1090 and an amperometric pin 1095 on the sensor chip 1100 to detect a difference in current between the reference electrode 1105 and the analyte detection electrode 1110 (e.g., an amperometric electrode). In order to impart the reference electrode functionality into a single sensor chip arrangement 1115 (e.g., the arrangement shown in FIG. 18) the reference electrode 1105 may be integrated with the sensor chip 1100 by connecting the reference electrode 1105 with the conductometric low pin 1120. An electronic switch 1125 may be implemented in the analyzer, which is configured to connect the ground pin 1085 and the conductometric low pin 1120. Accordingly, the reference electrode 1105 can be essentially moved from the ground chip 1090 to the sensor chip 1100.

In order to impart the cartridge identification functionality into a single sensor chip arrangement (e.g., the arrangement shown in FIG. 18), an additional mechanism or means may be included in the arrangement for cartridge identification. As shown in FIG. 42 for a single electrode arrangement 1130, for example, an aPTT only analyte detection electrode 1110, a resistor 1135 can be implemented between an unused amperometric pin 1140 and the conductometric low pin 1120. The analyte detection electrode 1110 may be connected to the amperometric pin 1095, the resistor 1135 may be connected to the unused amperometric pin 1140 and the conductometric low pin 1120, and the reference electrode 1105 may be connected to the conductometric low pin 1120. The resistance of the resistor 1135 may be measured by a detector 1145 (e.g., processor) by applying a small voltage, e.g., 1mV, between the unused amperometric pin 1140 and the conductometric low pin 1120, subsequent to (e.g., immediately after) the cartridge being inserted into the analyzer. The value of the measured resistance can then be used for cartridge identification. For example, each cartridge type (e.g., i-STAT® cartridges EC8+, CG8+, EG7+, CHEM8+, etc.) may be associated with a certain resistance or resistance range such that a measured resistance of the cartridge may be used to identify the type of cartridge using a look-up table.

In some embodiments, the resistor 1135 may be comprised of a metal wire, preferably a gold wire manufactured at a same time as the contact pads and sensor electrode. The gold wire may be as small as 5 µm wide and 0.1 µm thick, which forms an area of 0.5 µm². As the resistivity of gold is 2.44 µΩ-cm, or 0.0244Ω-µm, a 1000 µm long gold wire will have a resistance of 0.0244Ω-µm*1000 µm/0.5 µm²=48.8Ω. After the cartridge is inserted into the analyzer, a small voltage, e.g., 0.5 mV may be applied and a current of around 10 uA may be generated and detected by the analyzer. To minimize the power consumption, optionally the gold wire could be longer, the applied voltage could be lower, or the time for the application of the voltage could be shorter.

In an alternative embodiment, the single electrode arrangement 1130 may include a PT only analyte detection electrode 1110 rather than an aPTT only analyte detection electrode 1110. In accordance with this aspect of the present invention, the length of the gold wire may be increased to about 10 cm, which increases the resistance of the gold wire to around 5000Ω, in order to distinguish identification of the PT cartridge from that of the aPTT cartridge.

In other embodiments, the resistor may be implemented between the amperometric pin 1095 and the conductometric low pin 1120. As should be understood by those of ordinary skill in the art, the concept of using a resistor to identify the type of cartridge may be implemented in any of the sensor/cartridge arrangements described herein. Moreover different values for the resistor can be obtained by varying the geometries of the wire or using varied materials for the wire (e.g., using TiW rather than gold), which can then be used for identifying different cartridges without departing from the spirit and scope of the present invention.

Figure 43:
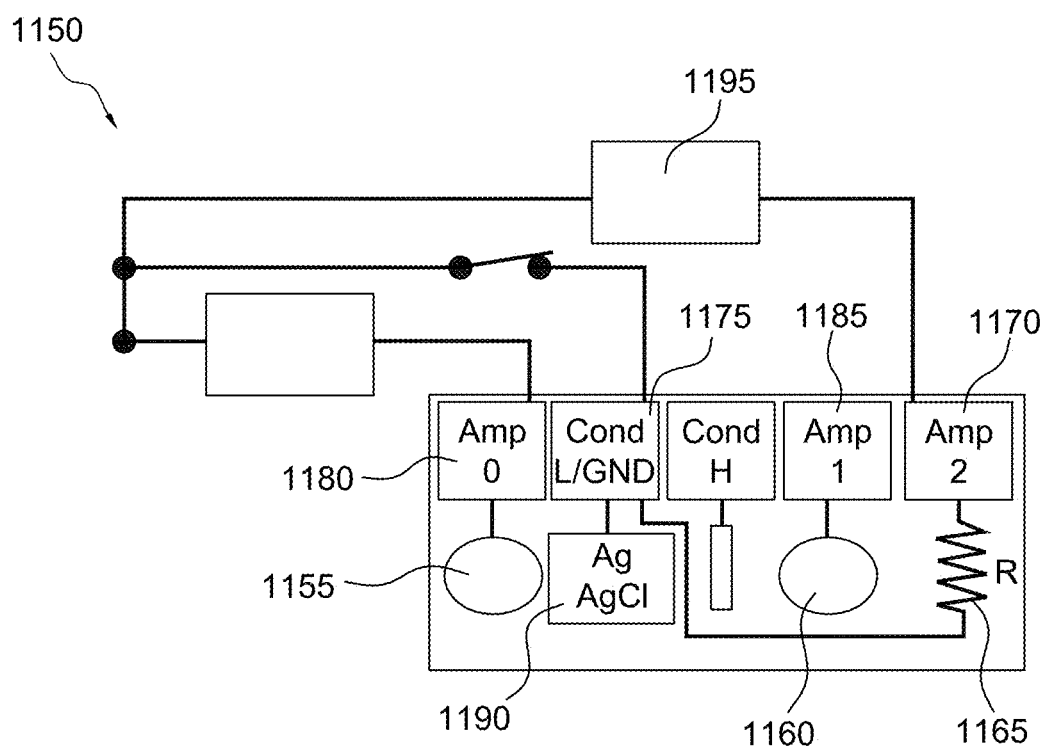

In order to impart the cartridge identification functionality into a multiple sensor chip arrangement (e.g., the arrangement shown in FIG. 18), an additional mechanism or means may be included in the arrangement for cartridge identification. As shown in FIG. 43 for a multiple (e.g., two) electrode arrangement 1150, for example, a PT analyte detection electrode 1155 and an aPTT analyte detection electrode 1160, a resistor 1165 can be implemented between an unused amperometric pin 1170 and the conductometric low pin 1175. The PT analyte detection electrode 1155 may be connected to the amperometric pin 1180, the aPTT analyte detection electrode 1160 may be connected to the amperometric pin 1185, the resistor 1165 may be connected to the unused amperometric pin 1170 and the conductometric low pin 1175, and the reference electrode 1190 may be connected to the conductometric low pin 1175. The resistance of the resistor 1165 may be measured by a detector 1195 by applying a small voltage, e.g., 1mV, between the unused amperometric pin 1170 and the conductometric low pin 1175, subsequent to (e.g., immediately after) the cartridge being inserted into the analyzer. The value of the measured resistance can then be used for cartridge identification. For example, each cartridge type (e.g., i-STAT® cartridges EC8+, CG8+, EG7+, CHEM8+, etc.) may be associated with a certain resistance or resistance range such that a measured resistance of the cartridge may be used to identify the type of cartridge using a look-up table.

As discussed above, the resistor 1165 may be comprised of a metal wire, preferably a gold wire manufactured at a same time as the contact pads and sensor electrode. The gold wire may be as small as 5 µm wide and 0.1 µm thick, which forms an area of 0.5 µm². As the resistivity of gold is 2.44 µΩ-cm, or 0.0244Ω-µm, a 1000 µm long gold wire will have a resistance of 0.0244 Ω-µm*1000 µm/0.5 µm²=48.8Ω. After the cartridge is inserted into the analyzer, a small voltage, e.g., 0.5 mV may be applied and a current of around 10 uA may be generated and detected by the analyzer. To minimize the power consumption, optionally the gold wire could be longer, the applied voltage could be lower, or the time for the application of the voltage could be shorter.

Ellagic Acid Formulations for use in a Coagulation Assays

In preferred embodiments, a coagulation test reagent is provided for comprising an ellagic acid formulation including ellagic acid and an agent for stably solubilizing the ellagic acid. The ellagic acid is a coagulation activator and is configured to activate the intrinsic pathway, for example, to perform an aPTT assay, as discussed in detail herein. The agent is a solvent or a compound that is configured to overcome the aqueous insolubility of ellagic acid and stably solubilize the ellagic acid. The agent may comprise one or more of sodium hydroxide, methanol, a polyether compound, and cyclodextrin.

In one embodiment, the agent may comprise sodium hydroxide. Sodium hydroxide can be used as solvent to help dissolve water insoluble compounds that have an acidic functional group such as ellagic acid. Sodium hydroxide reacts with the acidic functional group and forms a water soluble salt. In one embodiment, an ellagic acid formulation comprising sodium hydroxide as the solvent for solubilizing the ellagic acid may be prepared by mixing ellagic acid with sodium hydroxide, and optional deionized water to form an ellagic acid solution. However, the addition of sodium hyrdoxide to ellagic acid generates decomposition products (i.e., inactive ellagic acid) based on the dehydration of alcohol groups and/or the saponification reaction of the two ester groups found in ellagic acid. Consequently, in some embodiments, the ellagic acid solution may be pH neutralized to retain at least 40%, preferably at least 80%, of the ellagic acid as active ellagic acid e.g., the two ester groups of ellagic acid have not undergone a saponification reaction), which enhances the stability of the ellagic acid solution. For example, the preparation of the ellagic acid formulation may further comprise: (i) dissolving the ellagic acid into solution with the agent at neutral pH, (ii) adding an alkali (e.g., sodium hydroxide) to the solution to increase the pH of the solution into a pH range of 10-12.5, (iii) mixing the solution for a period of about 1 to 10 minutes, and (iv) adding an acid (e.g., hydrochloric acid) to the activator solution to return the pH to a neutral pH (e.g., a pH of about 7.3) to retain at least 40%, preferably at least 80%, of the ellagic acid as active ellagic acid (e.g., non-saponified ellagic acid). Thereafter, the ellagic acid solution may be microdispensed as a reagent or part of a reagent for use in a coagulation assay in accordance with various aspects of the present invention.

In another embodiment, the agent may comprise methanol. Methanol is a colorless liquid, completely miscible with water and organic solvents. Ellagic acid has been demonstrated to be slightly soluble in methanol. In one embodiment, an ellagic acid formulation comprising methanol as the solvent for solubilizing the ellagic acid may be prepared by mixing ellagic acid with methanol, and optional deionized water to form an ellagic acid solution. In some embodiments, the ellagic acid solution may be pH neutralized to enhance the stability of the ellagic acid solution. Thereafter, the ellagic acid solution may be microdispensed as a reagent or part of a reagent for use in a coagulation assay in accordance with various aspects of the present invention.

However, methanol solubility is commonly not adequate for many of the coagualtion assay embodiments described herein for single use diagnostic cartridges.

In another embodiment, the agent may comprise a polyether compound. Polyether compounds are a class of organic substances prepared by joining together or polymerizing many molecules of simpler compounds (monomers) by establishing ether links between them; polyethers, which may be either chainlike or networklike in molecular structure. Polyether compounds are commonly water-soluble liquids or waxy solids used in cosmetic and pharmaceutical preparations and in the manufacture of emulsifying or wetting agents and lubricants. Specifically, polyethylene glycol (PEG) has been demonstrated as having a high solubility property and is commonly used as a solvent and lubricant (see, e.g., Bala et al., 2006, Journal of Pharmaceutical and Biomedical Analysis, 40:206-10). However, the use of PEG to solubilize ellagic acid and the performance thereof in a single use coagulation assay device has not been previously explored.

The polyether compound may be selected from the group consisting of PEG, polyethylene oxide, polyoxyethylene, and mixtures thereof. In some embodiments, the agent comprises PEG having a molecular weight from about 200 to about 500000, more specifically a molecular weight from about 200 to 4000, preferably a molecular weight from about 200 to about 400.

In one embodiment, an ellagic acid formulation comprising a polyether compound (e.g., PEG) as the solvent for solubilizing the ellagic acid may be prepared by mixing ellagic acid with a polyether compound, and optional deionized water to form an ellagic acid solution. Thereafter, the ellagic acid solution may be microdispensed as a reagent or part of a reagent for use in a coagulation assay in accordance with various aspects of the present invention.

In another embodiment, the agent may comprise cyclodextrin. Cyclodextrin is a torus-like molecule which can increase solubility by allowing insoluble molecules to form inclusions with the hydrophobic core while still presenting a hydrophilic external feature which is more soluble in water (Raja & Kumar, 2013, Journal of Global Trends in Pharmaceutical Sciences, 4(2):1099-1106.) There are several approaches to prepare cyclodextrin inclusion complexes (Javery & Doshi, 2014, International Journal of Universal Pharmacy and Bio Sciences, 3(3):674-91). Beyond the standard cyclodextrins, several manufacturers have generated derivatives which provide enhanced solubility characteristics (Loftsson & Brewster, 2013, Drug Solubilization and stabilization by Cyclodextrin Drug Carriers in Drug Delivery Strategies for Poorly Water-Soluble Drugs (eds. Douroumis et al.), Wiley-Blackwell publisher, pp 67-101.) However, the use of cyclodextrin for enhancing the solubility of ellagic acid and the performance thereof in a single use coagulation assay device has not been previously explored.

Cyclodextrin may be selected from the group consisting of (2-hydroxypropyl)-beta-cyclodextrin, (2-hydroxypropyl)-gamma-cyclodextrin, alpha-cyclodextrin, gamma-cyclodextrin, dimethyl-alpha-cyclodextrin, trimethyl-alpha-cyclodextrin, dimethyl-beta-cyclodextrin, trimethyl-beta-cyclodextrin, dimethyl-gamma-cyclodextrin, trimethyl-gamma-cyclodextrin, glycosyl-alpha-cyclodextrin, glycosyl-beta-cyclodextrin, diglycosyl-beta-cyclodextrin, maltosyl-beta-cyclodextrin, dimaltosyl-beta-cyclodextrin, sulfobutylether-beta-cyclodextrin, and mixtures thereof. In some embodiments, the cyclodextrin is complexed with ellagic acid. More specifically, the cyclodextrin is a soluble host-guest complex with ellagic acid having a molar ratio of at least 1:1 (ellagic acid:cyclodextrin), preferably a molar ratio selected from the group consisting of: 1:1, 1:2, 1:3, 1:4, 1:5, 1:6, 1:7, 1:8, 1:9 and 1:10 (ellagic acid:cyclodextrin).

In one embodiment, an ellagic acid formulation comprising cyclodextrin as the compound for enhancing the solubility of ellagic acid may be prepared by mixing ellagic acid with cyclodextrin, and optional deionized water to form an ellagic acid solution. In some embodiments, the ellagic acid solution may be solubilized by exposure to a hydroxide base and neutralized to a neutral pH with an acid. For example, the ellagic acid solution may be solubilized by adding sodium hydroxide to increase the pH (e.g., a pH of about 12), and thereafter adding hydrochloric acid to decrease the pH to neutral (e.g., a pH of about 7.3). The ellagic acid solution may be pH neutralized to retain at least 40%, preferably at least 80%, of the ellagic acid as active ellagic acid (e.g., non-saponified ellagic acid), which enhances the stability of the ellagic acid solution. For example, the preparation of the ellagic acid formulation may further comprise: (i) dissolving the ellagic acid into solution with the agent at neutral pH, (ii) adding an alkali (e.g., sodium hydroxide) to the solution to increase the pH of the solution into a pH range of 10-12.5, (iii) mixing the solution for a period of about 1 to 10 minutes, and (iv) adding an acid (e.g., hydrochloric acid) to the activator solution to return the pH to a neutral pH (e.g., a pH of about 7.3) to retain at least 40%, preferably at least 60%, of the ellagic acid as non-saponified ellagic. Thereafter, the ellagic acid solution may be microdispensed as a reagent or part of a reagent for use in a coagulation assay in accordance with various aspects of the present invention.

In another embodiment the agent may be a polyether compound and cyclodextrin. An ellagic acid formulation comprising a polyether compound as the solvent and cyclodextrin as the compound for enhancing the solubility of ellagic acid may be prepared by mixing cyclodextrin with deionized water to form an emulsion of cyclodextrin. Mixing ellagic acid with a polyether compound to form an ellagic acid solution. Mixing the emulsion of cyclodextrin with the ellagic acid solution such that the cyclodextrin is complexed with the ellagic acid to create a cyclodextrin and ellagic acid emulsion. Thereafter, the cyclodextrin and ellagic acid emulsion may be microdispensed as a reagent or part of a reagent for use in a coagulation assay in accordance with various aspects of the present invention.

In some embodiments, the coagulation test reagent may include additional coagulation activators and/or a variety of other components that contribute to stabilization and/or deposition/dissolution characteristics of the reagent. In some embodiments, the additional coagulation activators may be selected from the group consisting of celite, kaolin, diatomaceous earth, clay, silicon dioxide, synthetic or natural lipids, and synthetic or natural phospholipids. In some embodiments, the other components may be selected from the group consisting of dextran, cyclodextrin, dextrin, tergitol, buffers, a carrier protein, one or more amino acids, stabilizers, antimicrobials, antioxidants, a detergent, a saccharide, a polysaccharide, sucrose, a polyether compound such polyethylene glycol, derivatives of polyethylene glycol, polyethylene oxide or polyoxyethylene, glycine, gelatin, buffer such as 4-(2-hydroxyethyl)-1-piperazineethanesulfonic acid (HEPES) buffer, rhamnose, trehalose, water, and sugars.

In preferred embodiments, a coagulation test system is provided for comprising (i) a reagent comprising an ellagic acid formulation including ellagic acid and an agent for stably solubilizing the ellagic acid, a phospholipid, and a buffer, and (2) a substrate comprising one or more thrombin-cleavable peptides with a detectable moiety. The phospholipid may be selected from the group consisting of 1,2-dioleoyl-sn-glycero-3 phosphocholine (PC), 1,2-dioleoyl-sn-glycero-3-phosphoethanolamine (PE), 1,2-dioleoyl-sn-glycero-3-phosphoinositol (ammonium salt) (PI), and 1,2-dioleoyl-sn-glycero-3-phospho-L-serine (sodium salt) (PS). The buffer may be selected from the group consisting of 4-(2-hydroxyethyl)-1-piperazineethanesulfonic acid (HEPES) buffer, N-2-hydroxyethyl piperazine-N-2-ethanesulfonic acid (HEPES), 3-(N-morpholino)-propanesulfonic acid (MOPS), Tris, N,N-bis-(hyrdroxyethyl)-2-aminocthancsulfonic acid (BES), N-tris-(hyrdroxymethyl)-methyl-2-aminoethanesulfonic acid (TES), 3-[N-tris (hydroxymethyl)methylamino]-2-hydroxypropanesulfonic acid (TAPSO), and 3-[N-tris-(hydroxymethyl-methylamino]-propanesulfonic acid (TAPS).

As discussed herein, the substrate may have an amide linkage that mimics the thrombin-cleaved amide linkage in fibrinogen. Specifically, the substrate may comprise one or more thrombin-cleavable peptides such as those selected from the group consisting of H-D-Phe-Pip-Arg, H-D-Chg-Abu-Arg, CBZ-Gly-Pro-Arg, Boc-Val-Pro-Arg, H-D-Phe-Pro-Arg, Cyclohexylglycine-Ala-Arg, Tos-Gly-Pro-Arg, Bz-Phe-Val-Arg, Boc-Val-Pro-Arg, Ac-Val-Pro-Arg, Ac-Val-Hyp-Arg, Ac-(8-amino-3,6,dioxaoctanoyl-Val-Pro-Arg, Ac-Gly-Pro-Arg, Ac-(8-amino-3,6,dioxaoctanoyl-Gly-Pro-Arg, Ac-Gly-Hyp-Arg and H-D-Chg-Abu-Arg. Thrombin typically cleaves the amide bond at the carboxy-terminus of the arginine residue because the bond structurally resembles the thrombin-cleaved amide linkage in fibrinogen. The product of the thrombin-substrate reaction includes electrochemically inert compounds such as Tos-Gly-Pro-Arg, H-D-Phe-Pip-Arg, and/or Bz-Phe-Val-Arg- and electroactive compounds or detectable moieties, preferably selected from the group consisting of p-aminophenol, a quinone, a ferrocene, ferrocyanide derivative, other organometallic species, p-nitroaniline, o-dianisidine, 4,4'-bensidine, 4-methoxy-2-naphthylamine, N-phenyl-p-phenylenediamine, N-[p-methoxyphenyl-]-p-phenylenediamine, and phenazine derivatives.

In preferred embodiments, the coagulation test system may further comprise at least one transducer (e.g., a working electrode or optical detector). In some embodiments, the reagent and substrate may be formed in a localized manner near the surface of the at least one transducer. For example, the reagent and the substrate may be printed as a dry substance directly on a surface of at least one transducer. A fluid sample may react with the reagent and the substrate without mixing (e.g., via passive diffusion) (although some degree of mixing, e.g., fluid oscillation, may be desired), in a localized manner creating a gradient from the sensor to atop of the conduit of active thrombin from activation of the coagulation pathway(s) via the ellagic acid, and the thrombin simultaneously converts the substrate and fibrinogen to their cleavage products. The electroactive compound or detectable moiety is detected by the at least one transducer.

In some embodiments, the at least one transducer of the coagulation test system may be a portion of a microfabricated sensor array. For example, a microfabricated sensor array may comprise one or more sensors or transducers comprising a first sensor or transducer (e.g., an aPTT sensor) and optionally a second sensor or transducer (e.g., a PT sensor). In order to facilitate operation of the coagulation test system within the sensor array, the coagulation test system may be constructed as a micro-environment sensor structure comprising the reagent and the substrate in any of a number of different arrangements such that the introduction of the fluid sample, e.g., whole blood, to the reagent and the substrate is localized to at least one transducer, as discussed herein. In particular, the micro-environment sensor structure is configured to physically separate one or more reagents and/or reaction products from one another to avoid cross-activation of the cascade pathways or other cross-sensor interference once the one or more reagents have become exposed to the fluid sample.

In order to physically separate the coagulation test system from other assays to avoid cross-activation and promote localization of electrochemical or optical signals over the transducers, the coagulation test system may further comprise an immobilized substrate and/or reagent-polymer layer selectively patterned over the at least transducer. For example, an aqueous polymer matrix comprising one or more of the reagent, the substrate, and a polymer, such as a photoformable polymer, may be utilized for immobilizing the reagent and/or substrate on or near the at least one transducer in any of a number of different arrangements, as discussed herein (see, e.g., FIGS. 7A-7C and 13A-13C). In some embodiments, the polymer may be selected from the group consisting of: hydroxypropyl cellulose, and Elvace, carboxymethyl cellulose, polylactic acid, polylactic acid, poly(lactic co-glycolic acid), celluloses, derivatives of cellulose, hydroxypropylmethylcellulose acetate succinate, inulin, fructose, fructans, derivatives of fructans, and polyglycolic acid. Additionally, the polymer layer may also comprise.

Advantageously, the ellagic acid formulations of the present invention are configured to provide the ellagic acid in a highly soluble format for use in a coagulation testing solution. Even more advantageously, the ellagic acid formulations of the present invention are configured to provide the ellagic acid in a highly soluble format that is highly stable for long term storage and reduces the assay time of an aPTT coagulation assay.

The present invention will be better understood in view of the following non-limiting examples.

EXAMPLES

Example 1: Ellagic Acid in Sodium Hydroxide

Initially 0.0204 g of ellagic acid from Sigma (Cat#E2250-10G) was added to 300 uL of 1M NaOH to create a 0.34% (3.4 mg/mL) partially solubilized solution of ellagic acid. Thereafter, 300 uL of the partially solubilized solution of ellagic acid was diluted with 5.7 mL of deionized water to create a diluted solubilized solution of ellagic acid. Thereafter, 1 ml of the diluted solubilized solution of ellagic acid was further diluted with 33 mL of deionized water to create approximately 100 ug/mL of diluted solubilized solution of ellagic acid for high performance liquid chromatography (HPLC) injection. A sample of the diluted solubilized solution of ellagic acid was retained for a fresh HPLC injection, and another sample of the diluted solubilized solution of ellagic acid was placed in storage at room temperature for 2 days prior to HPLC injection.

HPLC conditions were as follows: the ellagic acid preparations were chromatographed on an Agilent 1200 HPLC Instrument using an Agilent Zorbax Eclipse XDB-C18 column (5 um, 4.6×150 mm) with a flow rate of 0.6 ml/min. The mobile phases were A: Acetonitrile, and B: 1% Acetic Acid using the following gradient Table 1.

TABLE 1

| Time (min) | A(%) | B(%) |
| --- | --- | --- |
| 0 | 5 | 98 |
| 35 | 15 | 85 |
| 55 | 25 | 75 |
| 73 | 55 | 45 |
| 78 | 100 | 0 |
| 83 | 100 | 0 |
| 90 | 5 | 95 |

Figure 44:
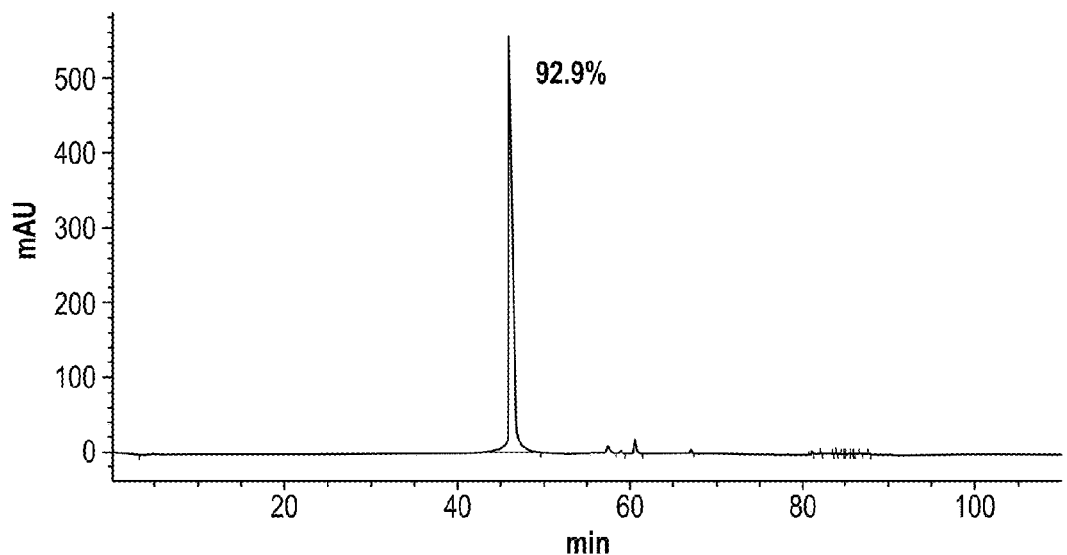
FIG. 44 shows an HPLC chromatograph of an ellagic acid preparation freshly made in sodium hydroxide.
Figure 45:
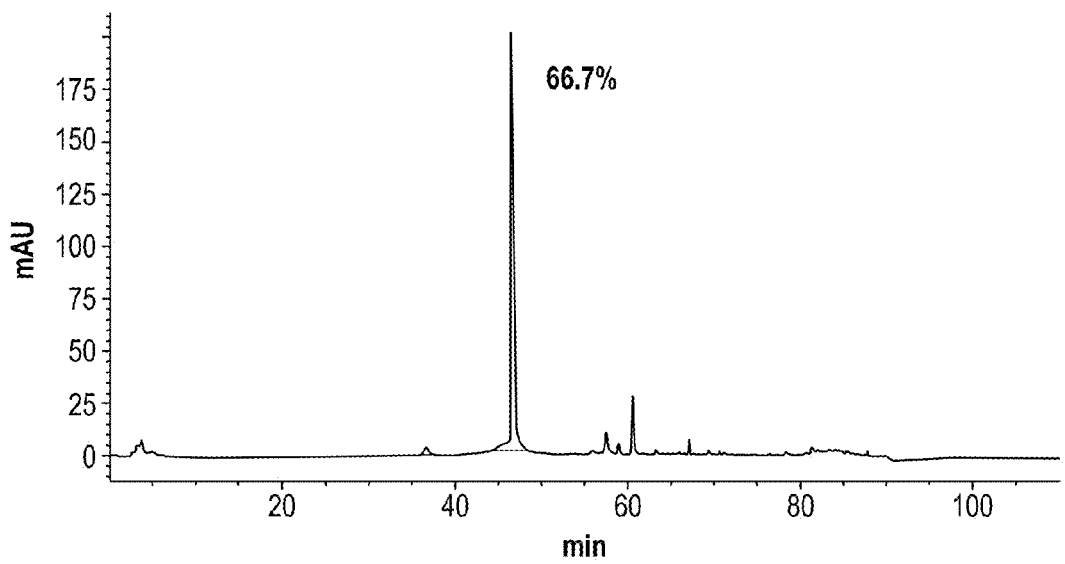
FIG. 45 shows an HPLC chromatograph of an ellagic acid preparation made in sodium hydroxide and stored for 2 days at room temperature.

FIGS. 44-57 show peak intensity (mAU) vs retention time was captured at wavelengths of a wavelength of 260 nm, but the other wavelengths (e.g., 280, 320 and 360 nm) were used to ascertain the presence of any other contaminants. The peak area percentage and intensity was captured from each run. FIG. 44 shows an HPLC chromatograph of the ellagic acid preparation freshly made in sodium hydroxide. FIG. 45 shows an HPLC chromatograph of the ellagic acid preparation made in sodium hydroxide and stored for 2 days at room temperature. The data from FIGS. 44 and 45 shows that the ellagic acid prepared in sodium hydroxide is undergoing decomposition (i.e., a drop from 92.9% to 66.7%). It would be expected that the saponification reaction would be dependent on time, temperature, and concentration with respect to the observed rates of decomposition. This data also shows that the storage of the ellagic acid in the presence of sodium hydroxide without pH neutralization would generate variable results in the coagulation assay such as an aPTT assay.

Example 2: Ellagic Acid in Methanol

Figure 46:
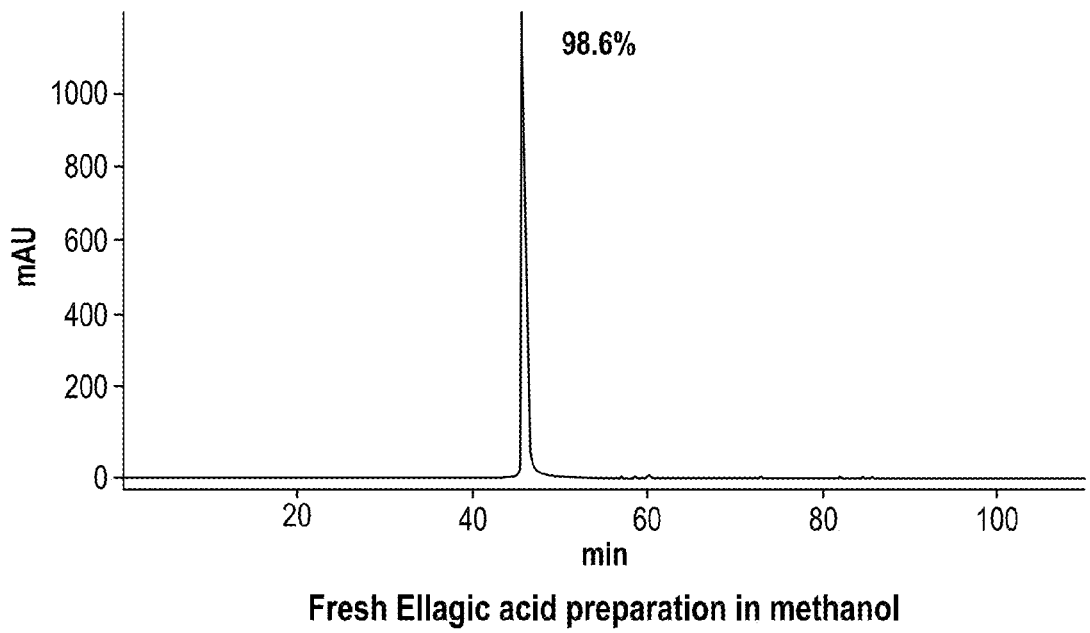
FIG. 46 shows an HPLC chromatograph of an ellagic acid preparation freshly made in methanol.
Figure 47:
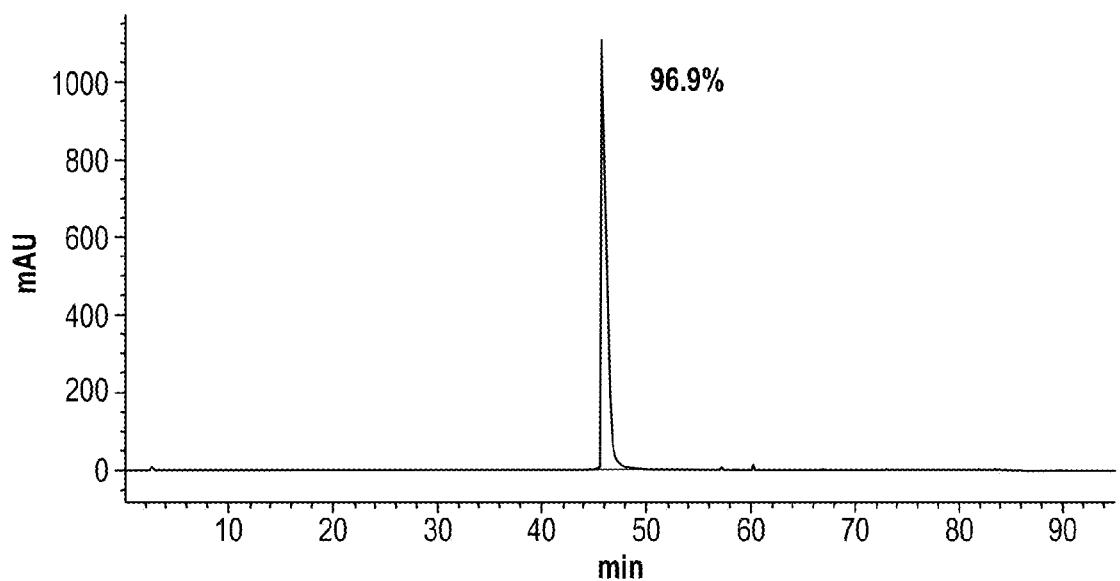
FIG. 47 shows an HPLC chromatograph of an ellagic acid preparation made in methanol and stored for 6 days at room temperature.
Figure 48:
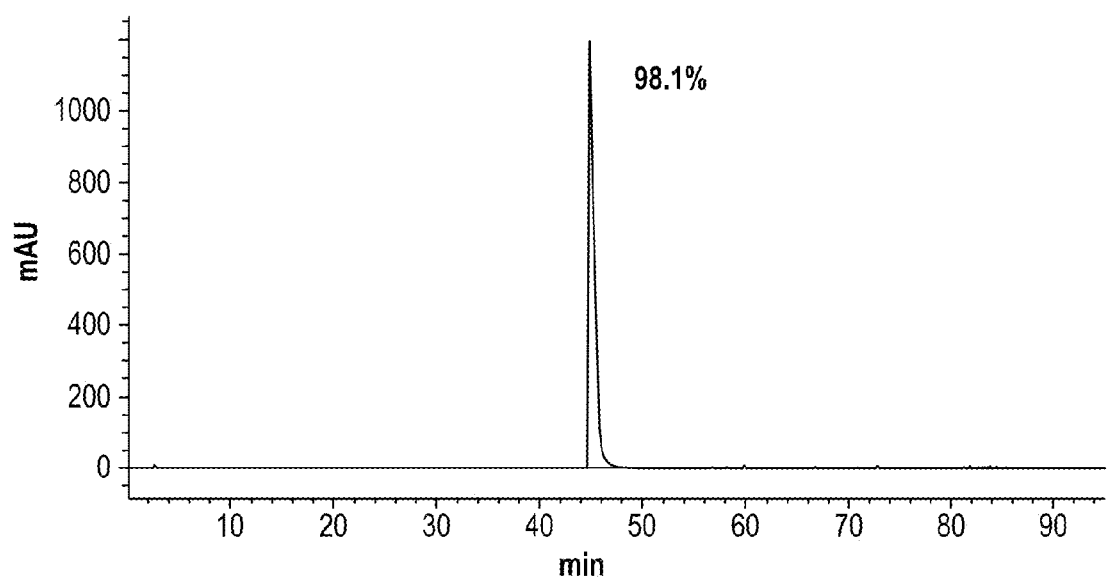
FIG. 48 shows an HPLC chromatograph of an ellagic acid preparation made in methanol and stored 13 days at room temperature.

Initially 0.0364 g of ellagic acid from Sigma (Cat#E2250-10G) was added to 3.64 mL of methanol generating a partially solubilized solution of ellagic acid with a concentration of about 10 mg/mL. After rapidly mixing the partially solubilized solution of ellagic acid, 100 uL of the 10 mg/mL solution was added to 9.9 mL of methanol, generating approximately 100 ug/mL of solubilized solution of ellagic acid for HPLC injection. A sample of the solubilized solution of ellagic acid was retained for a fresh HPLC injection, another sample of the solubilized solution of ellagic acid was placed in storage at room temperature for 6 days prior to HPLC injection, and another sample of the solubilized solution of ellagic acid was placed in storage at room temperature for 13 days prior to HPLC injection. Each sample of the solubilized solution of ellagic acid was injected into the HPLC using the same HPLC conditions as discussed with respect to Example 1. FIG. 46 shows an HPLC chromatograph of the ellagic acid preparation freshly made in methanol. FIG. 47 shows an HPLC chromatograph of the ellagic acid preparation made in methanol and stored for 6 days at room temperature. FIG. 48 shows an HPLC chromatograph of an ellagic acid preparation made in methanol and stored 13 days at room temperature. The data from FIGS. 46-48 shows no significant observable decomposition in the ellagic acid preparations.

Example 3: Ellagic Acid in 1M PEG 400

Figure 49:
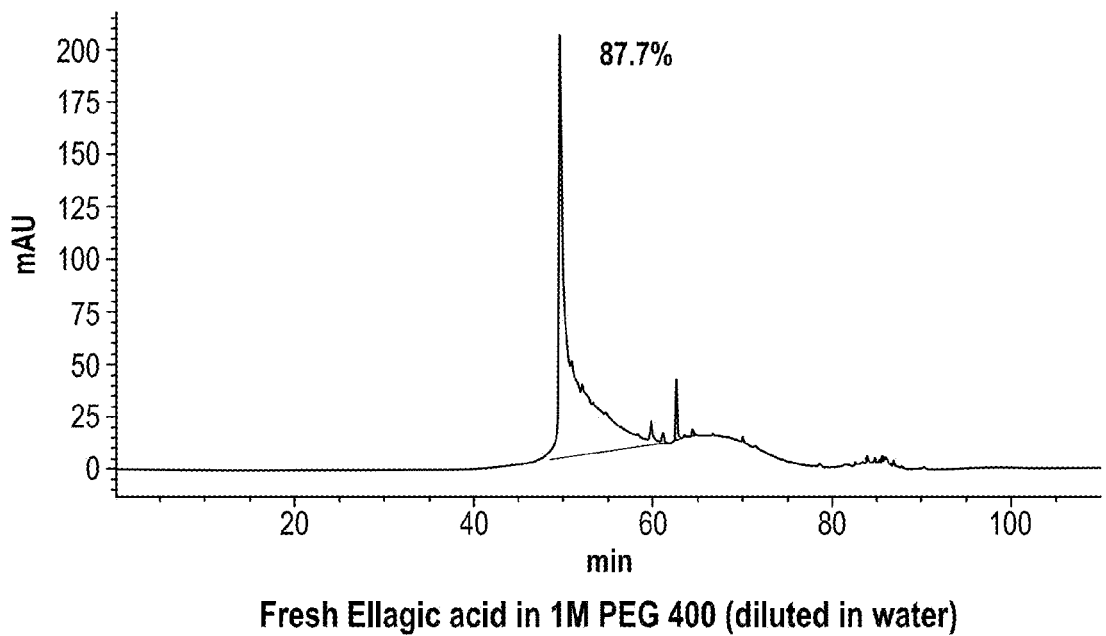
FIG. 49 shows an HPLC chromatograph of a fresh ellagic acid preparation made in 1M PEG 400 and diluted in water.
Figure 50:
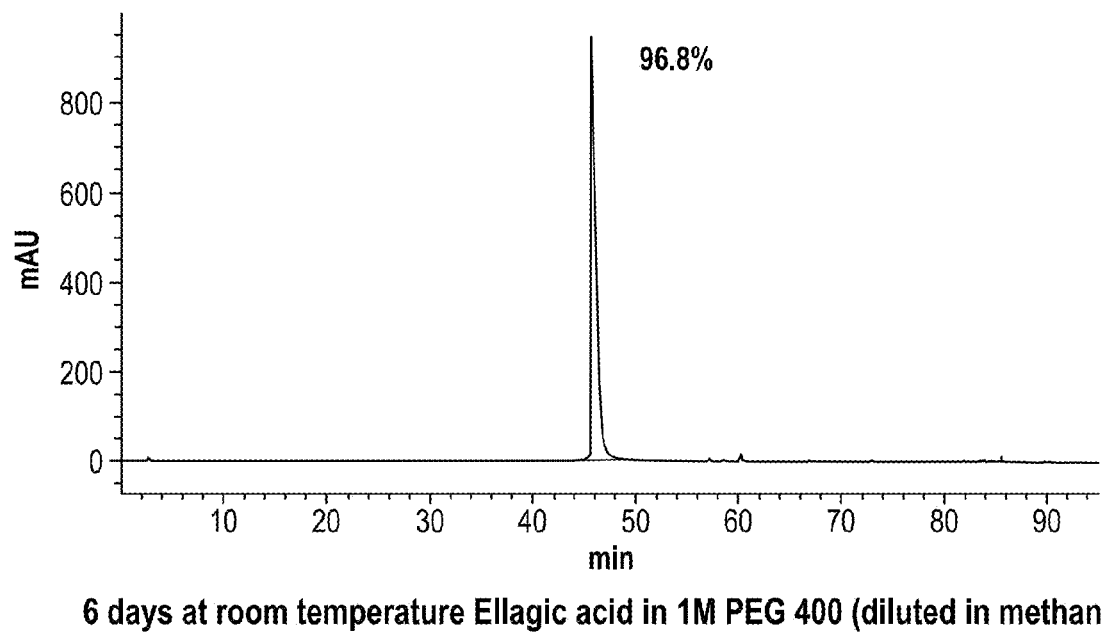
FIG. 50 shows an HPLC chromatograph of an ellagic acid preparation made in 1M PEG 400, stored 6 days at room temperature and diluted in methanol.
Figure 51:
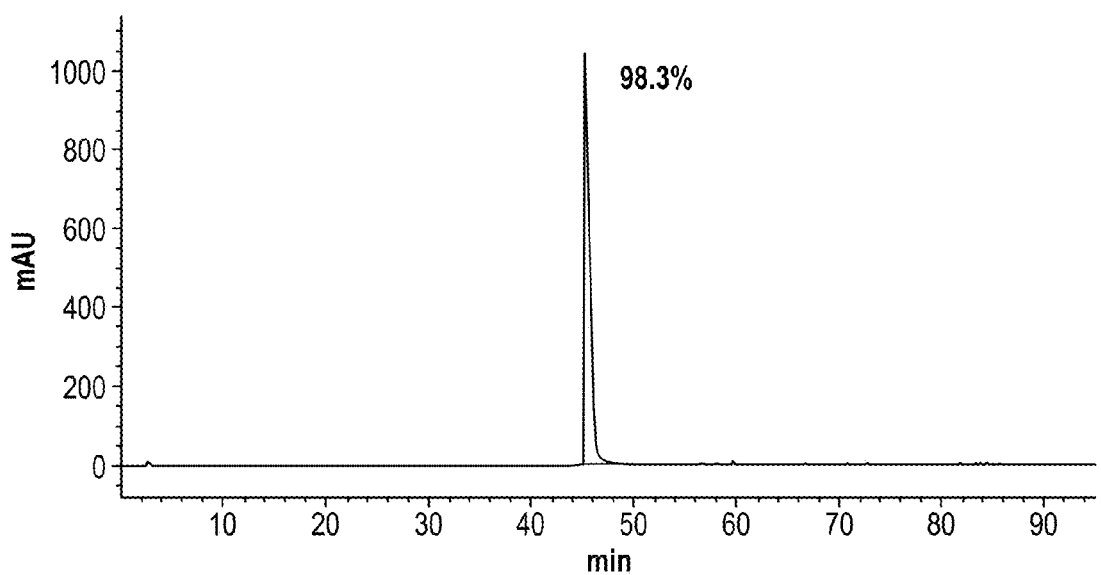
FIG. 51 shows an HPLC chromatograph of an ellagic acid preparation made in 1M PEG 400, stored 13 days at room temperature and diluted in methanol.

Initially 0.0224 g of ellagic acid from Sigma (Cat#E2250-10G) was added to 6 mL of 1M PEG 400 from Sigma (Cat#91893-250 mL-F) generating a partially solubilized solution of ellagic acid. The ellagic acid powder quickly solubilized in the solvent. Thereafter, the partially solubilized solution of ellagic acid was mixed by inverting the tube about 10 times, and sonicated for 10 minutes with a microtip probe to create a solubilized solution of ellagic acid. A sample of the solubilized solution of ellagic acid was retained for a fresh HPLC injection, another sample of the solubilized solution of ellagic acid was placed in storage at room temperature for 6 days prior to HPLC injection, and another sample of the solubilized solution of ellagic acid was placed in storage at room temperature for 13 days prior to HPLC injection. For the fresh HPLC injection, 27 uL of the solubilized solution of ellagic acid was diluted with 1 mL of deionized water creating approximately 100 ug/mL of diluted solubilized solution of ellagic acid for HPLC injection. For the 6 day and 13 day storage at room temperature HPLC injections, 27 uL of each of the solubilized solutions of ellagic acid were diluted with 1 ml of methanol creating approximately 100 ug/mL of diluted solubilized solution of ellagic acid for HPLC injection. Each sample of the solubilized solution of ellagic acid was injected into the HPLC using the same HPLC conditions as discussed with respect to Example 1. FIG. 49 shows an HPLC chromatograph of the fresh ellagic acid preparation made in 1M PEG 400 and diluted in deionized water prior to HPLC injection. FIG. 50 shows an HPLC chromatograph of an ellagic acid preparation made in 1M PEG 400, stored 6 days at room temperature, and diluted in methanol prior to HPLC injection. FIG. 51 shows an ellagic acid preparation made in 1M PEG 400, stored 13 days at room temperature, and diluted in methanol prior to HPLC injection. The data from FIGS. 49-51 suggests that the ellagic acid preparations are stable for 13 days at room temperature when prepared with 1M PEG 400.

Example 4: Ellagic Acid in 100 mM PEG 4000

Figure 52:
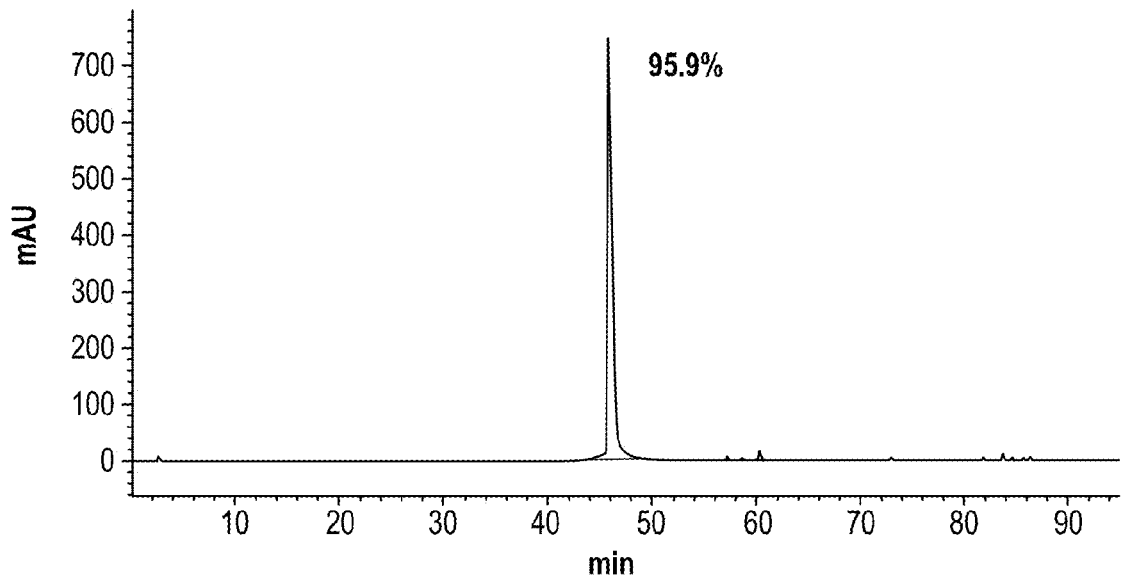
FIG. 52 shows an HPLC chromatograph of an ellagic acid preparation made in 100 mM PEG 4000 and stored for 6 days at room temperature.
Figure 53:
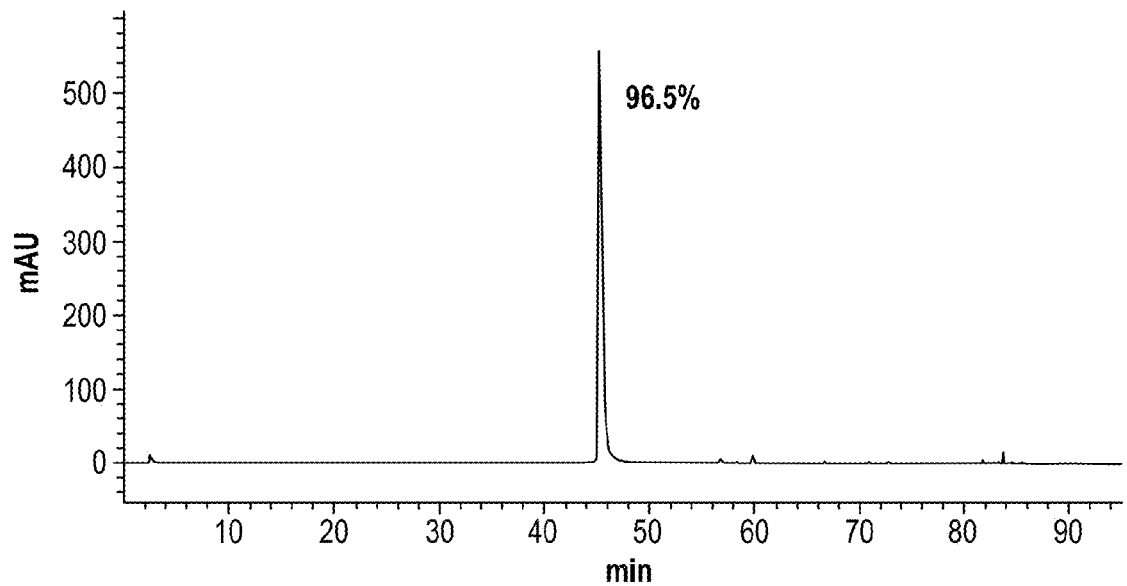
FIG. 53 shows an HPLC chromatograph of an ellagic acid preparation made in 100 mM PEG 4000 and stored for 13 days at room temperature.

Initially 20 g of PEG 4000 (Sigma 95904-250G-F) was added to deionized water up to 50 mL to create a solution of 100 mM PEG 4000, which was mixed on a rotator for an hour. Thereafter, 0.0494 g of ellagic acid from Sigma (Cat#E2250-10G) was added to 6 mL of the 100 mM PEG 4000 solution generating an insoluble mixture of ellagic acid and PEG. Another 13.8 mL of the 100 mM PEG 4000 solution was added to the insoluble mixture of ellagic acid and PEG to create a mixture with approximately 0.34% ellagic acid concentration, which was mixed on a rotator overnight. Thereafter, the partially solubilized solution of ellagic acid was sonicated at 50% for 10 minutes with a microtip probe to create a solubilized solution of ellagic acid. A sample of the solubilized solution of ellagic acid was retained for a fresh HPLC injection, another sample of the solubilized solution of ellagic acid was placed in storage at room temperature for 6 days prior to HPLC injection, and another sample of the solubilized solution of ellagic acid was placed in storage at room temperature for 13 days prior to HPLC injection. For the fresh HPLC injection, and the 6 day and 13 day storage at room temperature HPLC injections, 29.4 uL of each of the solubilized solutions of ellagic acid were diluted with 1 ml of methanol creating approximately 100 ug/mL of diluted solubilized solution of ellagic acid for HPLC injection. Each sample of the solubilized solution of ellagic acid was injected into the HPLC using the same HPLC conditions as discussed with respect to Example 1. FIG. 52 shows an HPLC chromatograph of an ellagic acid preparation made in 100 mM PEG 4000 and stored 6 days at room temperature, which did not change significantly from the fresh preparation (data not shown). FIG. 53 shows an ellagic acid preparation made in 100 mM PEG 4000 and stored 13 days at room temperature. The data from FIGS. 52 and 53 suggests that the ellagic acid preparations are stable for 13 days at room temperature when prepared with 100 mM PEG 4000.

Example 5: Ellagic Acid in PEG 400 and beta-cyclodextrin

Figure 54:
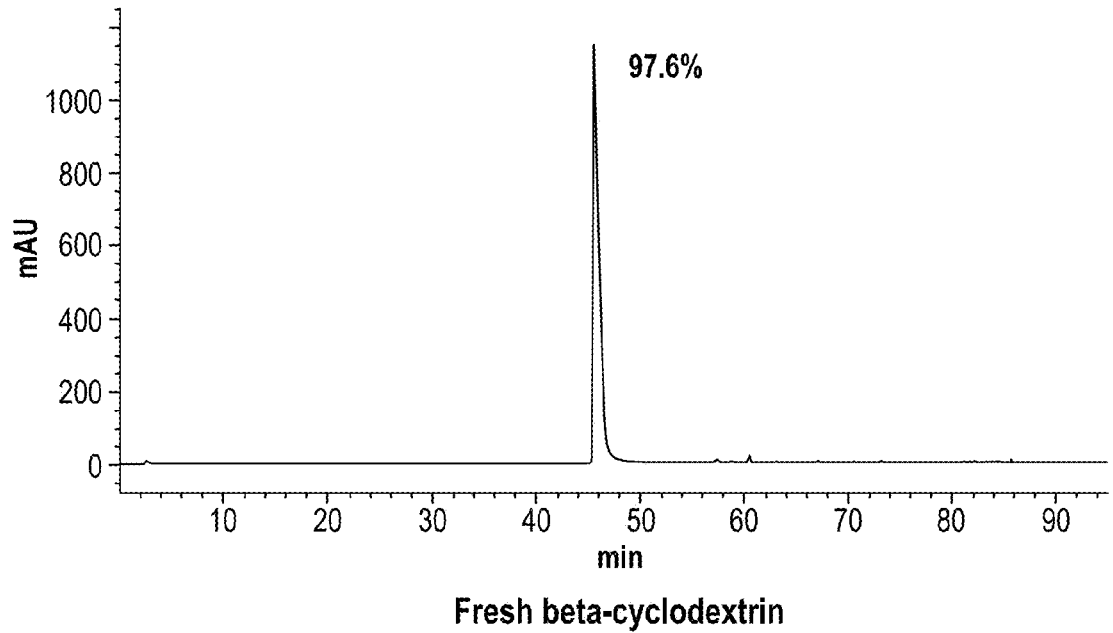
FIG. 54 shows an HPLC chromatograph of a fresh ellagic acid preparation made with beta-cyclodextrin.
Figure 55:
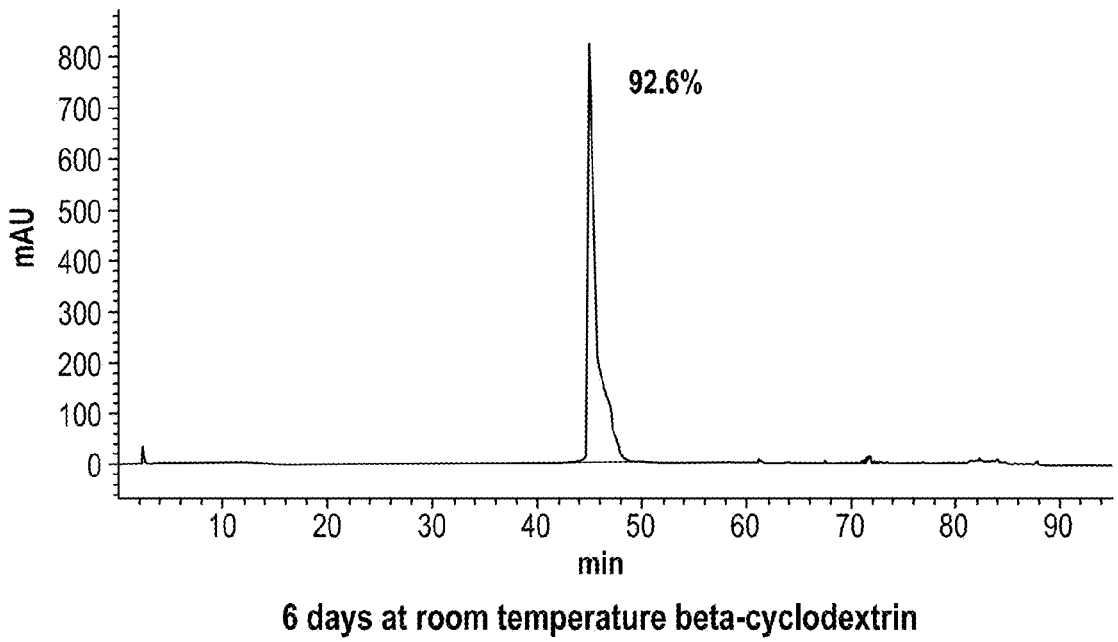
FIG. 55 shows an HPLC chromatograph of an ellagic acid preparation made with beta-cyclodextrin and stored for 6 days at room temperature.
Figure 56:
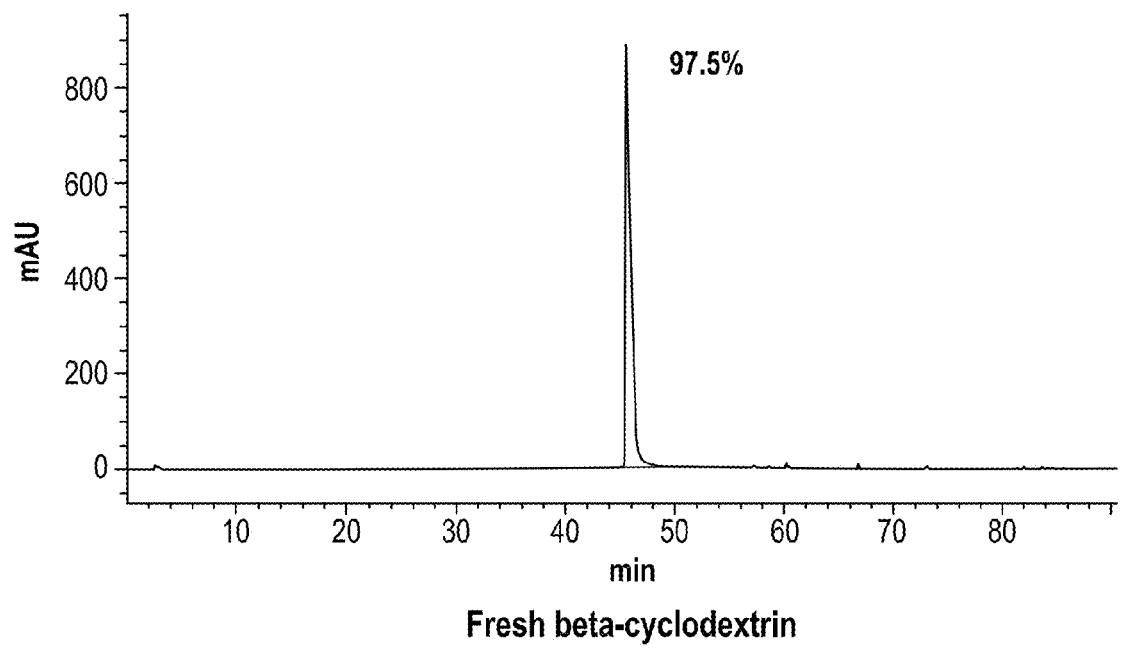
FIG. 56 shows an HPLC chromatograph of a fresh ellagic acid preparation made with a pH shocked beta-cyclodextrin.
Figure 57:
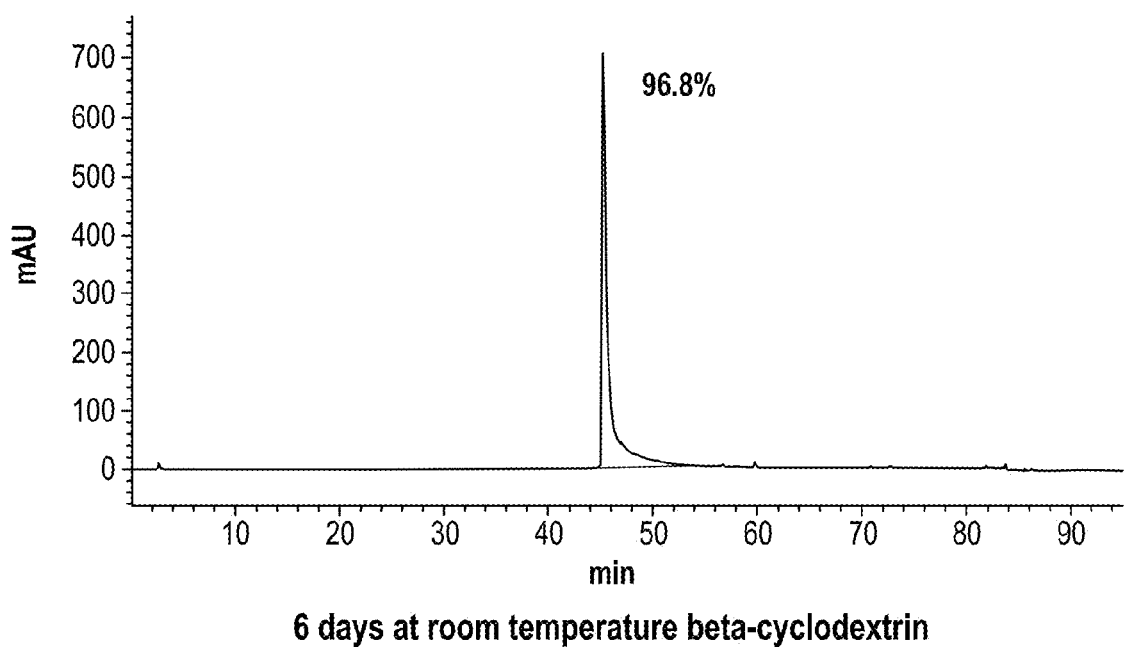
FIG. 57 shows an HPLC chromatograph of an ellagic acid preparation made with a pH shocked beta-cyclodextrin and stored 6 days at room temperature.

Initially 0.6614 g of beta-cyclodextrin from Sigma (Cat# C4805-100G) was added to 6.0 mL of deionized water generating an emulsion of beta-cyclodextrin. Thereafter, 0.3003 g of ellagic acid from Sigma (Cat#E2250-10G) was added to 8 mL of the 1M PEG 400 solution and vortexed to generate a thick emulsion of ellagic acid. After stirring the thick emulsion of ellagic acid on high, 2 mL of the beta-cyclodextrin emulsion was added to the thick emulsion of ellagic acid. Thereafter, the beta-cyclodextrin and ellagic acid emulsion was stirred for one hour at room temperature, and sonicated for 10 minutes with a microtip probe to create a mixed beta-cyclodextrin and ellagic acid emulsion. The mixed beta-cyclodextrin and ellagic acid emulsion was left to stand overnight at room temperature. After standing overnight, the mixed beta-cyclodextrin and ellagic acid emulsion had no observable precipitate. To create a (1×) concentration of the mixed beta-cyclodextrin and ellagic acid emulsion, 1 ml of the mixed beta-cyclodextrin and ellagic acid emulsion was added to 9 ml of 1M PEG 400 solution. Thereafter, 33.3 ul of the (1×) concentration of the mixed beta-cyclodextrin and ellagic acid emulsion was added to 1 mL of methanol to create approximately 100 ug/mL of diluted solubilized solution of ellagic acid for HPLC injection. A sample of the solubilized solution of ellagic acid was retained for a fresh HPLC injection, and another sample of the solubilized solution of ellagic acid was placed in storage at room temperature for 6 days prior to HPLC injection. Each sample of the solubilized solution of ellagic acid was injected into the HPLC using the same HPLC conditions as discussed with respect to Example 1. FIG. 54 shows an HPLC chromatograph of the fresh ellagic acid preparation made with beta-cyclodextrin. FIG. 55 shows an HPLC chromatograph of the ellagic acid preparation made with beta-cyclodextrin and stored for 6 days at room temperature. The data from FIGS. 56 and 57 shows no significant observable decomposition in the ellagic acid preparations made with beta-cyclodextrin.

Example 6: Ellagic Acid in pH Shocked Beta-Cyclodextrin

Initially 0.3454 g of ellagic acid from Sigma (Cat#E2250-10G) was added to 2.65 g of beta-cyclodextrin from Sigma (Cat# C4805-100G) and mixed to generate an emulsion of ellagic acid. Thereafter, the beta-cyclodextrin and ellagic acid emulsion was diluted with 5 mL of deionized water and stirred at a high setting to create a diluted beta-cyclodextrin and ellagic acid emulsion. Thereafter, 10M of sodium hydroxide was added dropwise (about 2-3 mL) to the diluted beta-cyclodextrin and ellagic acid emulsion to create a brownish murky solution which appeared solubilized. Thereafter, concentrated hydrochloric acid was added dropwise to the solubilized beta-cyclodextrin and ellagic acid emulsion while measuring the pH of the solution to create a bright yellow colored beta-cyclodextrin and ellagic acid emulsion with a pH of 7.31 and a final volume of 11.5 mL. To create a (1×) concentration of the mixed beta-cyclodextrin and ellagic acid emulsion, 1 ml of the mixed beta-cyclodextrin and ellagic acid emulsion was added to 9 ml of 1M PEG 400 solution and sonicated for 10 minutes. Thereafter, 29 ul of the (1×) concentration of the mixed beta-cyclodextrin and ellagic acid emulsion was added to 1 mL of methanol to create approximately 100 ug/mL of diluted solubilized solution of ellagic acid for HPLC injection. A sample of the solubilized solution of ellagic acid was retained for a fresh HPLC injection, and another sample of the solubilized solution of ellagic acid was placed in storage at room temperature for 6 days prior to HPLC injection. Each sample of the solubilized solution of ellagic acid was injected into the HPLC using the same HPLC conditions as discussed with respect to Example 1. FIG. 56 shows an HPLC chromatograph of the fresh ellagic acid preparation made with pH shocked beta-cyclodextrin. FIG. 57 shows an HPLC chromatograph of the ellagic acid preparation made with pH shocked beta-cyclodextrin and stored for 6 days at room temperature. The data from FIGS. 56 and 57 shows no significant observable decomposition in the ellagic acid preparations made with pH shocked beta-cyclodextrin.

Example 7: aPTT Coagulation Cocktail Preparation Method

Samples tested for use as an aPTT reagent included: Example 1: 1M sodium hydroxide solubilized ellagic acid solution, Example 3: 1M PEG 400 solubilized ellagic acid solution, Example 4: 100 mM PEG 4000 solubilized ellagic acid solution, Example 5: PEG 400 and beta-cyclodextrin solubilized ellagic acid solution, and Example 6: pH shocked beta-cyclodextrin solubilized ellagic acid solution.

The aPTT cocktail was prepared as follows: initially 0.06 g of poly(ethylene glycol) methyl ether from Sigma (Cat#81323) and 30 uL of a salt (1M NaCl or KCl) were added to a ratio of 6 mL of each of the above tested samples (Examples 1, 3, 4, 5, and 6) to create an activator solution. Thereafter, 30 g of Chloroform from Sigma (Cat# C2432) was added to 2 vials each of 0.006 g of butylated hydroxyanisole from Sigma (Cat#B1253). The phospholipids 1,2-dioleoyl-sn-glycero-3 phosphocholine (PC), 1,2-dioleoyl-sn-glycero-3-phosphoethanolamine (PE), 1,2-dioleoyl-sn-glycero-3-phosphoinositol (ammonium salt) (PI) and 1,2-dioleoyl-sn-glycero-3-phospho-L-serine (sodium salt) (PS) were solubilized in the chloroform/butylated hydroxyanisole solvent. The phospholipids were combined in a ratio of 1.16 uL of 10.3 mM PS, 1.69 uL 10.6 mM PC, 0.535 uL 11.2 mM PE and 17.5 uL of 0.103 mM PI. Additionally, a HEPES/Rhamnose solution was prepared as 50 mM HEPES from Sigma (Cat#H0887-100 mL) with 0.5% Rhamnose from Sigma (Cat#R3875).

The aPTT "reagent" was prepared by adding 75 uL of the activator solution prepared and tested above (Examples 1, 3, 4, 5, and 6) to 20.9 uL of the phospholipid preparation. The aPTT "substrate" RF16-1 had the sequence of Tos-Gly-Pro-Arg-MeOpADA. The aPTT "substrate" was prepared by suspending 20 mg of the substrate in 7.366 mL of deionized water or 10 mM acetic acid to make a substrate with a final concentration of 4 mM.

A solution matrix was prepared by adding 0.4288 g of albumen fraction V from Sigma (Cat# A-7906) to 2.538 g glycine from Sigma (Cat# G-7126), 0.3938 g methoxypolyethylene glycol from Sigma (Cat#81323), and 1.4 g of sucrose from Sigma (Cat# S9378) to create the solution matrix made up to 250 mL with deionized water. A 6.5% solution of HPC(80000) was prepared by adding 0.065 g of hydroxypropyl cellulose from Aldrich (Cat#435007) to 1 mL of deionized water.

Figure 58:
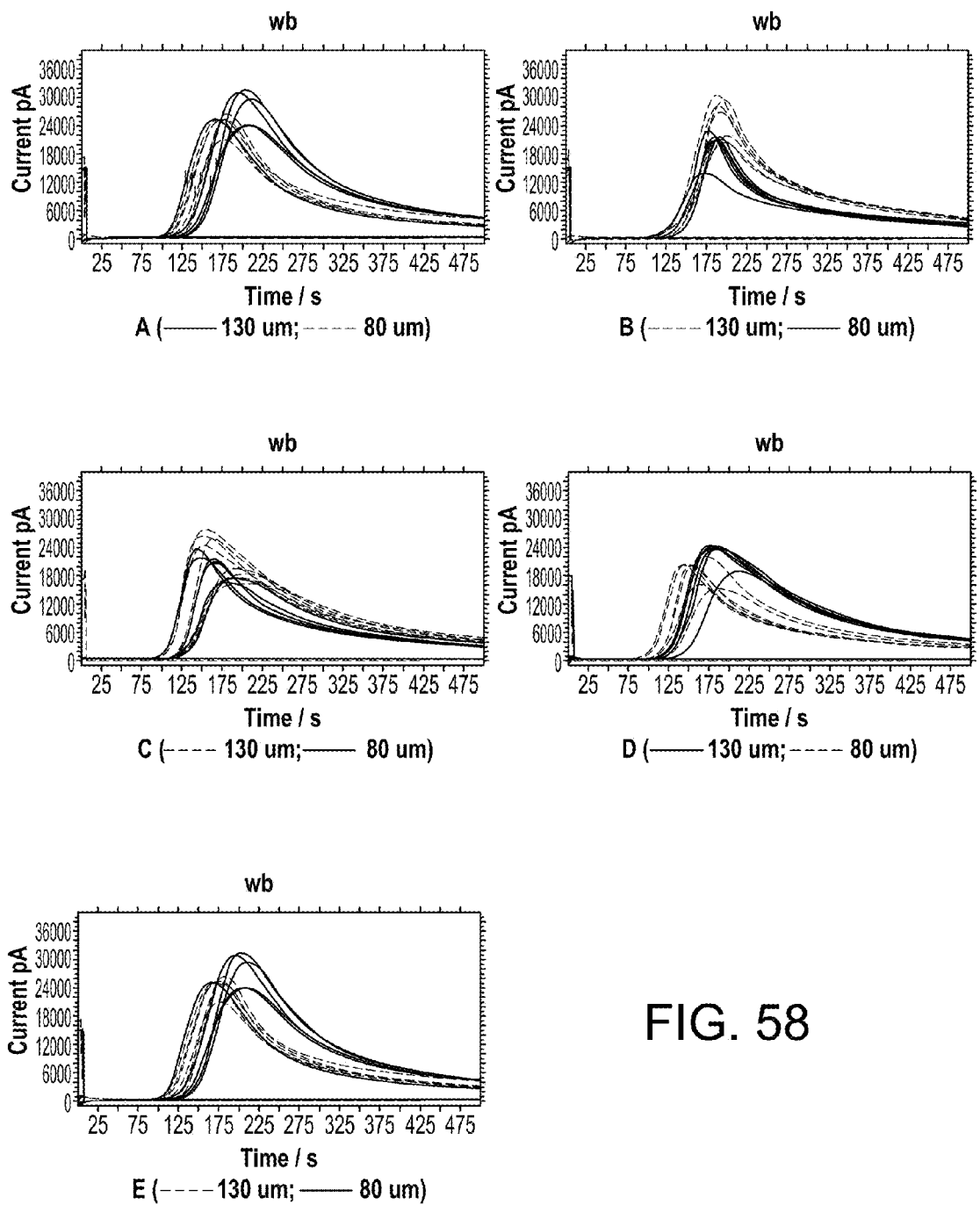
FIG. 58 shows chronoamperometric plots of current over time using aPTT assay reagents.

The aPTT cocktail used for microdispensing on the aforementioned coagulation chip was made by taking 30 uL of the aPTT "reagent", adding 33 uL of the HEPES/Rhamnose solution, 22 uL of the solution matrix, 40 uL Of 6.5% HPC(80000), 25 uL of 4 mM aPTT "substrate" RF16-1 for a total volume of 150 uL. This material was microdispensed onto the aPTT chip and assembled into a cartridge device for testing. FIG. 58 shows chronoamperometric plots of the current over time using the aPTT assay reagents generated from the above tested samples with whole blood (Plot A. Ellagic Acid prepared with sodium hydroxide (baseline). Plot B. Ellagic Acid prepared in PEG 4000 solution. Plot C. Ellagic Acid prepared in PEG 400 solution. Plot D. Ellagic Acid prepared in a PEG 400 solution containing beta-cyclodextrin. Plot E. Ellagic Acid prepared in a pH shocked beta-cyclodextrin solution. Print thicknesses of the microdispensed prints are indicated for each plot). Stabilized solutions of ellagic acid were able to produce clotting curves and times which were similar to the baseline ellagic acid preparation method. Aged preparations of stable ellagic acid were shown to produce acceptable clotting parameters (data not shown).

Example 8: aPTT Coagulation Cocktail Preparation Method for pH Shock Ellagic Acid The aPTT cocktail was prepared as follows: initially took 05 mL of deionized water in a 50 mL centrifuge tube and added 0.3456 g of ellagic acid (Sigma E2250-10G Lot#SLBD8693V) to create a ellagic acid emulsion. The ellagic acid emulsion was mixed by vortexing for 10 seconds. Thereafter, 2.7 mL of 2M NaOH (added 675 uL at a time with mixing after each addition) was added to the ellagic acid emulsion. Thereafter, 3.8 mL of 1N HCl (950 uL at a time with mixing after each addition) was added to the ellagic acid emulsion. The final weight of the ellagic acid emulsion was recorded to be 13 g and the final pH was 7.57. The ellagic acid emulsion was then sonicated for 10 minutes at 50%, selecting the microprobe option. This mixed ellagic acid emulsion was labeled as the EA stock solution. A (1×) concentration of the EA stock solution was created by weighing 0.5 g of the EA stock solution in a 5 mL Eppendorf tube, to which 150 uL of 1M KCl/1% MePeg solution and 4350 uL of deionized water were added. The (1×) concentration of the EA stock solution was used hereafter as the activator solution.

The aPTT "reagent" was prepared by adding 75 uL of the activator solution prepared above to 75 uL of the phospholipid preparation. The phospholipid preparation was made in a manner similar to that discussed with respect to Example 7, and included aliquoting 20.9 uL of the PS:PC:PE:PI blend into a glass vial, evaporating off the chloroform under a gentle nitrogen gas stream followed by rehydration in the 50 mM Hepes+0.5% Rhamnose buffer.

The aPTT "substrate" RF16-1 had the sequence of Tos-Gly-Pro-Arg-MeOpADA. The aPTT "substrate" was prepared by suspending 20 mg of the substrate in 14.732 mL of deionized water to make a substrate with a final concentration of 2 mM.

The solution matrix was prepared by adding 0.4288 g of albumen fraction V from Sigma (Cat# A-7906) to 2.538 g glycine from Sigma (Cat# G-7126), 0.3938 g methoxypolyethylene glycol from Sigma (Cat#81323), and 1.4 g of sucrose from Sigma (Cat# S9378) to create a solution matrix made up to 250 mL with deionized water. A 6.5% solution of HPC(80000) was prepared by adding 0.065 g of hydroxypropyl cellulose from Aldrich (Cat#435007) to 1 mL of deionized water.

Figure 59:
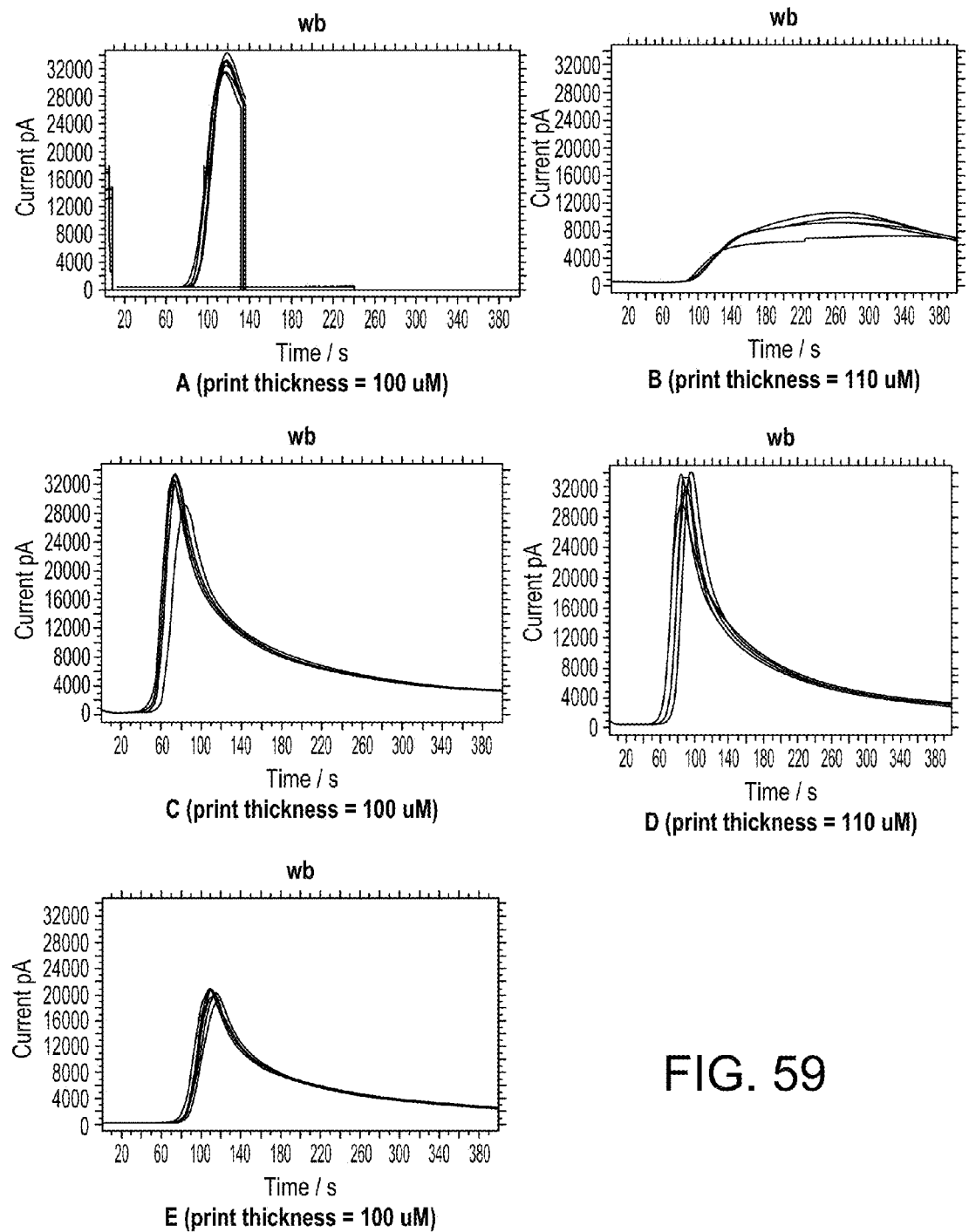
FIG. 59 show chronoamperometrics plots of current over time using aPTT assay reagents.

The aPTT cocktail used for microdispensing on the aforementioned coagulation chip was made by taking 75 uL of the aPTT "reagent", adding 6.6 uL of 1M HEPES, 13.4 uL of 40% Rhamnose solution, 55 uL of the solution matrix, 100 uL Of 6.5% HPC(80000), 125 uL of 2 mM aPTT "substrate" RF16-1 for a total volume of 375 uL. This material was microdispensed onto the aPTT chip and assembled into a cartridge device for testing. FIG. 59 shows a chronoamperometric plot (A. Ellagic Acid Only solution prepared by pH shock method) of the current over time using the aPTT assay reagent with whole blood.

Example 9: aPTT Coagulation Cocktail Preparation Method for Ellagic Acid in 1M PEG 400

The aPTT cocktail was prepared as follows: initially added 0.0224 g of ellagic acid from Sigma (Cat#E2250-10G) to 6 mL of 1M PEG 400 from Sigma (Cat#91893-250 mL-F). The ellagic acid powder quickly solubilized in the solvent. Thereafter, the partially solubilized solution of ellagic acid was mixed by inverting the tube about 10 times, and sonicated for 10 minutes with a microtip probe to create a solubilized solution of ellagic acid. To create a (1×) concentration of the solubilized solution of ellagic acid, 0.5 mL of the solubilized solution of ellagic acid was added to 4.5 mL of deionized water. Thereafter, 30 uL of 1M KCl from Fisher Scientific (Cat# P-217-10) and 0.01 g of MePeg from Sigma (Cat#81323) were added to 1 mL of the (1×) solubilized solution of ellagic acid. This solution was used hereafter as the activator solution.

The aPTT "reagent" was prepared by adding 75 uL of the activator solution prepared above to 75 uL of the phospholipid preparation. The phospholipid preparation was made in a manner similar to that discussed with respect to Example 7, and included aliquoting 20.9 uL of the PS:PC:PE:PI blend into a glass vial, evaporating off the chloroform under a gentle nitrogen gas stream followed by rehydration in the 50 mM Hepes+0.5% Rhamnose buffer.

The aPTT "substrate" RF16-1 had the sequence of Tos-Gly-Pro-Arg-MeOpADA. The aPTT "substrate" was prepared by suspending 20 mg of the substrate in 14.732 mL of deionized water to make a substrate with a final concentration of 2 mM.

The solution matrix was prepared by adding 0.4288 g of albumen fraction V from Sigma (Cat# A-7906) to 2.538 g glycine from Sigma (Cat# G-7126), 0.3938 g methoxypolyethylene glycol from Sigma (Cat#81323), and 1.4 g of sucrose from Sigma (Cat# S9378) to create a solution matrix made up to 250 mL with deionized water. A 6.5% solution of HPC(80000) was prepared by adding 0.065 g of hydroxypropyl cellulose from Aldrich (Cat#435007) to 1 mL of deionized water.

The aPTT cocktail used for microdispensing on the aforementioned coagulation chip was made by taking 75 uL of the aPTT "reagent", adding 6.6 uL of 1M HEPES, 13.4 uL of 40% Rhamnose solution, 55 uL of the solution matrix, 100 uL Of 6.5% HPC(80000), 125 uL of 2 mM aPTT "substrate" RF16-1 for a total volume of 375 uL. This material was microdispensed onto the aPTT chip and assembled into a cartridge device for testing. FIG. 59 shows a chronoamperometric plot (B. Ellagic Acid prepared in 1M PEG 400 solution) of the current over time using the aPTT assay reagent in whole blood.

Example 10: aPTT Coagulation Cocktail Preparation Method for Ellagic Acid and beta-cyclodextrin The aPTT cocktail was prepared as follows: initially added 0.3454 g of ellagic acid from Sigma (Cat#E2250-

10G) to 2.65 g of beta-cyclodextrin from Sigma (Cat# C4805-100G) into a 30 ml, beaker with a stir bar. Thereafter, 5.7 mL of deionized water and 300 uL of 1M sodium hydroxide was added to the beta-cyclodextrin and ellagic acid emulsion and stirred at a high setting to create a solubilized beta-cyclodextrin and ellagic acid emulsion. Thereafter, 500 uL of 2M sodium hydroxide was added to the solubilized beta-cyclodextrin and ellagic acid emulsion while measuring the pH of the solution to create a bright yellow colored beta-cyclodextrin and ellagic acid emulsion with a final volume of 7.5 mL. To create a (1×) concentration of the mixed beta-cyclodextrin and ellagic acid emulsion, 0.5 ml of the mixed beta-cyclodextrin and ellagic acid emulsion was added to 4.5 mL od deionized water and sonicated for 10 minutes. Thereafter, 30 uL of 1M KCl from Fisher Scientific (Cat# P-217-10) and 0.01 g of MePeg from Sigma (Cat#81323) were added to 1 mL of the (1×) solubilized solution of ellagic acid. This solution was used hereafter as the activator solution.

The aPTT "reagent" was prepared by adding 75 uL of the activator solution prepared above to 75 uL of the phospholipid preparation. The phospholipid preparation was made in a manner similar to that discussed with respect to Example 7, and included aliquoting 20.9 uL of the PS:PC:PE:PI blend into a glass vial, evaporating off the chloroform under a gentle nitrogen gas stream followed by rehydration in the 50 mM Hepes+0.5% Rhamnose buffer.

The aPTT "substrate" RF16-1 had the sequence of Tos-Gly-Pro-Arg-MeOpADA. The aPTT "substrate" was prepared by suspending 20 mg of the substrate in 14.732 mL of deionized water to make a substrate with a final concentration of 2 mM.

The solution matrix was prepared by adding 0.4288 g of albumen fraction V from Sigma (Cat# A-7906) to 2.538 g glycine from Sigma (Cat# G-7126), 0.3938 g methoxypolyethylene glycol from Sigma (Cat#81323), and 1.4 g of sucrose from Sigma (Cat# S9378) to create a Solution matrix made up to 250 mL with deionized water. A 6.5% solution of HPC(80000) was prepared by adding 0.065 g of hydroxypropyl cellulose from Aldrich (Cat#435007) to 1 mL of deionized water.

The aPTT cocktail used for microdispensing on the aforementioned coagulation chip was made by taking 75 uL of the aPTT "reagent", adding 6.6 uL of 1M HEPES, 13.4 uL of 40% Rhamnose solution, 55 uL of the Solution matrix, 100 uL Of 6.5% HPC(80000), 125 uL of 2 mM aPTT "substrate" RF16-1 for a total volume of 375 uL. This material was microdispensed onto the aPTT chip and assembled into a cartridge device for testing. FIG. 59 shows a chronoamperometric plot (C. Ellagic acid prepared in deionized water containing beta-cyclodextrin) of the current over time using the aPTT assay reagent in whole blood.

Example 11: aPTT Coagulation Cocktail Preparation Method for pH Shock Ellagic Acid, PEG, and Beta-Cyclodextrin The aPTT cocktail was prepared as follows: initially 2.65 g of beta-cyclodextrin from Sigma (Cat# C4805-100G) was added to 5.0 mL of deionized water and 0.3454 g of ellagic acid from Sigma (Cat#E2250-10G) generating an emulsion of ellagic acid and beta-cyclodextrin. Thereafter, 2M sodium hydroxide was added dropwise to the ellagic acid and beta-cyclodextrin emulsion until a pH of 12 was reached (approximately 2.5 mL). Thereafter, 1M hydrochloric acid was added dropwise to the ellagic acid and beta-cyclodextrin emulsion until a pH of 7.31 was reached (approximately 3.7 mL). The ellagic acid and beta-cyclodextrin emulsion was then poured into a 50 mL centrifuge tune and sonicated for 10 minutes. Thereafter, 1.5 mL of deionized water was added to the ellagic acid and beta-cyclodextrin emulsion to achieve an ellagic acid and beta-cyclodextrin emulsion with a final volume of 11.5 mL. To create a (1×) concentration of the ellagic acid and beta-cyclodextrin emulsion, 0.2 mL of the ellagic acid and beta-cyclodextrin emulsion was added to 1.8 mL of 50 mM PEG 400 solution. Thereafter, 30 uL of 1M KCl from Fisher Scientific (Cat# P-217-10) and 0.01 g of MePeg from Sigma (Cat#81323) were added to 1 mL of the (1×) solubilized solution of ellagic acid. This solution was used hereafter as the activator solution.

The aPTT "reagent" was prepared by adding 75 uL of the activator solution prepared above to 75 uL of the phospholipid preparation. The phospholipid preparation was made in a manner similar to that discussed with respect to Example 7, and included aliquoting 20.9 uL of the PS:PC:PE:PI blend into a glass vial, evaporating off the chloroform under a gentle nitrogen gas stream followed by rehydration in the 50 mM Hepes+0.5% Rhamnose buffer.

The aPTT "substrate" RF16-1 had the sequence of Tos-Gly-Pro-Arg-MeOpADA. The aPTT "substrate" was prepared by suspending 20 mg of the substrate in 14.732 mL of deionized water to make a substrate with a final concentration of 2 mM.

The solution matrix was prepared by adding 0.4288 g of albumen fraction V from Sigma (Cat# A-7906) to 2.538 g glycine from Sigma (Cat# G-7126), 0.3938 g methoxypolyethylene glycol from Sigma (Cat#81323), and 1.4 g of sucrose from Sigma (Cat# S9378) to create a solution matrix made up to 250 mL with deionized water. A 6.5% solution of HPC(80000) was prepared by adding 0.065 g of hydroxypropyl cellulose from Aldrich (Cat#435007) to 1 mL of deionized water.

The aPTT cocktail used for microdispensing on the aforementioned coagulation chip was made by taking 75 uL of the aPTT "reagent", adding 6.6 uL of 1M HEPES, 13.4 uL of 40% Rhamnose solution, 55 uL of the solution matrix, 100 uL Of 6.5% HPC(80000), 125 uL of 2 mM aPTT "substrate" RF16-1 for a total volume of 375 uL. This material was microdispensed onto the aPTT chip and assembled into a cartridge device for testing. FIG. 59 shows a chronoamperometric plot (D. Ellagic Acid prepared in a 50 mM PEG 400 solution containing beta-cyclodextrin) of the current over time using the aPTT assay reagent in whole blood.

Example 12: aPTT Coagulation Cocktail Preparation Method for Ellagic Acid and Methyl-Cyclodextrin The aPTT cocktail was prepared as follows: initially 3.02 g of methyl-cyclodextrin from Sigma (Cat# C4555-10G) was added to 5.0 mL of deionized water and 0.3454 g of ellagic acid from Sigma (Cat#E2250-10G) generating an emulsion of ellagic acid and methyl-cyclodextrin. Thereafter, 2M sodium hydroxide was added dropwise to the ellagic acid and methyl-cyclodextrin emulsion until a pH of 12.5 was reached. Thereafter, 1M hydrochloric acid was added dropwise to the ellagic acid and methyl-cyclodextrin emulsion until a pH of 7.3 was reached. The ellagic acid and methyl-cyclodextrin emulsion was then poured into a 50 mL centrifuge tune and sonicated for 10 minutes. Thereafter, 1.5 mL of deionized water was added to the ellagic acid and methyl-cyclodextrin emulsion to achieve an ellagic acid and methyl-cyclodextrin emulsion with a final volume of 11.5 mL. To create a (1×) concentration of the ellagic acid and methyl-cyclodextrin emulsion, 0.5 mL of the ellagic acid and methyl-cyclodextrin emulsion was added to 4.5 mL of deionized water. Thereafter, 30 uL of 1M KCl from Fisher Scientific (Cat# P-217-10) and 0.01 g of MePeg from Sigma (Cat#81323) were added to 1 mL of the (1×) solubilized solution of ellagic acid. This solution was used hereafter as the activator solution.

The aPTT "reagent" was prepared by adding 75 uL of the activator solution prepared above to 75 uL of the phospholipid preparation. The phospholipid preparation was made in a manner similar to that discussed with respect to Example 7, and included aliquoting 20.9 uL of the PS:PC:PE:PI blend into a glass vial, evaporating off the chloroform under a gentle nitrogen gas stream followed by rehydration in the 50 mM Hepes+0.5% Rhamnose buffer.

The aPTT "substrate" RF16-1 had the sequence of Tos-Gly-Pro-Arg-MeOpADA. The aPTT "substrate" was prepared by suspending 20 mg of the substrate in 14.732 mL of deionized water to make a substrate with a final concentration of 2 mM.

The solution matrix was prepared by adding 0.4288 g of albumen fraction V from Sigma (Cat# A-7906) to 2.538 g glycine from Sigma (Cat# G-7126), 0.3938 g methoxypolyethylene glycol from Sigma (Cat#81323), and 1.4 g of sucrose from Sigma (Cat# S9378) to create a solution matrix made up to 250 mL with deionized water. A 6.5% solution of HPC(80000) was prepared by adding 0.065 g of hydroxypropyl cellulose from Aldrich (Cat#435007) to 1 mL of deionized water.

The aPTT cocktail used for microdispensing on the aforementioned coagulation chip was made by taking 75 uL of the aPTT "reagent", adding 6.6 uL of 1M HEPES, 13.4 uL of 40% Rhamnose solution, 55 uL of the solution matrix, 100 uL Of 6.5% HPC(80000), 125 uL of 2 mM aPTT "substrate" RF16-1 for a total volume of 375 uL. This material was microdispensed onto the aPTT chip and assembled into a cartridge device for testing. FIG. 59 shows a chronoamperometric plot (E. Ellagic Acid prepared in deionized water containing methyl cyclodextrin) of the current over time using the aPTT assay reagent with whole blood. Stabilized solutions of ellagic acid shown in FIG. 59 were able to produce clotting curves and times which were similar to the baseline ellagic acid preparation method (A. Ellagic Acid Only solution prepared by pH shock method). Aged preparations of stable ellagic acid were shown to produce acceptable clotting parameters (data not shown).

While the invention has been described in terms of various preferred embodiments, those skilled in the art will recognize that various modifications, substitutions, omissions and changes can be made without departing from the spirit of the present invention. It is intended that the scope of the present invention be limited solely by the scope of the following claims. In addition, it should be appreciated by those skilled in the art that a plurality of the various embodiments of the invention, as described above, may be coupled with one another and incorporated into a single reader device.

We claim:

1. A coagulation test system comprising:
   a reagent comprising ellagic acid and an agent for stably solubilizing the ellagic acid; and
   a substrate comprising a thrombin-cleavable peptide with a detectable moiety,
   wherein the agent comprises a cyclodextrin,
   wherein the ellagic acid is stably solubilized,
   and wherein at least 80% of the ellagic acid is active ellagic acid.

2. The coagulation test system of claim 1, wherein the agent further comprises a polyether compound selected from the group consisting of polyethylene glycol, polyethylene oxide, polyoxyethylene, and mixtures thereof.

3. The coagulation test system of claim 2, wherein the polyether compound is the polyethylene glycol.

4. The coagulation test system of claim 1, wherein the cyclodextrin is selected from the group consisting of (2-hydroxypropyl)-beta-cyclodextrin, (2-hydroxypropyl)-gamma-cyclodextrin, alpha-cyclodextrin, gamma-cyclodextrin, dimethyl-alpha-cyclodextrin, trimethyl-alpha-cyclodextrin, dimethyl-beta-cyclodextrin, trimethyl-beta-cyclodextrin, dimethyl-gamma-cyclodextrin, trimethyl-gamma-cyclodextrin, glycosyl-alpha-cyclodextrin, glycosyl-beta-cyclodextrin, diglycosyl-beta-cyclodextrin, maltosyl-beta-cyclodextrin, dimaltosyl-beta-cyclodextrin, sulfobutylether-beta-cyclodextrin, and mixtures thereof.

5. The coagulation test system of claim 1, wherein the agent is the cyclodextrin, and the cyclodextrin is complexed with the ellagic acid.

6. The coagulation test system of claim 1, wherein the agent is the cyclodextrin, and the cyclodextrin is in a soluble host-guest complex with the ellagic acid at a molar ratio of at least 1:1 (ellagic acid:cyclodextrin).

7. The coagulation test system of claim 6, wherein the molar ratio is selected from the group consisting of 1:2, 1:3, 1:4, 1:5, 1:6, 1:7, 1:8, 1:9 and 1:10 (ellagic acid:cyclodextrin).

8. The coagulation test system of claim 1, wherein the agent is the cyclodextrin, which is a beta-cyclodextrin, and the beta-cyclodextrin is complexed with the ellagic acid.

9. The coagulation test system of claim 2, wherein the agent is the polyether compound and the cyclodextrin, and the cyclodextrin is complexed with the ellagic acid.

10. The coagulation test system of claim 9, wherein the cyclodextrin is selected from the group consisting of (2-hydroxypropyl)-beta-cyclodextrin, (2-hydroxypropyl)-gamma-cyclodextrin, alpha-cyclodextrin, gamma-cyclodextrin, dimethyl-alpha-cyclodextrin, trimethyl-alpha-cyclodextrin, dimethyl-beta-cyclodextrin, trimethyl-beta-cyclodextrin, dimethyl-gamma-cyclodextrin, trimethyl-gamma-cyclodextrin, glycosyl-alpha-cyclodextrin, glycosyl-beta-cyclodextrin, diglycosyl-beta-cyclodextrin, maltosyl-beta-cyclodextrin, dimaltosyl-beta-cyclodextrin, sulfobutylether-beta-cyclodextrin, and mixtures thereof.

11. The coagulation test system of claim 1, wherein the thrombin-cleavable peptide is selected from the group consisting of H-D-Phe-Pip-Arg, H-D-Chg-Abu-Arg, CBZ-Gly-Pro-Arg, Boc-Val-Pro-Arg, H-D-Phe-Pro-Arg, Cyclohexylglycine-Ala-Arg, Tos-Gly-Pro-Arg, Bz-Phe-Val-Arg, Boc-Val-Pro-Arg, Ac-Val-Pro-Arg, Ac-Val-Hyp-Arg, Ac-(8-amino-3,6,dioxaoctanoyl-Val-Pro-Arg, Ac-Gly-Pro-Arg, Ac-(8-amino-3,6,dioxaoctanoyl-Gly-Pro-Arg, Ac-Gly-Hyp-Arg and H-D-Chg-Abu-Arg.

12. The coagulation test system of claim 1, wherein the detectable moiety is selected from the group consisting of p-aminophenol, a quinone, a ferrocene, ferrocyanide, other organometallic species, p-nitroaniline, o-dianisidine, 4,4'-bensidine, 4-methoxy-2-naphthylamine, N-phenyl-p-phenylenediamine, N-[p-methoxyphenyl-]-p-phenylenediamine, and phenazine derivatives.

13. The coagulation test system of claim 1, further comprising at least one transducer coated with a polymer layer, wherein the polymer layer comprises the thrombin-cleavable peptide with the detectable moiety.

14. The coagulation test system of claim 13, wherein the reagent is an activated partial thromboplastin time (aPTT)

reagent formed as (i) a layer over the polymer layer, or (ii) a layer adjacent to the at least one transducer.

15. The coagulation test system of claim 13, wherein the reagent is an activated partial thromboplastin time (aPTT) reagent, and the polymer layer comprises the aPTT reagent.

16. The coagulation test system of claim 1, further comprising a buffer and a phospholipid.

17. The coagulation test system of claim 16, wherein the buffer is selected from the group consisting of 4-(2-hydroxyethyl)-1-piperazineethanesulfonic acid (HEPES) buffer, N-2-hydroxyethyl piperazine-N-2-ethanesulfonic acid (HEPES), 3-(N-morpholino)-propanesulfonic acid (MOPS), Tris, N,N-bis-(hydroxyethyl)-2-aminoethanesulfoni acid (BES), N-tris-(hydroxymethyl)-methyl-2-aminoethanesulfonic acid (TES), 3-[N-tris (hydroxymethyl) methylamino]-2-hydroxypropanesulfonic acid (TAPSO), and 3-[N-tris-(hydroxymethyl-methylamino]-propanesulfonic acid (TAPS).

18. The coagulation test system of claim 16, wherein the phospholipid is selected from the group consisting of 1,2-dioleoyl-sn-glycero-3 phosphocholine (PC), 1,2-dioleoyl-sn-glycero-3-phosphoethanolamine (PE), 1,2-dioleoyl-sn-glycero-3-phosphoinositol (PI), and 1,2-dioleoyl-sn-glycero-3-phospho-L-serine (sodium salt) (PS).

19. A method of forming a coagulation test system, the method comprising:
preparing an activator solution comprising ellagic acid and an agent comprising a cyclodextrin for stably solubilizing the ellagic acid, wherein the ellagic acid is stably solubilized, and wherein the ellagic acid comprises at least 80% of active ellagic acid;
mixing the activator solution with at least a phospholipid preparation to create a reagent solution; and
adding the reagent solution to a substrate comprising a thrombin-cleavable peptide with a detectable moiety to create an assay cocktail.

20. The method of claim 19, further comprising preparing a polymer matrix comprising a polymer, and adding the polymer matrix to the assay cocktail.

21. The method of claim 20, further comprising dispensing the assay cocktail over at least one transducer of a chip.

22. The method of claim 19, wherein the agent further comprises a polyether compound selected from the group consisting of polyethylene glycol, polyethylene oxide, polyoxyethylene, and mixtures thereof.

23. The method of claim 22, wherein the polyether compound is the polyethylene glycol.

24. The method of claim 19, wherein the cyclodextrin is selected from the group consisting of (2-hydroxypropyl)-beta-cyclodextrin, (2-hydroxypropyl)-gamma-cyclodextrin, alpha-cyclodextrin, gamma-cyclodextrin, dimethyl-alpha-cyclodextrin, trimethyl-alpha-cyclodextrin, dimethyl-beta-cyclodextrin, trimethyl-beta-cyclodextrin, dimethyl-gamma-cyclodextrin, trimethyl-gamma-cyclodextrin, glycosyl-alpha-cyclodextrin, glycosyl-beta-cyclodextrin, diglycosyl-beta-cyclodextrin, maltosyl-beta-cyclodextrin, dimaltosyl-beta-cyclodextrin, sulfobutylether-beta-cyclodextrin, and mixtures thereof.

25. The method of claim 19, wherein the agent is the cyclodextrin, and the cyclodextrin is complexed with the ellagic acid.

26. The method of claim 22, wherein the agent is the polyether compound and the cyclodextrin, and the cyclodextrin is complexed with the ellagic acid.

27. The method of claim 19, wherein the preparing the activator solution comprises:
dissolving the ellagic acid into the activator solution with the agent at neutral pH;
adding an alkali to the activator solution to increase the pH of the activator solution into a pH range of 10-12.5;
mixing the activator solution for a period of about 1 to 10 minutes;
adding an acid to the activator solution to return the pH to the neutral pH; and
mixing the activator solution with a buffer.

28. The method of claim 27, further comprising dispensing the assay cocktail over at least one transducer of a chip.

29. A sample analysis cartridge comprising:
an inlet chamber configured to receive a biological sample;
a conduit fluidically connected to the inlet chamber and configured to receive the biological sample from the inlet chamber; and
a micro-environment activated partial thromboplastin time (aPTT) sensor located within the conduit, the sensor comprising:
a reagent comprising ellagic acid and an agent for stably solubilizing the ellagic acid, wherein the agent comprises a cyclodextrin, wherein the ellagic acid is stably solubilized, and wherein at least 80% of the ellagic acid is active ellagic acid; and
at least one transducer coated with a polymer layer, wherein the polymer layer comprises a thrombin-cleavable peptide with a detectable moiety.

30. The coagulation test system of claim 1, wherein the reagent has a neutral pH.

* * * * *